(12) United States Patent
Boger

(10) Patent No.: US 7,915,270 B2
(45) Date of Patent: Mar. 29, 2011

(54) OXAZOLE KETONES AS MODULATORS OF FATTY ACID AMIDE HYDROLASE

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 1073 days.

(21) Appl. No.: 11/708,788

(22) Filed: Feb. 20, 2007

(65) Prior Publication Data
US 2007/0203156 A1 Aug. 30, 2007

Related U.S. Application Data

(60) Provisional application No. 60/774,322, filed on Feb. 17, 2006.

(51) Int. Cl.
*C07D 403/12* (2006.01)
*A61K 31/506* (2006.01)

(52) U.S. Cl. ........ 514/274; 514/340; 514/374; 544/310; 546/271.4; 548/236

(58) Field of Classification Search .................. 544/310; 546/271.4; 548/236; 514/274, 340, 374
See application file for complete search history.

(56) References Cited

U.S. PATENT DOCUMENTS

| | | | |
|---|---|---|---|
| 6,096,784 A | 8/2000 | Lerner et al. | |
| 6,462,054 B1 | 10/2002 | Boger | |

FOREIGN PATENT DOCUMENTS

| | | | |
|---|---|---|---|
| WO | WO 96/09817 | 9/1994 | |
| WO | WO 97/49667 | 6/1996 | |
| WO | WO 99/26584 | 11/1997 | |
| WO | WO 02/87569 | 4/2001 | |
| WO | WO 2004/033652 | * 4/2004 | |

OTHER PUBLICATIONS

Bundgaard, Design of Prodrugs: Introduction, p. 1, 1985.*
Silverman, Prodrugs and Drug Delivery Systems, The Organic Chemistry of Drug Design and Drug Action, pp. 352-400, 1992.*
Layzer, Degenerative Diseases of the Nervous System, Cecil Textbook of Medicine, 20$^{th}$ Edition, vol. 2, pp. 2050-2057, 1996.*
Damasio, Alzheimer's Disease and related Dementias, Cecil Textbook of Medicine, 20$^{th}$ Edition, vol. 2, pp. 1992-1996, 1996.*
Seierstad et al., Discovery and Development of Fatty Acid Amide Hydrolase (FAAH) Inhibitors, Journal of Medicinal Chemistry, vol. 51, No. 23, pp. 7327-7343, 2008.*
Simone, Oncology: Introduction, Cecil Textbook of Medicine, 20$^{th}$ Edition, pp. 1004-1010, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Berge, et al., "Pharmaceutical Salts", *J. Pharm. Sci. 66*: 1-19 (1977).
Devane, et al., "Isolation and Structure of a Brain Constituent That Binds to the Cannabinoid Receptor", *Science 258*: 1946-1949 (1992).
Cravatt, et al., "Chemical Characterization of a Family of Brain Lipids That Induce Sleep", *Science 268*: 1506-1509 (1995).
Conde-Frieboes, et al., "Activated Ketones as Inhibitors of Intracellular $Ca^{+2}$-Dependent and $Ca^{+2}$-Independent Phospholipase A2", *J. Am. Chem. Soc. 118*: 5519-5525 (1996).
Patterson, et al., "Inhibition of Oleamide Hydrolase Catalyzed Hydrolysis of the Endogenous Sleep-Inducing Lipid cis-9-Octadecenamide", *J. Am. Chem. Soc. 118*: 5938-5945 (1996).
Cravatt, et al., "Molecular characterization of an enzyme that degrades neuromodulatory fatty-acid amides", *Nature 384*: 83-87 (1996).
Patricelli, et al., "An Endogenous Sleep-Inducing Compound is a Novel Competitive Inhibitor of Fatty Acid Amide Hydrolase", *Bioorg. Med. Chem. Lett. 8*: 613-618 (1998).
Baker, et al., "Cannabinoids control spasticity and tremor in a multiple sclerosis model", *Nature 404*: 84-87 (2000).
Boger, et al., "Exceptionally potent inhibitors of fatty acid amide hydrolase: The enzyme responsible for degradation of endogenous oleamide and anandamide", *Proc. Natl. Acad. Sci. USA 97*: 5044-5049 (2000).
Baker, et al., "Endocannabinoids control spasticity in a multiple sclerosis model", *FASEB J. 15*: 300-302 (2001).
Robson, et al., "Therapeutic aspects of cannabis and cannabinoids", *Br. J. Psychiatry 178*: 107-115 (2001).
Mendelson, et al., "The Hypnotic Actions of the Fatty Acid Amide, Oleamide", *Neuropsychopharmacology 25*: S36-S39 (2001).
Cravatt, et al., "Supersensitivity to anandamide and enhanced endogenous cannabinoid signaling in mice lacking fatty acid amide hydrolase", *Proc. Natl. Acad. Sci. USA 98*: 9371-9376 (2001).
Ueda, et al., "Purification and Characterization of an Acid Amidase Selective for N-Palmitoylethanolamine, a Putative Endogenous Anti-inflammatory Substance", *J. Biol. Chem. 276*: 35552-35557 (2001).
Jefferis, et al., "Target neuron prespecification in the olfactory map of Drosophila", *Nature 414*: 204-208 (2001).
Kirkham, et al., "Endocannabinoid levels in rat limbic forebrain and hypothalamus in relation to fasting, feeding and satiation: stimulation of eating by 2-arachidonoyl glycerol", *Br. J. Pharmacol. 136*: 550-557 (2002).
Lambert, et al., "The Palmitoylethanolamide Family: A New Class of Anti-Inflammatory Agents", *Curr. Med. Chem. 9*: 663-674 (2002).
Kathuria, et al., "Modulation of anxiety through blockade of anandamide hydrolysis", *Nature Med. 9*: 76-81 (2003).
Piomelli, D., "The Molecular Logic of Endocannabinoid Signalling", *Nature Rev. 4*: 873-884 (2003).
Svendsen, et al., "Does the cannabinoid dronabinol reduce central pain in multiple sclerosis? Randomised double blind placebo controlled crossover trial", *Br. Med. J. 329*: 253-260 (2004) [BMJ, doi:10.1136/bmj.38149.566979.AE].
Boger, et al., "Discovery of a Potent, Selective, and Efficacious Class of Reversible α-Ketoheterocycle Inhibitors of Fatty Acid Amide Hydrolase Effective as Analgesics", *J. Med. Chem. 48*: 1849-1856 (2005).

* cited by examiner

*Primary Examiner* — Deepak Rao
(74) *Attorney, Agent, or Firm* — Schwegman, Lundberg & Woessner P.A.

(57) ABSTRACT

Certain oxazole ketone compounds are useful as FAAH inhibitors. Such compounds may be used in pharmaceutical compositions and methods for the treatment of disease states, disorders, and conditions mediated by fatty acid amide hydrolase (FAAH) activity. Thus, the compounds may be administered to treat anxiety, pain, inflammation, sleep disorders, eating disorders, or movement disorders (such as MS).

15 Claims, No Drawings

OXAZOLE KETONES AS MODULATORS OF FATTY ACID AMIDE HYDROLASE

This application claims the benefit of U.S. Provisional Application No. 60/774,322 filed Feb. 17, 2006.

This invention was made with United States Government support under Contract No. DA 15648 by the National Institutes of Health. The United States Government has certain rights in the invention.

FIELD OF INVENTION

The present invention relates to certain 2-keto-oxazole compounds, pharmaceutical compositions containing them, and methods of using them for the treatment of disease states, disorders, and conditions mediated by fatty acid amide hydrolase (FAAH) activity.

BACKGROUND

Medicinal benefits have been attributed to the cannabis plant for centuries. The primary bioactive constituent of cannabis is $\Delta^9$-tetrahydro-cannabinol (THC). The discovery of THC eventually led to the identification of two endogenous cannabinoid receptors responsible for its pharmacological actions, namely $CB_1$ and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4(11), 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9(6), 663).

Small-molecule inhibitors of FAAH should elevate the concentrations of these endogenous signaling lipids and thereby produce their associated beneficial pharmacological effects. There have been some reports of the effects of various FAAH inhibitors in pre-clinical models.

In particular, two carbamate-based inhibitors of FAAH were reported to have analgesic properties in animal models. In rats, BMS-1 (see WO 02/087569), which has the structure shown below, was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9(1), 76). The sulfonylfluoride AM374 was also shown to significantly reduce spasticity in chronic relapsing experimental autoimmune encephalomyelitis (CREAE) mice, an animal model of multiple sclerosis (Baker, *FASEB J.* 2001, 15(2), 300).

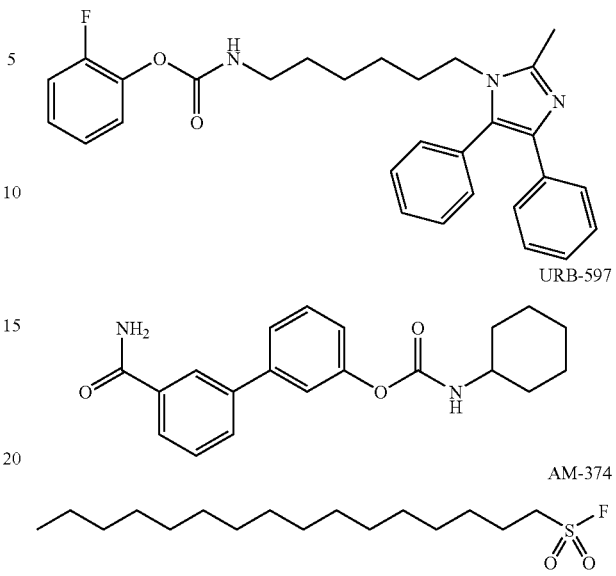

In addition, the oxazolopyridine ketone OL-135 is reported to be a potent inhibitor of FAAH, and has been reported to have analgesic activity in both the hot plate and tail emersion tests of thermal nociception in rats (WO 04/033652).

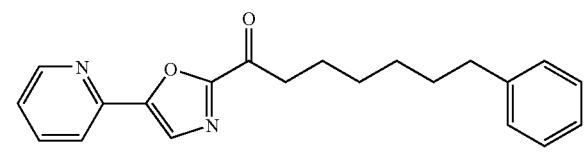

Results of research on the effects of certain exogenous cannabinoids has elucidated that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDS who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is reported to be developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain with CT-3 was reported as being initiated in Germany in May 2002.

A number of individuals with multiple sclerosis have claimed a benefit from cannabis for both disease-related pain and spasticity, with support from small controlled trials (Svendsen, *Br. Med. J.* 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials have been undertaken in multiple sclerosis and spinal cord injury patients with a narrow ratio mixture of tetrahydrocannabinol/cannabidiol (THC/CBD).

Reports of small-scale controlled trials have been conducted to investigate other potential commercial uses of cannabinoids have been made. Trials in volunteers have been reported that confirmed that oral, injected and smoked cannabinoids produced dose-related reductions in intraocular pressure (IOP) and therefore may relieve glaucoma symptoms. Ophthalmologists have prescribed cannabis for patients with glaucoma in whom other drugs have failed to adequately control intraocular pressure (Robson, 2001).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH −/− mice show reduced responses in tests of nociception, but did not show catalepsy, hypothermia, or increased feeding behavior (Cravatt, *Proc. Natl. Acad. Sci. USA* 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003).

In addition to the effects of a FAAH inhibitor on AEA and other endocannabinoids, inhibitors of FAAH's catabolism of other lipid mediators may be used in treating other therapeutic indications. For example, PEA has demonstrated biological effects in animal models of inflammation, immunosuppression, analgesia, and neuroprotection (Ueda, *J. Biol. Chem.* 2001, 276(38), 35552). Oleamide, another substrate of FAAH, induces sleep (Boger, *Proc. Natl. Acad. Sci. USA* 2000, 97(10), 5044; Mendelson, *Neuropsychopharmacology* 2001, 25, S36).

Thus, there is evidence that small-molecule FAAH inhibitors may be useful in treating pain of various etiologies, anxiety, multiple sclerosis and other movement disorders, nausea/emesis, eating disorders, epilepsy, glaucoma, inflammation, immunosuppression, neuroprotection, and sleep disorders, and potentially with fewer side effects than treatment with an exogenous cannabinoid. Various small-molecule FAAH modulators have been reported, e.g., in WO 04/033652, U.S. Pat. No. 6,462,054, U.S. Pat. No. 6,096,784, WO 99/26584, WO 97/49667, and WO 96/09817. However, there is still a need for other potent FAAH modulators with desirable pharmacological properties.

SUMMARY

Certain 2-keto-oxazole derivatives have now been found to have FAAH-modulating activity. More particularly, in one general aspect the invention relates to compounds of the following Formula (I):

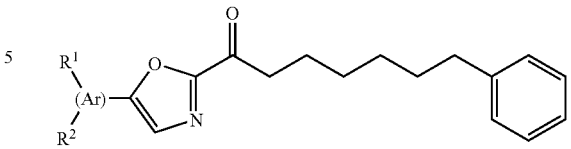

In Formula (I), Ar is a 5- or 6-membered aryl or heteroaryl ring having a carbon as its point of attachment to the oxazole; $R^1$ is independently —$C_{1-6}$alkyl, —$C_{3-6}$cycloalkyl, —$CF_3$, —CN, —C(O)$C_{1-4}$alkyl optionally substituted with one, two, or three fluoro substituents, —$CO_2C_{1-4}$alkyl, —$CO_2H$, —C(O)N($R^a$)$R^b$, —OH, —$OC_{1-6}$alkyl, halo, —$NO_2$, —$NR^aR^b$, —N($R^a$)$COR^b$, —N($R^a$)$SO_2R^b$, $SO_2N(R^a)R^b$, or $S(O)_{0-2}R^a$; where $R^a$ and $R^b$ are each independently —H, —$C_{1-6}$alkyl, or —$C_{3-6}$cycloalkyl; and $R^2$ is independently —H, —$C_{1-6}$alkyl, —$C_{3-6}$cycloalkyl, —$CF_3$, —CN, —C(O)$C_{1-4}$alkyl optionally substituted with one, two, or three fluoro substituents, —$CO_2C_{1-4}$alkyl, —$CO_2H$, —C(O)N($R^c$)$R^d$, —OH, —$OC_{1-6}$alkyl, halo, —$NO_2$, —$NR^cR^d$, —N($R^c$)$COR^d$, —N($R^c$)$SO_2R^d$, $SO_2N(R^c)R^d$, or $S(O)_{0-2}R^c$; where $R^c$ and $R^d$ are each independently —H, —$C_{1-6}$alkyl, or —$C_{3-6}$cycloalkyl; or a pharmaceutically acceptable salt, pharmaceutically acceptable prodrug, or pharmaceutically active metabolite of said compound.

In preferred embodiments, the compound of Formula (I) is a compound specifically described or exemplified in the detailed description below.

In a further general aspect, the invention relates to pharmaceutical compositions each comprising: (a) an effective amount of an agent selected from compounds of Formula (I) and pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition mediated by FAAH activity, comprising administering to the subject in need of such treatment an effective amount of a compound of Formula (I), or a pharmaceutically acceptable salt, pharmaceutically acceptable prodrug, or pharmaceutically active metabolite of such compound.

In certain preferred embodiments of the inventive method, the disease, disorder, or medical condition is selected from: anxiety, pain, sleep disorders, eating disorders, inflammation, multiple sclerosis and other movement disorders, HIV wasting syndrome, closed head injury, stroke, Alzheimer's disease, epilepsy, Tourette's syndrome, Niemann-Pick disease, Parkinson's disease, Huntington's chorea, optic neuritis, autoimmune uveitis, symptoms of drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, autoimmune diabetes, intractable pruritis, and neuroinflammation.

Additional embodiments, features, and advantages of the invention will be apparent from the appended claims, which are incorporated into this summary by reference, as well as from the following detailed description.

Detailed Description of Invention and its Preferred Embodiments

The invention may be more fully appreciated by reference to the following description, including the following glossary of terms and the concluding examples. For the sake of brevity, the disclosures of the publications cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Exemplary alkyl groups include methyl (Me, which also may be structurally depicted by l), ethyl (Et), n-propyl, isopropyl, butyl, isobutyl, sec-butyl, tert-butyl (tBu), pentyl, isopentyl, tert-pentyl, hexyl, isohexyl, and the like.

The term "aryl" refers to a monocyclic, fused bicyclic, or fused polycyclic, aromatic carbocycle (ring structure having ring atoms that are all carbon) having from 3 to 12 ring atoms per carbocycle. (Carbon atoms in aryl groups are sp$^2$ hybridized.) Illustrative examples of aryl groups include phenyl, naphthyl, anthracenyl, phenanthrenyl, and the like.

The term "heteroaryl" refers to a monocyclic, fused bicyclic, or fused polycyclic aromatic heterocycle (ring structure having ring atoms selected from carbon atoms as well as nitrogen, oxygen, and sulfur heteroatoms) having from 3 to 12 ring atoms per heterocycle. Illustrative examples of heteroaryl groups include the following moieties:

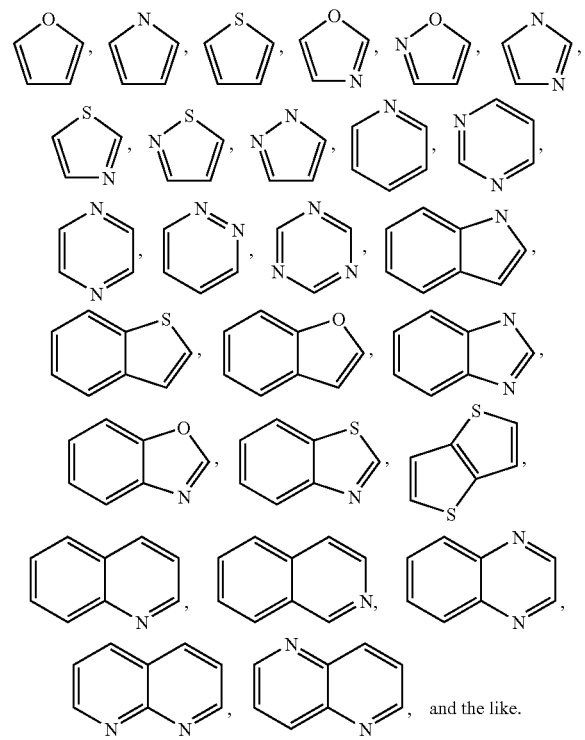

, and the like.

The term "cycloalkyl" refers to a saturated or partially saturated, monocyclic, fused polycyclic, or spiro polycyclic, carbocycle having from 3 to 12 ring atoms per carbocycle. Illustrative examples of cycloalkyl groups include the following moieties:

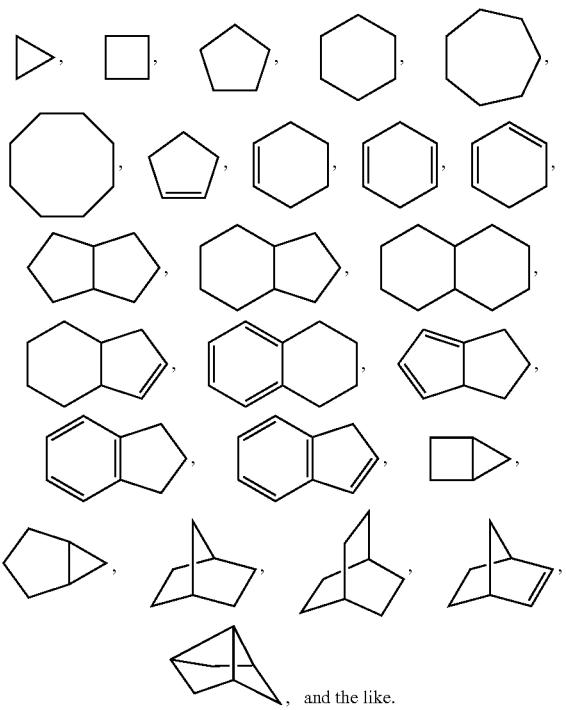

, and the like.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof.

Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, sulfur, phosphorous, fluorine, and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Various isotopically labeled compounds of the present invention, for example those into which radioactive isotopes such as $^3$H, $^{11}$C, and $^{14}$C are incorporated. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of the invention, Ar is selected from the group consisting of phenyl, pyridyl, pyridazinyl, pyrimidinyl, pyrimidine-dione, pyrazinyl, thiophenyl, furanyl, imidazolyl, oxazolyl, and tetrazolyl. More preferably, Ar is selected from the group consisting of 3-($R^1$)-phenyl, 3-($R^1$)-2-pyridyl, 4-($R^1$)-2-pyridyl, 5-($R^1$)-2-pyridyl, 6-($R^1$)-2-pyridyl, 5-($R^1$)-2-furanyl, 5-($R^1$)-2-thiophenyl, 1-($R^1$)-1H-2-imidazolyl, and 1-($R^1$)-1H-5-tetrazolyl. Preferably, $R^1$ is selected from the group consisting of —CH$_3$, —CF$_3$, —CN, —C(O)CF$_3$, —CO$_2$CH$_3$, —CO$_2$H, —C(O)NH$_2$, —OH, —OCH$_3$, fluoro, —NO$_2$, —NH$_2$, and —SO$_2$NH$_2$. Preferably, $R^2$ is —H.

The invention includes also pharmaceutically acceptable salts of the compounds represented by Formula (I), such as of those described above. Pharmaceutically acceptable salts of the specific compounds exemplified are especially preferred.

A "pharmaceutically acceptable salt" is intended to mean a salt of a free acid or base of a compound represented by Formula (I) that is not toxic, biologically intolerable, or otherwise biologically undesirable. See, generally, S. M. Berge, et al., "Pharmaceutical Salts", J. Pharm. Sci., 1977, 66:1-19, and *Handbook of Pharmaceutical Salts, Propertions, Selection, and Use*; Stahl, P. H., Wermuth, C. G., Eds.; Wiley-VCH and VHCA: Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Exemplary pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or the like.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to treatment methods employing pharmaceutically acceptable prodrugs of the compounds of Formula (I). The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is not toxic, biologically intolerable, or otherwise biologically unsuitable for administration to the subject. Conventional procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Exemplary amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Preferred amides are derived from ammonia, $C_{1-3}$alkyl primary amines, and di($C_{1-2}$alkyl) amines. Exemplary esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

Pharmaceutically active metabolites may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formula (I) and their pharmaceutically acceptable salts, pharmaceutically acceptable prodrugs, and pharmaceutically active metabolites (collectively, "agents") of the present invention are useful as FAAH inhibitors in the methods of the invention. The agents may be used in the inventive methods for the treatment or prevention of medical conditions, diseases, or disorders mediated through inhibition or modulation of FAAH, such as those described herein. Agents according to the invention may therefore be used as an analgesic, neuroprotectant, sedative, appetite stimulant, or contraceptive.

Exemplary medical conditions, diseases, and disorders include anxiety, pain, sleep disorders, eating disorders, inflammation, multiple sclerosis and other movement disorders, HIV wasting syndrome, closed head injury, stroke, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, or cerebral vasospasm.

Thus, the pharmaceutical agents may be used to treat subjects diagnosed with or suffering from a disease, disorder, or condition mediated through FAAH activity. The term "treat" or "treating" as used herein is intended to refer to administration of an agent or composition of the invention to a subject for the purpose of effecting a therapeutic or prophylactic benefit through modulation of FAAH activity. Treating includes reversing, ameliorating, alleviating, inhibiting the progress of, lessening the severity of, or preventing a disease, disorder, or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize, or up-regulate FAAH expression or activity.

Accordingly, the invention relates to methods of using the pharmaceutical agents described herein to treat subjects diagnosed with or suffering from a disease, disorder, or condition mediated through FAAH activity, such as: anxiety, pain, sleep disorders, eating disorders, inflammation, or movement disorders (e.g., multiple sclerosis).

Symptoms or disease states are intended to be included within the scope of "medical conditions, disorders, or diseases." For example, pain may be associated with various diseases, disorders, or conditions, and may include various etiologies. Illustrative types of pain treatable with a FAAH-modulating agent according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In a treatment method according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment.

Effective amounts or doses of the agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of agent per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active compounds in the treatment of the above conditions. The additional compounds may be coadministered separately with an agent of Formula (I) or included with such an agent as an additional active ingredient in a pharmaceutical composition according to the invention. In an exemplary embodiment, additional active compounds are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention. In one illustrative embodiment, a composition according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, and aspirin.

The agents of the invention are used, alone or in combination with one or more other active ingredients, to formulate pharmaceutical compositions of the invention. A pharmaceutical composition of the invention comprises: (a) an effective amount of a pharmaceutical agent in accordance with the invention; and (b) a pharmaceutically acceptable excipient.

A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the pharmaceutical agents may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The agents of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Exemplary agents useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

SCHEME A

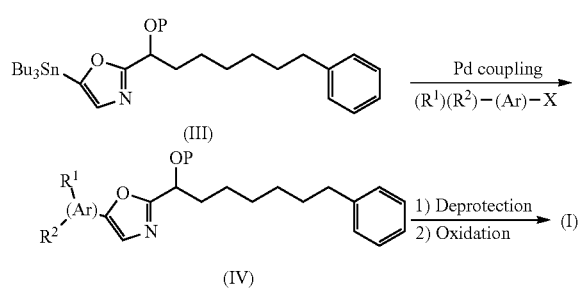

Referring to Scheme A, stannanes of formula (III), where P is a suitable hydroxyl protecting group, are prepared as previously described (Boger, *J. Med. Chem.* 2005, 48, 1849). Stannanes (III) are coupled with various aryl or heteroaryl halides using Stille coupling procedures. Preferred conditions utilize $Pd(PPh_3)_4$ or $Pd(P(t-Bu)_3)_2$ as the catalyst. Compounds of formula (IV) are then deprotected (for example, where P is a silyl protecting group, with a silyl deprotecting agent such as TBAF) and oxidized to compounds of Formula (I) using oxidizing agents such as Dess-Martin periodinane or TPAP/NMO.

SCHEME B

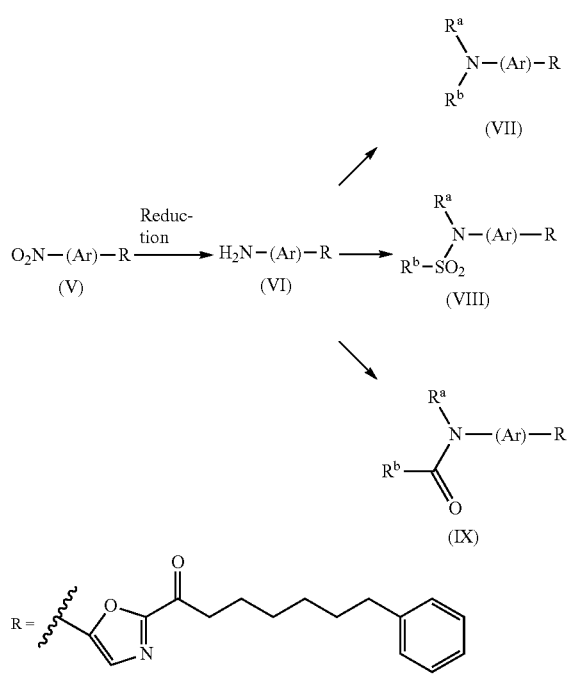

Referring to Scheme B, compounds of formula (V) may be obtained according to the methods shown in Scheme A. The nitro group may be reduced to an amino group (formula (VI)) using standard nitro reduction methods, such as exposure to $SnCl_2$ or by hydrogenation in the presence of a Pd catalyst. Amines (VI) may be alkylated via alkylation or reductive amination protocols to form amines (VII). Amines (VI) may be alternatively sulfonylated with the appropriately substituted sulfonyl chlorides to form compounds of formula (VIII). Reaction of amines (VI) with suitably substituted acid chlorides or via peptide coupling with appropriate acids (e.g. in the presence of HOAt/EDCl) generate amides (IX). Installation of the $R^a$ substituent may be accomplished before (via alkylation or reductive amination) or after (via alkylation) the sulfonylation/acylation step. One skilled in the art will recognize that Formula (I) includes compounds of formulae (VI), (VII), (VIII), and (IX).

SCHEME C

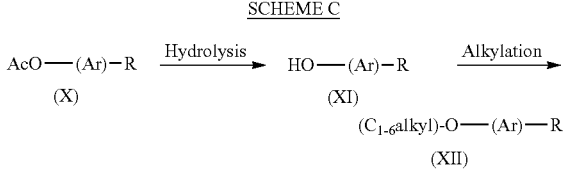

Referring to Scheme C, acetates of formula (X), where R is defined as in Scheme B, may be obtained according to the methods shown in Scheme A. Deprotection of the acetate group, using, for example, a base such as LiOH or NaOMe, gives the corresponding alcohols (XI). These alcohols may in turn be converted to ethers of formula (XII) by treatment with an appropriate alkyl halide in the presence of a base, or with an appropriate alcohol under Mitsunobu conditions (for example, $PPh_3$/DEAD). One skilled in the art will recognize that Formula (I) includes compounds of formulae (XI) and (XII).

SCHEME D

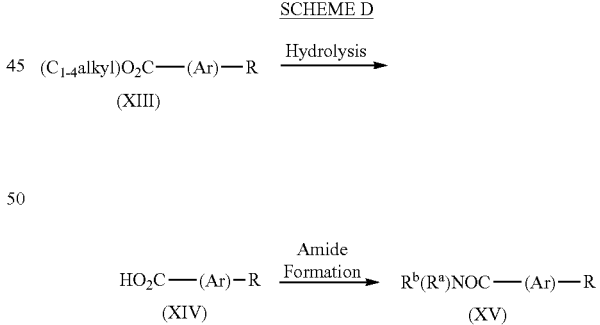

Referring to Scheme D, esters of formula (XIII), where R is defined as in Scheme B, and prepared according to Scheme A, may be hydrolyzed to acids (XIV) using a base such as LiOH. Acids (XIV) may be converted to their corresponding amides (XV) by reaction with a suitable amine under peptide coupling conditions (e.g. HOAt/EDCl). One skilled in the art will recognize that Formula (I) includes compounds of formulae (XIII), (XIV), and (XV).

One skilled in the art will recognize that transformations depicted for $R^1$ may analogously be performed for $R^2$.

SCHEME E

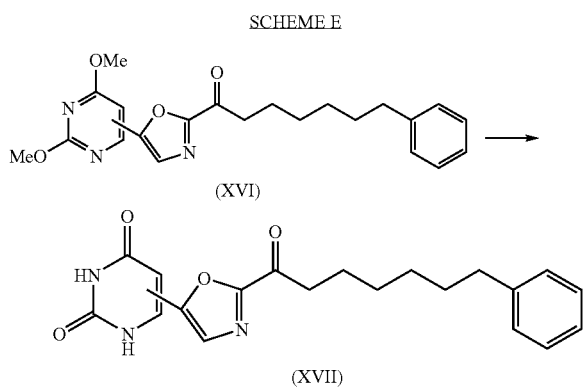

Referring to Scheme E, pyrimidines (XVI), prepared according to Scheme A, may be converted to uracils (XVII) by treatment of a demethylating agent such as TMSI. One skilled in the art will recognize that Formula (I) includes compounds of formulae (XVI) and (XVII).

The following examples are provided to further illustrate the invention and various preferred embodiments.

EXAMPLES

Chemistry:

In obtaining the characterization data described in the examples below, the following analytical protocols were followed as indicated.

NMR spectra were obtained on Bruker model DRX spectrometers. The format of the $^1$H NMR data below is: chemical shift in ppm downfield of the tetramethylsilane reference (multiplicity, coupling constant J in Hz, integration).

Silica gel was used for all chromatographic purification unless otherwise noted. Where solutions were "concentrated", they were concentrated using a rotary evaporator under reduced pressure. Unless otherwise specified, reaction solutions were stirred at room temperature (rt) under a nitrogen atmosphere.

Mass spectra were obtained on an Agilent series 1100 MSD using electrospray ionization (ESI) in either positive or negative modes as indicated. Calculated mass (mass calcd.) corresponds to the exact mass.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

Reversed-phase HPLC was performed on a Hewlett Packard HPLC Series 1100, with a Phenomenex Luna C18 (5 μm, 4.6×150 mm) column. Detection was done at λ=230, 254 and 280 nm. The flow rate was 1 mL/min. The gradient was 10 to 99% acetonitrile/water (0.05% trifluoroacetic acid) over 5.0 min.

General Procedure A. 2-(1-(tert-Butyldimethylsilyloxy)-7-phenylheptyl)-5-(tributylstannyl)oxazole (1 equiv), Pd(PPh$_3$)$_4$ (0.1 equiv), and aryl halide (2 equiv) were dissolved in anhydrous 1,4-dioxane (8 mL) and the mixture was warmed to reflux for 24 h under argon. The mixture was diluted with EtOAc, washed with saturated aqueous NaCl and dried over Na$_2$SO$_4$. Evaporation in vacuo yielded the crude coupling product that was purified by flash chromatography (SiO$_2$).

General Procedure B. 2-(1-(tert-Butyldimethylsilyloxy)-7-phenylheptyl)-5-(tributylstannyl)oxazole (1 equiv), Pd(P(tBu)$_3$)$_2$ (0.1 equiv), CsF (2.2 equiv) and aryl halide (2 equiv) were dissolved in anhydrous 1,4-dioxane (2 mL) and the mixture was warmed at 100° C. in a sealed tube and stirred for 24 h. The mixture was diluted with EtOAc, washed with saturated aqueous NaCl and dried over Na$_2$SO$_4$. Evaporation in vacuo yielded the crude coupling product that was purified by flash chromatography (SiO$_2$).

General Procedure C. The TBS ether (1 equiv) was dissolved in THF (3 mL), treated with Bu$_4$NF (1 M in THF, 1.2 equiv) and stirred at room temperature for 2 h under argon. The reaction mixture was diluted with EtOAc, washed with saturated aqueous NaCl and dried over Na$_2$SO$_4$. Evaporation in vacuo yielded the crude alcohol that was filtered through a short silica gel pad. The silica gel pad was washed with 10% EtOAc/hexanes followed by 60% EtOAc/hexanes to afford the alcohol which required no further purification. The alcohol (1 equiv) was dissolved in CH$_2$Cl$_2$ (3 mL) or THF (3 mL) and Dess-Martin periodinane (1.5 equiv) was added. The mixture was stirred at room temperature for 2 h before silica gel was added and the reaction mixture was evaporated in vacuo to afford the crude ketone absorbed on silica gel. This mixture was subsequently purified by flash chromatography (SiO$_2$) yielding the pure α-ketoheterocycle.

General Procedure D. The TBS ether (1 equiv) was dissolved in THF (3 mL), treated with Bu$_4$NF (1 M in THF, 1.2 equiv) and stirred at room temperature for 2 h under argon. The reaction mixture was diluted with EtOAc, washed with saturated aqueous NaCl and dried over Na$_2$SO$_4$. Evaporation in vacuo yielded the crude alcohol that was filtered through a short silica gel pad. The silica gel pad was washed with 10% EtOAc/hexanes followed by 60% EtOAc/hexanes to afford the alcohol which required no further purification. The alcohol (1 equiv) was dissolved in CH$_2$Cl$_2$ (3 mL) and tetrapropylammonium perruthenate (TPAP, 0.2 equiv), N-morpholine oxide (NMO, 1.5 equiv) and 4 A molecular sieves (1.5× weight of alcohol) were added. The mixture was stirred at room temperature for 5 h before it was filtered through a pad of diatomaceous earth. This crude ketone was subsequently purified by flash chromatography (SiO$_2$) yielding the pure α-ketoheterocycle.

General Procedure E. The ester (1 equiv) was dissolved in a mixture of 3:2 THF/H$_2$O (2 mL:1.3 mL) and LiOH (3 equiv) was added. The reaction mixture stirred for 2 h at room temperature before the mixture was made acidic with the addition of aqueous 1 N HCl. The solution was diluted with EtOAc and the organic layer was separated from the aqueous layer. The aqueous layer was extracted with EtOAc (3×). The combined organic extracts were washed with saturated aqueous NaCl and dried over Na$_2$SO$_4$. Evaporation in vacuo yielded the crude acid that was purified by chromatography (SiO$_2$).

General Procedure F. The nitro compound (1 equiv) was dissolved in EtOAc (2 mL) and 10% Pd/C (0.1 equiv) was added. The reaction mixture was stirred at room temperature under H$_2$ (1 atm) for 4 h before it was filtered through a pad of diatomaceous earth. Evaporation in vacuo yielded the crude aniline that was purified by chromatography (SiO$_2$).

General Procedure G. 2-(7-Phenylheptanoyl)oxazole-5-carboxylic acid (1 equiv), EDCl (2 equiv) and HOAt (2 equiv) were dissolved in DMF (1 mL). The reaction mixture was cooled to 0° C. and stirred for 10 min before the amine (1.5 equiv) was added. The reaction mixture was stirred for 16 h under argon, diluted with H$_2$O and made acidic with the addition of aqueous 2 N HCl. The solution was extracted with ether (3×) and the ether layers were combined, washed with saturated aqueous NaCl and dried over Na₂SO₄. Evaporation in vacuo yielded the crude amide that was purified by chromatography (SiO₂).

General Procedure H. The pyrimdine (1 equiv) and NaI (4 equiv) were dissolved in MeCN (3 mL) before TMSCl (4 equiv) was added. The reaction was stirred for 16 h at room temperature under argon before it was diluted with EtOAc, washed with saturated aqueous Na₂S₂O₃ and washed with saturated aqueous NaCl. Evaporation in vacuo yielded the crude uracil that was purified by flash chromatography (SiO₂).

General Procedure I. The TBS ether (1 equiv) was dissolved in THF (3 mL), treated with Bu₄NF (1 M in THF, 1.2 equiv) and the mixture was stirred at room temperature for 2 h under argon. The reaction mixture was diluted with EtOAc, washed with saturated aqueous NaCl and dried over Na₂SO₄. Evaporation in vacuo yielded the crude alcohol that was purified by flash chromatography (SiO₂).

General Procedure J. The ester (1 equiv) was dissolved in methanolic ammonia (1 mL) and stirred for 2 h at room temperature under argon. Evaporation in vacuo yielded the crude alcohol that was purified by chromatography (SiO₂).

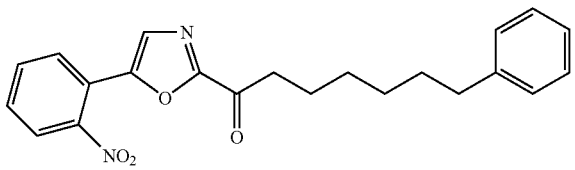

Example 1

1-(5-(2-Nitrophenyl)oxazol-2-yl)-7-phenylheptan-1-one

Step 1; 2-(1-(tert-Butyldimethylsilyloxy)-7-phenylheptyl)-5-(2-nitrophenyl)oxazole. The title compound was prepared from 2-(1-(tert-butyldimethylsilyloxy)-7-phenylheptyl)-5-(tributylstannyl)oxazole (75 mg, 0.113 mmol) and 1-iodo-2-nitrobenzene following General Procedure A. Flash chromatography (3-10% EtOAc/hexanes) yielded the title compound as a yellow oil (58 mg, 97%): ¹H NMR (CDCl₃, 300 MHz) δ 7.82 (dd, 1 H, J=9.2, 6.3 Hz), 7.70 (dd, 1H, J=9.3, 6.0 Hz), 7.67-7.64 (m, 1H), 7.51-7.49 (m, 1H), 7.32-7.25 (m, 3H), 7.19-7.16 (m, 3H), 4.82 (t, 1H, J=6.7 Hz), 2.60 (t, 2H, J=7.5 Hz), 1.88-1.86 (m, 2H), 1.64-1.60 (m, 2H), 1.35-1.26 (m, 6H), 0.90 (s, 9H), 0.10 (s, 3H), 0.00 (s, 3H); ¹³C NMR (CDCl₃, 75 MHz) δ 171.5, 152.5, 151.1, 148.0, 137.6, 134.6, 134.5, 133.6, 133.4, 131.3, 130.7, 129.6, 127.1, 73.8, 41.6, 41.1, 36.6, 34.3, 34.3, 30.9, 30.1, 23.4, 0.2, 0.0.

Step 2. The title compound was prepared from 2-(1-(tert-butyldimethylsilyloxy)-7-phenylheptyl)-5-(2-nitrophenyl)oxazole (54 mg, 0.109 mmol) following General Procedure C. Flash chromatography (20% EtOAc/hexanes) yielded the title compound as a light yellow solid (29 mg, 71%):

¹H NMR (CDCl₃, 400 MHz) δ 7.86 (d, 1H, J=8.8 Hz), 7.75 (dd, 1H, J=9.2, 6.4 Hz), 7.65-7.62 (m, 1H), 7.55-7.51 (m, 1H), 7.44 (s, 1H), 7.21-7.18 (m, 2H), 7.11-7.09 (m, 3H), 3.00 (t, 2H, J=7.6 Hz), 2.53 (t, 2H, J=7.6 Hz), 1.71-1.68 (m, 2H), 1.58-1.54 (m, 2H), 1.36-1.32 (m, 4H); ¹³C NMR (CDCl₃, 100 MHz). δ 188.4, 157.9, 148.8, 147.9, 142.9, 133.1, 131.0, 130.6, 128.6, 128.4, 128.2, 125.8, 124.9, 121.2, 39.4, 36.1, 31.5, 29.2, 29.2, 24.0; MALDI-FTMS m/z 379.1651 (M+H⁺, C₂₂H₂₃N₂O₄, requires 379.1652).

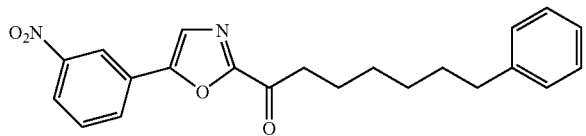

Example 2

1-(5-(3-Nitrophenyl)oxazol-2-yl)-7-phenylheptan-1-one

Step 1; 2-(1-(tert-Butyldimethylsilyloxy)-7-phenylheptyl)-5-(3-nitrophenyl)oxazole. The title compound was prepared from 2-(1-(tert-butyldimethylsilyloxy)-7-phenylheptyl)-5-(tributylstannyl)oxazole (191 mg, 0.288 mmol) and 1-iodo-3-nitrobenzene following General Procedure A. Flash chromatography (5-10% EtOAc/hexanes) yielded the title compound as a yellow oil (128 mg, 90%): ¹H NMR (CDCl₃, 500 MHz) δ 8.57-8.56 (m, 1H), 8.26-8.24 (m, 1H), 8.03-8.02 (m, 1H), 7.69 (t, 1H, J=16 Hz), 7.51 (s, 1H), 7.36-7.33 (m, 2H), 7.26-7.23 (m, 3H), 4.94 (t, 1H, J=6.0 Hz), 2.67 (t, 2H, J=7.5 Hz), 2.05-1.96 (m, 2H), 1.72-1.66 (m, 2H), 1.57-1.44 (m, 6H), 0.99 (s, 9H), 0.19 (s, 3H), 0.09 (s, 3H); ¹³C NMR (CDCl₃, 125 MHz) δ 166.4, 149.3, 149.2, 143.2, 130.5, 130.1, 130.0, 128.8, 128.6, 126.0, 124.2, 123.2, 119.4, 69.1, 36.8, 36.3, 31.8, 29.6, 26.1, 26.1, 25.5, 18.6, −4.5, −4.6.

Step 2. The title compound was prepared from 2-(1-(tert-butyldimethylsilyloxy)-7-phenylheptyl)-5-(3-nitrophenyl)oxazole (126 mg, 0.255 mmol) following General Procedure C. Flash chromatography (5-20% EtOAc/hexanes) yielded the title compound as a light yellow solid (75 mg, 77%):

¹H NMR (CDCl₃, 500 MHz) δ 8.67 (s, 1H), 8.35-8.33 (m, 1H), 8.19-8.17 (m, 1H), 7.77-7.74 (m, 2H), 7.36-7.33 (m, 2H), 7.26-7.24 (m, 3H), 3.18 (t, 2H, J=7.5 Hz), 2.69 (t, 2H, J=7.5 Hz), 1.90-1.84 (m, 2H), 1.75-1.69 (m, 2H), 1.54-1.46 (m, 4H); ¹³C NMR (CDCl₃, 125 MHz) δ 188.7, 158.0, 152.0, 149.2, 143.1, 131.1, 130.8, 128.8, 128.8, 127.7, 126.1, 125.8, 124.7, 120.5, 39.6, 36.3, 31.7, 29.4, 29.4, 24.3; MALDI-FTMS m/z 379.1652 (M+H⁺, C₂₂H₂₃N₂O₄, requires 379.1652).

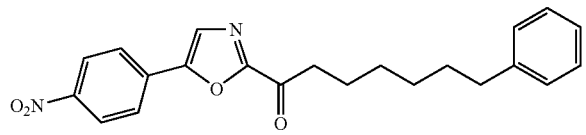

Example 3

1-(5-(4-Nitrophenyl)oxazol-2-yl)-7-phenylheptan-1-one

Step 1; 2-(1-(tert-Butyldimethylsilyloxy)-7-phenylheptyl)-5-(4-nitrophenyl)oxazole. The title compound was prepared from 2-(1-(tert-butyldimethylsilyloxy)-7-phenylheptyl)-5-(tributylstannyl)oxazole (90 mg, 0.136 mmol) and 1-iodo-4-nitrobenzene following General Procedure A. Flash chromatography (5-10% EtOAc/hexanes) yielded the title compound as a yellow oil (67 mg, 100%): ¹H NMR (CDCl₃, 500 MHz) δ 8.28 (d, 2H, J=9.0 Hz), 7.78 (d, 2H, J=9.0 Hz), 7.48 (s, 1H), 7.27-7.24 (m, 2H), 7.17-7.15 (m, 3H), 4.87 (t, 1H, J=6.0 Hz), 2.59 (t, 2H, J=7.8 Hz), 2.00-1.88 (m, 2H), 1.67-1.58 (m, 2H), 1.40-1.34 (m, 6H), 0.91 (s, 9H), 0.11 (s, 3H), 0.01 (s, 3H); $^{13}$C NMR (CDCl$_3$, 125 MHz) δ 166.6, 149.0, 147.1, 142.6, 133.7, 128.3, 128.2, 125.5, 125.1, 124.4, 124.3, 68.6, 36.3, 35.8, 31.3, 29.1, 25.6, 25.6, 25.0, 18.1, −5.0, −5.1.

Step 2. The title compound was prepared from 2-(1-(tert-butyldimethylsilyloxy)-7-phenylheptyl)-5-(4-nitrophenyl)oxazole (65 mg, 0.131 mmol) following General Procedure C. Flash chromatography (5-20% EtOAc/hexanes) yielded the title compound as a light yellow solid (25 mg, 50%):

$^{1}$H NMR (CDCl$_3$, 600 MHz) δ 8.32 (d, 2H, J=8.4 Hz), 7.93 (d, 2H, J=8.4 Hz), 7.69 (s, 1H), 7.27-7.25 (m, 2H), 7.17-7.16 (m, 3H), 3.09 (t, 2H, J=7.2 Hz), 2.60 (t, 2H, J=7.2 Hz), 1.79-1.77 (m, 2H), 1.65-1.62 (m, 2H), 1.44-1.39 (m, 4H); $^{13}$C NMR (CDCl$_3$, 150 MHz) δ 189.2, 158.8, 152.5, 149.0, 143.5, 133.3, 129.2, 129.1, 127.3, 126.7, 126.5, 125.4, 40.0, 36.7, 32.1, 29.8, 29.8, 24.7; MALDI-FTMS m/z 379.1645 (M+H$^+$, C$_{22}$H$_{23}$N$_2$O$_4$, requires 379.1652).

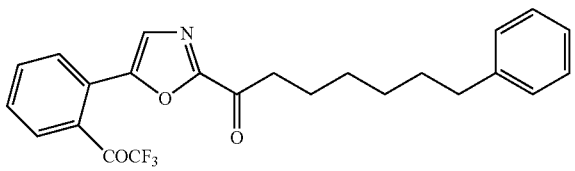

Example 4

7-Phenyl-1-(5-(2-(2,2,2-trifluoroacetyl)phenyl)oxazol-2-yl)heptan-1-one

Step 1; 1-(2-(2-(1-(tert-Butyldimethylsilyloxy)-7-phenylheptyl)oxazol-5-yl)phenyl)-2,2,2-trifluoroethanone. The title compound was prepared from 2-(1-(tert-butyldimethylsilyloxy)-7-phenylheptyl)-5-(tributylstannyl)oxazole (63 mg, 0.095 mmol) and 1-(2-chlorophenyl)-2,2,2-trifluoroethanone following General Procedure B. Flash chromatography (2-10% EtOAc/hexanes) yielded the title compound as a clear oil (43 mg, 83%): $^{1}$H NMR (CDCl$_3$, 600 MHz) δ 7.70-7.64 (m, 3H), 7.51-7.48 (m, 1H), 7.26-7.24 (m, 3H), 7.16-7.15 (m, 3H), 4.79 (t, 1H, J=6.0 Hz), 2.58 (t, 2H, J=7.5 Hz), 1.88-1.81 (m, 2H), 1.61-1.60 (m, 2H), 1.35-1.25 (m, 6H), 0.87 (s, 9H), 0.07 (s, 3H), −0.05 (s, 3H); $^{13}$C NMR (CDCl$_3$, 150 MHz) δ 186.2 (d, J=35 Hz), 167.0, 149.4, 143.7, 133.6, 133.6, 131.1, 129.5, 129.4, 129.3, 129.1, 128.3, 126.4, 125.6, 116.4 (d, J=285 Hz), 69.4, 37.3, 36.8, 32.3, 30.0, 26.5, 26.5, 25.8, 19.0, −4.2, −4.4.

Step 2. The title compound was prepared from 1-(2-(2-(1-(tert-butyldimethylsilyloxy)-7-phenylheptyl)oxazol-5-yl)phenyl)-2,2,2-trifluoroethanone (43 mg, 0.079 mmol) following General Procedure C. Flash chromatography (5-20% EtOAc/hexanes) yielded the title compound as a white solid (26 mg, 76%):

$^{1}$H NMR (CDCl$_3$, 600 MHz) δ 7.80-7.79 (m, 2H), 7.72 (t, 1H, J=7.2 Hz), 7.60 (t, 1H, J=7.2 Hz), 7.47 (s, 1H), 7.28-7.25 (m, 2H), 7.18-7.15 (m, 3H), 3.05 (t, 2H, J=7.8 Hz), 2.60 (t, 2H, J=7.8 Hz), 1.78-1.73 (m, 2H), 1.66-1.61 (m, 2H), 1.42-1.39 (m, 4H); $^{13}$C NMR (CDCl$_3$, 150 MHz) δ 188.9, 184.6 (d, J=36 Hz), 158.6, 152.0, 143.6, 134.2, 131.3, 130.8, 130.8, 130.1, 129.3, 129.1, 129.1, 127.9, 127.7, 126.5, 116.5 (d, J=290 Hz), 40.0, 36.7, 32.2, 29.8, 29.8, 24.6; MALDI-FTMS m/z 430.1626 (M+H$^+$, C$_{24}$H$_{23}$F$_3$NO$_3$, requires 430.1624).

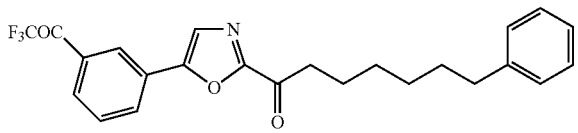

Example 5

7-Phenyl-1-(5-(3-(2,2,2-trifluoroacetyl)phenyl)oxazol-2-yl)heptan-1-one

Step 1; 1-(3-(2-(1-(tert-Butyldimethylsilyloxy)-7-phenylheptyl)oxazol-5-yl)phenyl)-2,2,2-trifluoroethanone. The title compound was prepared from 2-(1-(tert-butyldimethylsilyloxy)-7-phenylheptyl)-5-(tributylstannyl)oxazole (37 mg, 0.056 mmol) and 1-(3-chlorophenyl)-2,2,2-trifluoroethanone following General Procedure B. Flash chromatography (5-20% EtOAc/hexanes) yielded the title compound as a clear oil (26 mg, 87%): $^{1}$H NMR (CDCl$_3$, 600 MHz) δ 8.31 (s, 1H), 8.01-7.94 (m, 2H), 7.61 (t, 1H, J=7.2 Hz), 7.38 (s, 1H), 7.27-7.24 (m, 2H), 7.16-7.14 (m, 3H), 4.84 (t, 1H, J=6.0 Hz), 2.58 (t, 2H, J=7.5 Hz), 1.95-1.88 (m, 2H), 1.64-1.55 (m, 2H), 1.37-1.34 (m, 6H), 0.90 (s, 9H), 0.10 (s, 3H), 0.00 (s, 3H); $^{13}$C NMR (CDCl$_3$, 150 MHz) δ 181.0 (d, J=35 Hz), 166.7, 150.2, 143.6, 131.5, 130.7, 130.4, 130.2, 129.2, 129.1, 129.0, 126.4, 126.2, 124.0, 117.7 (d, J=289 Hz), 69.5, 37.2, 36.8, 32.3, 30.0, 26.6, 26.6, 26.0, 19.1, −4.1, −4.2.

Step 2. The title compound was prepared from 1-(3-(2-(1-(tert-butyldimethylsilyloxy)-7-phenylheptyl)oxazol-5-yl)phenyl)-2,2,2-trifluoroethanone (36 mg, 0.066 mmol) following General Procedure C. Flash chromatography (5-20% EtOAc/hexanes) yielded the title compound as a white solid (17 mg, 61%):

$^{1}$H NMR (CDCl$_3$, 600 MHz) δ 8.41 (s, 1H), 8.12-8.08 (m, 2H), 7.69-7.63 (m, 2H), 7.28-7.26 (m, 2H), 7.17-7.16 (m, 3H), 3.09 (t, 2H, J=7.8 Hz), 2.61 (t, 2H, J=7.8 Hz), 1.79-1.76 (m, 2H), 1.66-1.61 (m, 2H), 1.44-1.39 (m, 4H); $^{13}$C NMR (CDCl$_3$, 150 MHz) δ 189.2, 180.7 (d, J=35 Hz), 158.4, 153.0, 143.5, 132.5, 131.8, 131.6, 130.9, 129.3, 129.1, 127.3, 126.5, 125.9, 117.7 (d, J=289 Hz), 40.0, 36.7, 32.2, 29.9, 29.9, 24.8; MALDI-FTMS m/z 428.1475 (M−H$^-$, C$_{24}$H$_{21}$F$_3$NO$_3$, requires 428.1479).

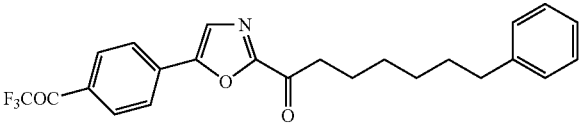

Example 6

7-Phenyl-1-(5-(4-(2,2,2-trifluoroacetyl)phenyl)oxazol-2-yl)heptan-1-one

Step 1; 1-(4-(2-(1-(tert-Butyldimethylsilyloxy)-7-phenylheptyl)oxazol-5-yl)phenyl)-2,2,2-trifluoroethanone. The title compound was prepared from 2-(1-(tert-butyldimethylsilyloxy)-7-phenylheptyl)-5-(tributylstannyl)oxazole (55 mg, 0.083 mmol) and 1-(4-bromophenyl)-2,2,2-trifluoroethanone following General Procedure A. Flash chromatography (5-20% EtOAc/hexanes) yielded the title compound as a white solid (31 mg, 69%): $^{1}$H NMR (CDCl$_3$, 600 MHz) δ

8.13-8.12 (d, 2H, J=7.8 Hz), 7.80-7.79 (d, 2H, J=7.8 Hz), 7.49 (s, 1H), 7.27-7.24 (m, 2H), 7.16-7.15 (m, 3H), 4.86 (t, 1H, J=6.0 Hz), 2.59 (t, 2H, J=7.5 Hz), 1.95-1.91 (m, 2H), 1.61-1.59 (m, 2H), 1.37-1.34 (m, 6H), 0.90 (s, 9H), 0.10 (s, 3H), 0.00 (s, 3H); $^{13}$C NMR (CDCl$_3$, 150 MHz) δ 180.4 (d, J=35 Hz), 167.5, 150.3, 143.6, 135.1, 131.8, 129.9, 129.2, 129.1, 126.5, 126.1, 125.1, 117.6 (d, J=290 Hz), 69.6, 37.3, 36.8, 32.3, 30.0, 36.6, 26.6, 26.0, 19.1, −4.1, −4.2.

Step 2. The title compound was prepared from 1-(4-(2-(1-(tert-butyldimethylsilyloxy)-7-phenylheptyl)oxazol-5-yl)phenyl)-2,2,2-trifluoroethanone (29 mg, 0.053 mmol) following General Procedure C. Flash chromatography (5-20% EtOAc/hexanes) yielded the title compound as a white solid (14 mg, 62%):
$^1$H NMR (CDCl$_3$, 600 MHz) δ 8.16 (d, 2H, J=7.8 Hz), 7.94 (d, 2H, J=7.8 Hz), 7.69 (s, 1H), 7.28-7.25 (m, 2H), 7.17-7.16 (m, 3H), 3.10 (t, 2H, J=7.8 Hz), 2.61 (t, 2H, J=7.8 Hz), 1.79-1.76 (m, 2H), 1.66-1.62 (m, 2H), 1.44-1.39 (m, 4H); $^{13}$C NMR (CDCl$_3$, 150 MHz) δ 189.2, 180.6 (d, J=35 Hz), 152.9, 143.5, 133.7, 131.9, 131.8, 131.2, 129.3, 129.1, 127.4, 126.5, 126.4, 117.7 (d, J=290 Hz), 40.0, 36.7, 32.1, 29.9, 29.9, 24.8; MALDI-FTMS m/z 428.1474 (M−H$^-$, C$_{24}$H$_{21}$F$_3$NO$_3$, requires 428.1479).

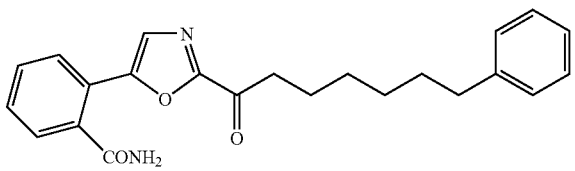

Example 7

2-(2-(7-Phenylheptanoyl)oxazol-5-yl)benzamide

Step 1; 2-(2-(1-(tert-Butyldimethylsilyloxy)-7-phenylheptyl)oxazol-5-yl)benzamide. The title compound was prepared from 2-(1-(tert-butyldimethylsilyloxy)-7-phenylheptyl)-5-(tributylstannyl)oxazole (52 mg, 0.083 mmol) and 2-bromobenzamide following General Procedure A. Flash chromatography (20-40% EtOAc/hexanes) yielded the title compound as a white solid (39 mg, 100%): $^1$H NMR (CDCl$_3$, 600 MHz) δ 7.70 (d, 1H, J=7.8 Hz), 7.60 (s, 1H), 7.51-7.48 (m, 2H), 7.39-7.36 (m, 1H), 7.25-7.23 (m, 2H), 7.16-7.13 (m, 3H), 6.48 (br s, 1H), 6.19 (br s, 1H), 4.88 (t, 1H, J=6.0 Hz), 2.57 (t, 2H, J=7.5 Hz), 1.93-1.87 (m, 2H), 1.59-1.56 (m, 2H), 1.44-1.30 (m, 6H), 0.87 (s, 9H), 0.09 (s, 3H), −0.02 (s, 3H); $^{13}$C NMR (CDCl$_3$, 150 MHz) δ 170.4, 143.6, 137.6, 134.4, 132.5, 131.3, 130.7, 129.7, 129.2, 129.1, 128.6, 128.5, 126.4, 120.1, 69.3, 37.3, 36.8, 32.2, 30.0, 26.6, 26.6, 25.9, 19.0, −4.0, −4.3.

Step 2. The title compound was prepared from 2-(2-(1-(tert-butyldimethylsilyloxy)-7-phenylheptyl)oxazol-5-yl)benzamide (39 mg, 0.079 mmol) following General Procedure C. Flash chromatography (20-70% EtOAc/hexanes) yielded the title compound as a white solid (9 mg, 30%): $^1$H NMR (CDCl$_3$, 500 MHz) δ 7.89 (d, 1H, J=7.5 Hz), 7.68 (s, 1H), 7.63-7.61 (m, 2H), 7.56-7.53 (m, 1H), 7.36-7.34 (m, 2H), 7.26-7.25 (m, 3H), 6.16 (br s, 1H), 5.99 (br s, 1H), 3.15 (t, 2H, J=7.8 Hz), 2.69 (t, 2H, J=7.8 Hz), 1.87-1.81 (m, 2H), 1.75-1.69 (m, 2H), 1.54-1.47 (m, 4H); $^{13}$C NMR (CDCl$_3$, 125 MHz) δ 188.8, 171.5, 157.7, 152.0, 143.1, 134.9, 131.0, 130.2, 128.9, 128.8, 128.7, 128.1, 127.5, 126.0, 124.7, 39.5, 36.3, 31.7, 29.4, 29.4, 24.3; MALDI-FTMS m/z 377.1858 (M+H$^+$, C$_{23}$H$_{25}$N$_2$O$_3$, requires 377.1860).

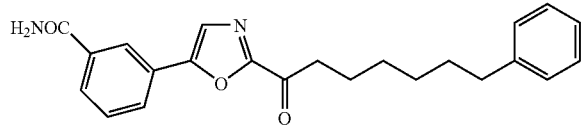

Example 8

3-(2-(7-Phenylheptanoyl)oxazol-5-yl)benzamide

Step 1; 3-(2-(1-(tert-Butyldimethylsilyloxy)-7-phenylheptyl)oxazol-5-yl)benzamide. The title compound was prepared from 2-(1-(tert-butyldimethylsilyloxy)-7-phenylheptyl)-5-(tributylstannyl)oxazole (72 mg, 0.109 mmol) and 3-bromobenzamide following General Procedure A. Flash chromatography (10-40% EtOAc/hexanes) yielded the title compound as a white solid (52 mg, 96%): $^1$H NMR (CD$_3$OD, 600 MHz) δ 8.23 (s, 1H), 8.03 (s, 1H), 7.83 (m, 1H), 7.53 (m, 1H), 7.35 (m, 1H), 7.18-7.09 (m, 5H), 3.30 (t, 1H, J=6.0 Hz), 2.53 (t, 2H, J=7.5 Hz), 1.92-1.86 (m, 2H), 1.65-1.55 (m, 2H), 1.34-1.29 (m, 6H), 0.87 (s, 9H), 0.09 (s; 3H), −0.03 (s, 3H); $^{13}$C NMR (CD$_3$OD, 150 MHz) δ 166.2, 151.6, 143.3, 136.6, 135.4, 131.3, 130.8, 128.8, 128.7, 126.9, 126.1, 124.0, 122.9, 122.6, 69.2, 36.8, 36.3, 32.0, 29.6, 29.5, 25.7, 25.6, 18.5, −5.3, −5.4.

Step 2. The title compound was prepared from 3-(2-(1-(tert-butyldimethylsilyloxy)-7-phenylheptyl)oxazol-5-yl)benzamide (48 mg, 0.097 mmol) following General Procedure C. Flash chromatography (10-70% EtOAc/hexanes) yielded the title compound as a white solid (15 mg, 41%): $^1$H NMR (THF-d$_8$, 600 MHz) δ 8.31 (s, 1H), 7.94-7.92 (m, 1H), 7.76 (s, 1H), 7.54-7.52 (m, 2H), 7.22-7.19 (m, 2H), 7.16-7.14 (m, 2H), 7.11-7.08 (m, 1H), 6.77 (br s, 1H), 3.05 (t, 2H, J=7.8 Hz), 2.60 (t, 2H, J=7.8 Hz), 1.74-1.71 (m, 2H), 1.66-1.61 (m, 2H), 1.44-1.39 (m, 4H); $^{13}$C NMR (THF-d$_8$, 150 MHz) δ 187.7, 167.6, 158.4, 154.2, 143.3, 136.8, 129.7, 129.6, 129.0, 128.8, 128.0, 128.0, 126.2, 125.1, 124.7, 39.3, 36.6, 32.3, 29.9, 29.8, 24.6; MALDI-FTMS m/z 377.1864 (M+H$^+$, C$_{23}$H$_{25}$N$_2$O$_3$, requires 377.1860).

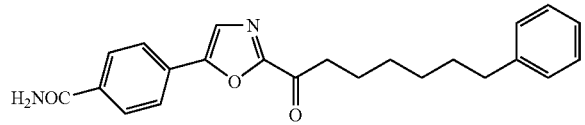

Example 9

4-(2-(7-Phenylheptanoyl)oxazol-5-yl)benzamide

Step 1; 4-(2-(1-(tert-Butyldimethylsilyloxy)-7-phenylheptyl)oxazol-5-yl)benzamide. The title compound was prepared from 2-(1-(tert-butyldimethylsilyloxy)-7-phenylheptyl)-5-(tributylstannyl)oxazole (47 mg, 0.071 mmol) and 4-bromobenzamide following General Procedure A. Flash chromatography (30-50% EtOAc/hexanes) yielded the title compound as a white solid (29 mg, 83%): $^1$H NMR (CDCl$_3$, 600 MHz) δ 7.67 (d, 2H, J=7.8 Hz), 7.57 (d, 2H, J=7.8 Hz), 7.38 (s, 1H), 7.25-7.24 (m, 2H), 7.15-7.14 (m, 3H), 6.16 (br s, 2H), 4.84 (t, 1H, J=6.0 Hz), 2.58 (t, 2H, J=7.5 Hz), 1.93-1.87 (m, 2H), 1.58-1.56 (m, 2H), 1.46-1.34 (m, 6H), 0.88 (s, 9H), 0.09 (s, 3H), −0.01 (s, 3H); $^{13}$C NMR (CDCl$_3$, 150 MHz) δ 169.5, 143.6, 132.8, 129.9, 129.5, 129.2, 129.1, 129.0, 128.3, 127.7, 126.4, 125.0, 69.4, 37.3, 36.8, 32.2, 30.0, 26.6, 26.0, 19.1, −4.1, −4.2.

Step 2. The title compound was prepared from 4-(2-(1-(tert-butyldimethylsilyloxy)-7-phenylheptyl)oxazol-5-yl)benzamide (29 mg, 0.059 mmol) following General Procedure C. Flash chromatography (40-80% EtOAc/hexanes) yielded the title compound as a white solid (7 mg, 32%): $^1$H NMR (CD$_3$OD, 500 MHz) δ 8.08 (d, 2H, J=8.5 Hz), 8.02 (d, 2H, J=8.5 Hz), 7.93 (s, 1H), 7.32-7.29 (m, 2H), 7.25-7.20 (m, 3H), 3.17 (t, 2H, J=7.8 Hz), 2.69 (t, 2H, J=7.8 Hz), 1.85-1.80 (m, 2H), 1.75-1.70 (m, 2H), 1.55-1.45 (m, 4H); $^{13}$C NMR (CD$_3$OD, 125 MHz) δ 188.6, 168.8, 160.8, 158.0, 153.5, 142.9, 128.6, 128.4, 128.2, 127.7, 125.6, 125.4, 125.2, 38.8, 35.8, 31.5, 29.0, 29.0, 23.9; MALDI-FTMS m/z 377.1864 (M+H$^+$, C$_{23}$H$_{25}$N$_2$O$_3$, requires 377.1860).

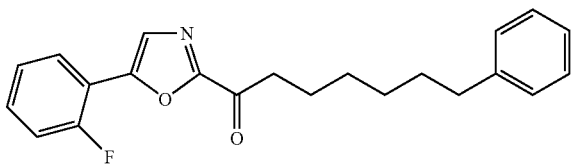

Example 10

1-(5-(2-Fluorophenyl)oxazol-2-yl)-7-phenylheptan-1-one

Step 1; 2-(1-(tert-Butyldimethylsilyloxy)-7-Phenylheptyl)-5-(2-fluorophenyl)oxazole. The title compound was prepared from 2-(1-(tert-butyldimethylsilyloxy)-7-phenylheptyl)-5-(tributylstannyl)oxazole (75 mg, 0.113 mmol) and 1-fluoro-2-iodobenzene following General Procedure A. Flash chromatography (2% EtOAc/hexanes) yielded the title compound as a clear oil (52 mg, 98%): $^1$H NMR (CDCl$_3$, 400 MHz) 7.77 (dt, 1H, J=9.6, 5.6 Hz), 7.42 (d, 1H, J=4.0 Hz), 7.31-7.21 (m, 4H), 7.18-7.13 (m, 4H), 4.85 (t, 1H, J=6.0 Hz), 2.59 (t, 2H, J=7.2 Hz), 1.90-1.93 (m, 2H), 1.62-1.60 (m, 2H), 1.33-1.36 (m, 6H), 0.90 (s, 9H), 0.11 (s, 3H), 0.00 (s, 3H); $^{13}$C NMR (CDCl$_3$, 100 MHz) δ 169.7, 163.4 (d, J=250 Hz), 150.6, 157.9, 134.4 (d, J=8.3 Hz), 133.5, 133.3, 131.2 (d, J=12.6 Hz), 131.1, 131.1, 130.7, 129.6 (d, J=3.2 Hz), 121.7 (d, J=13.0 Hz), 120.1 (d, J=20.9 Hz), 73.8, 41.6, 41.0, 36.5, 34.3, 34.3, 30.9, 30.3, 23.3, 0.2, 0.0.

Step 2. The title compound was prepared from 2-(1-(tert-butyldimethylsilyloxy)-7-phenylheptyl)-5-(2-fluorophenyl)oxazole (40 mg, 0.086 mmol) following General Procedure C. Flash chromatography (10-20% EtOAc/hexanes) yielded the title compound as a clear oil (20 mg, 67%): $^1$H NMR (CDCl$_3$, 500 MHz) δ 8.02 (dt, 1H, J=9.2, 5.9 Hz), 7.73 (d, 1H, J=4.0 Hz), 7.49-7.46 (m, 1H), 7.37-7.34 (m, 3H), 7.27-7.23 (m, 4H), 3.18 (t, 1H, J=7.4 Hz), 2.69 (t, 2H, J=7.7 Hz), 1.89-1.85 (m, 2H), 1.73-1.71 (m, 2H), 1.52-1.47 (m, 4H); $^{13}$C NMR (CDCl$_3$, 125 MHz) δ 188.8, 159.5 (d, J=251 Hz), 157.1, 149.0, 143.1, 131.6 (d, J=8.3 Hz), 128.8, 128.7, 128.2 (d, J=13.4 Hz), 127.6, 127.6, 126.0, 125.3 (d, J=3.4 Hz), 116.5 (d, J=20.6 Hz), 115.8 (d, J=12.7 Hz), 39.5, 36.3, 31.7, 29.4, 29.4, 24.4; MALDI-FTMS m/z 352.1704 (M+H$^+$, C$_{22}$H$_{23}$FNO$_2$, requires 352.1707).

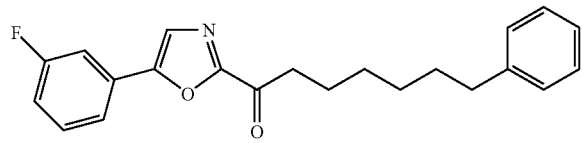

Example 11

1-(5-(3-Fluorophenyl)oxazol-2-yl)-7-phenylheptan-1-one

Step 1; 2-(1-(tert-Butyldimethylsilyloxy)-7-Phenylheptyl)-5-(3-fluorophenyl)oxazole. The title compound was prepared from 2-(1-(tert-butyldimethylsilyloxy)-7-phenylheptyl)-5-(tributylstannyl)oxazole (75 mg, 0.113 mmol) and 1-fluoro-3-iodobenzene following General Procedure A. Flash chromatography (2% EtOAc/hexanes) yielded the title compound as a clear oil (53 mg, 98%): $^1$H NMR (CDCl$_3$, 400 MHz) 7.43-7.33 (m, 3H), 7.29-7.25 (m, 3H), 7.18-7.15 (m, 3H), 7.04-7.00 (m, 1H), 4.83 (t, 1H, J=6.0 Hz), 2.59 (t, 2H, J=7.6 Hz), 1.96-1.88 (m, 2H), 1.63-1.59 (m, 2H), 1.47-1.35 (m, 6H), 0.90 (s, 9H), 0.10 (s, 3H), 0.00 (s, 3H); $^{13}$C NMR (CDCl$_3$, 100 MHz) δ 170.4, 167.3 (d, J=245 Hz), 155.1, 147.9, 135.6 (d, J=8.4 Hz), 135.2 (d, J=8.5 Hz), 133.5, 133.3, 130.7, 127.7, 124.9 (d, J=3.0 Hz), 120.2 (d, J=21.1), 116.2 (d, J=23.5), 73.8, 41.5, 41.0, 36.5, 34.3, 34.3, 30.8, 30.2, 23.3, 0.2, 0.0.

Step 2. The title compound was prepared from 2-(1-(tert-butyldimethylsilyloxy)-7-phenylheptyl)-5-(3-fluorophenyl)oxazole (50 mg, 0.106 mmol) following General Procedure C. Flash chromatography (2-10% EtOAc/hexanes) yielded the title compound as a white solid (26 mg, 68%): $^1$H NMR (CDCl$_3$, 500 MHz) δ 7.65-7.60 (m, 2H), 7.56-7.49 (m, 2H), 7.37-7.34 (m, 2H), 7.27-7.25 (m, 3H), 7.21-7.18 (m, 1H), 3.16 (t, 2H, J=7.5 Hz), 2.69 (t, 2H, J=7.5 Hz), 1.88-1.85 (m, 2H), 1.74-1.71 (m, 2H), 1.52-1.48 (m, 4H); $^{13}$C NMR (CDCl$_3$, 125 MHz) δ 188.7, 163.4 (d, J=245 Hz), 157.7, 153.3, 143.1, 131.3 (d, J=8.4 Hz), 129.1 (d, J=8.5 Hz), 128.8, 128.7, 126.0, 124.9, 121.4 (d, J=3.0 Hz), 117.3 (d, J=21.1), 112.7 (d, J=23.8), 39.5, 36.3, 31.7, 29.4, 29.4, 24.4; MALDI-FTMS m/z 352.1706 (M+H$^+$, C$_{22}$H$_{23}$FNO$_2$, requires 352.1707).

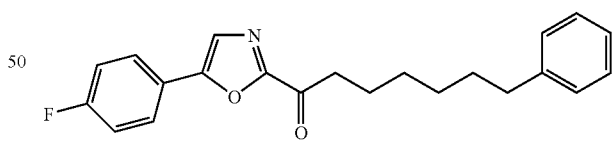

Example 12

1-(5-(4-Fluorophenyl)oxazol-2-yl)-7-phenylheptan-1-one

Step 1; 2-(1-(tert-Butyldimethylsilyloxy)-7-phenylheptyl)-5-(4-fluorophenyl)oxazole. The title compound was prepared from 2-(1-(tert-butyldimethylsilyloxy)-7-phenylheptyl)-5-(tributylstannyl)oxazole (81 mg, 0.122 mmol) and 1-fluoro-4-iodobenzene following General Procedure A. Flash chromatography (2% EtOAc/hexanes) yielded the title compound as a clear oil (40 mg, 61%): $^1$H NMR (CDCl$_3$, 600

MHz) δ 7.63-7.61 (m, 2H), 7.27-7.24 (m, 4H), 7.17-7.11 (m, 4H), 4.88 (t, 1H, J=6.0 Hz), 2.58 (t, 2H, J=7.5 Hz), 1.95-1.90 (m, 2H), 1.62-1.59 (m, 2H), 1.46-1.35 (m, 6H), 0.89 (s, 9H), 0.10 (s, 3H), −0.01 (s, 3H); $^{13}$C NMR (CDCl$_3$, 150 MHz) δ 165.9, 163.5 (d, J=258 Hz), 151.5, 143.6, 129.2, 129.1, 127.1 (d, J=8.3 Hz), 126.4, 124.8, 121.1, 117.0 (d, J=22 Hz), 69.4, 37.3, 36.8, 32.3, 30.0, 26.6, 26.6, 25.9, 19.1, −4.1, −4.2.

Step 2. The title compound was prepared from 2-(1-(tert-butyldimethylsilyloxy)-7-phenylheptyl)-5-(4-fluorophenyl)oxazole (60 mg, 0.110 mmol) following General Procedure C. Flash chromatography (2-10% EtOAc/hexanes) yielded the title compound as a white solid (24 mg, 62%): $^1$H NMR (CDCl$_3$, 600 MHz) δ 7.77-7.74 (m, 2H), 7.44 (s, 1H), 7.28-7.25 (m, 2H), 7.17-7.14 (m, 3H), 3.07 (t, 2H, J=7.8 Hz), 2.60 (t, 2H, J=7.8 Hz), 1.78-1.76 (m, 2H), 1.65-1.62 (m, 2H), 1.45-1.38 (m, 4H); $^{13}$C NMR (CDCl$_3$, 150 MHz) δ 189.2, 164.6 (d, J=250 Hz), 158.0, 154.2, 143.5, 129.3, 129.1, 128.3 (d, J=8.6 Hz), 126.5, 124.2, 123.9, 117.2 (d, J=22 Hz), 39.8, 36.7, 32.2, 29.9, 29.9, 24.9; MALDI-FTMS m/z 352.1701 (M+H$^+$, C$_{22}$H$_{23}$FNO$_2$, requires 352.1707).

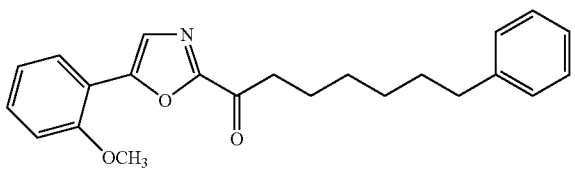

Example 13

1-(5-(2-Methoxyphenyl)oxazol-2-yl)-7-phenylheptan-1-one

Step 1: 2-(1-(tert-Butyldimethylsilyloxy)-7-phenylheptyl)-5-(2-methoxyphenyl)oxazole. The title compound was prepared from 2-(1-(tert-butyldimethylsilyloxy)-7-phenylheptyl)-5-(tributylstannyl)oxazole (140 mg, 0.211 mmol) and 1-iodo-2-methoxybenzene following General Procedure A. Flash chromatography (2% EtOAc/hexanes) yielded the title compound as a white solid (78 mg, 77%): $^1$H NMR (CDCl$_3$, 400 MHz) δ 7.81 (dd, 1H, J=9.2, 6.0 Hz), 7.49 (s, 1H), 7.30-7.27 (m, 3H), 7.19-7.16 (m, 3H), 7.07-7.05 (m, 1H), 6.99 (d, 1H, J=8.4 Hz), 4.85 (t, 1H, J=6.8 Hz), 3.98 (s, 3H), 2.58 (t, 2H, J=8.0 Hz), 1.95-1.91 (m, 2H), 1.63-1.60 (m, 2H), 1.38-1.34 (m, 6H), 0.91 (s, 9H), 0.11 (s, 3H), 0.00 (s, 3H); $^{13}$C NMR (CDCl$_3$, 100 MHz) δ 168.8, 160.7, 152.7, 148.0, 134.0, 133.5, 133.3, 131.0, 130.9, 130.7, 125.9, 122.4, 115.9, 73.8, 60.5, 41.6, 41.1, 36.6, 34.3, 34.3, 30.9, 30.3, 23.3, 0.2, 0.0.

Step 2. The title compound was prepared from 2-(1-(tert-butyldimethylsilyloxy)-7-phenylheptyl)-5-(2-methoxyphenyl)oxazole (78 mg, 0.163 mmol) following General Procedure C. Flash chromatography (10% EtOAc/hexanes) yielded the title compound as a white solid (42 mg, 71%): $^1$H NMR (CDCl$_3$, 400 MHz) δ 7.92 (dd, 1H, J=9.2, 6.0 Hz), 7.68 (s, 1H), 7.37-7.33 (m, 1H), 7.26-7.22 (m, 2H), 7.16-7.14 (m, 3H), 7.04 (t, 1H, J=7.2 Hz), 6.97 (d, 1H, J=8.4 Hz), 3.95 (s, 3H), 3.06 (t, 2H, J=7.2 Hz), 2.58 (t, 2H, J=7.6 Hz), 1.77-1.73 (m, 2H), 1.63-1.59 (m, 2H), 1.42-1.37 (m, 4H); $^{13}$C NMR (CDCl$_3$, 100 MHz) δ 188.6, 156.7, 156.2, 151.1, 142.9, 131.0, 128.6, 128.4, 128.0, 127.4, 125.8, 121.2, 116.1, 111.1, 55.7, 39.2, 36.1, 31.5, 29.2, 29.2, 24.3; MALDI-FTMS m/z 364.1904 (M+H$^+$, C$_{23}$H$_{26}$NO$_3$, requires 364.1907).

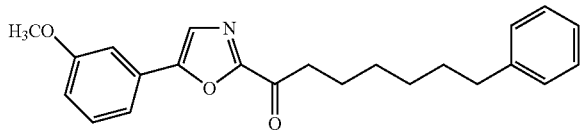

Example 14

1-(5-(3-Methoxyphenyl)oxazol-2-yl)-7-phenylheptan-1-one

Step 1; 2-(1-(tert-Butyldimethylsilyloxy)-7-phenylheptyl)-5-(3-methoxyphenyl)oxazole. The title compound was prepared from 2-(1-(tert-butyldimethylsilyloxy)-7-phenylheptyl)-5-(tributylstannyl)oxazole (190 mg, 0.287 mmol) and 1-iodo-3-methoxybenzene following General Procedure A. Flash chromatography (2-10% EtOAc/hexanes) yielded the title compound as a clear oil (107 mg, 78%): $^1$H NMR (CDCl$_3$, 500 MHz) δ 8.40 (m, 1H), 8.07 (d, 1H, J=8.0 Hz), 7.90 (d, 1H, J=8.0 Hz), 7.58 (t, 1H, J=7.6 Hz), 7.44 (s, 1H), 7.35-7.32 (m, 2H), 7.25-7.23 (m, 3H), 4.93 (t, 1H, J=6.0 Hz), 4.03 (s, 3H), 2.67 (t, 2H, J=7.4 Hz), 2.04-1.99 (m, 2H), 1.75-1.68 (m, 2H), 1.45-1.37 (m, 6H), 1.00 (s, 9H), 0.20 (s, 3H), 0.10 (s, 3H); $^{13}$C NMR (CDCl$_3$, 125 MHz) δ 166.9, 165.7, 150.6, 143.1, 131.4, 129.7, 129.5, 128.9, 128.8, 128.6, 128.6, 126.1, 125.8, 123.5, 69.1, 52.7, 36.8, 36.4, 31.8, 29.6, 29.6, 26.2, 25.6, 14.1, −4.5, −4.6.

Step 2. The title compound was prepared from 2-(1-(tert-butyldimethylsilyloxy)-7-phenylheptyl)-5-(3-methoxyphenyl)oxazole (105 mg, 0.219 mmol) following General Procedure C. Flash chromatography (5-20% EtOAc/hexanes) yielded the title compound as a white solid (53 mg, 66%): $^1$H NMR (CDCl$_3$, 500 MHz) δ 8.48 (m, 1H), 8.15 (d, 1H, J=7.5 Hz), 8.03 (d, 1H, J=8.5 Hz), 7.66 (s, 1H), 7.62 (t, 1H, J=8.0 Hz), 7.34 (t, 2H, J=8.5 Hz), 7.26-7.24 (m, 3H), 4.04 (s, 3H), 3.17 (t, 2H, J=7.6 Hz), 2.69 (t, 2H, J=7.6 Hz), 1.87-1.83 (m, 2H), 1.75-1.69 (m, 2H), 1.54-1.46 (m, 4H); $^{13}$C NMR (CDCl$_3$, 125 MHz) δ 188.7, 166.6, 157.7, 153.5, 143.1, 131.6, 131.2, 129.8, 129.7, 128.8, 128.7, 127.5, 126.7, 126.0, 124.9, 52.9, 39.5, 36.3, 31.7, 29.4, 29.4, 24.4; MALDI-FTMS m/z 364.1908 (M+H$^+$, C$_{23}$H$_{26}$NO$_3$, requires 364.1907).

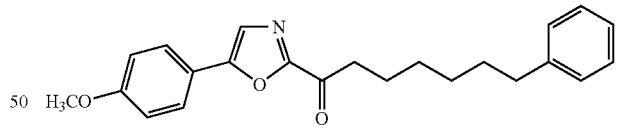

Example 15

1-(5-(4-Methoxyphenyl)oxazol-2-yl)-7-phenylheptan-1-one

Step 1; 2-(1-(tert-Butyldimethylsilyloxy)-7-phenylheptyl)-5-(4-methoxyphenyl)oxazole. The title compound was prepared from 2-(1-(tert-butyldimethylsilyloxy)-7-phenylheptyl)-5-(tributylstannyl)oxazole (67 mg, 0.101 mmol) and 1-bromo-4-methoxybenzene following General Procedure B. Flash chromatography (5% EtOAc/hexanes) yielded the title compound as a clear oil (41 mg, 84%): $^1$H NMR (CDCl$_3$, 500 MHz) δ 7.66 (d, 2H, J=9.0 Hz), 7.37-7.34 (m, 3H), 7.27-7.23 (m, 3H), 7.03 (d, 2H, J=9.0 Hz), 4.91 (t, 1H, J=5.5 Hz), 3.93

(s, 3H), 2.68 (t, 2H, J=7.5 Hz), 2.06-1.96 (m, 2H), 1.71-1.68 (m, 2H), 1.46-1.42 (m, 6H), 0.98 (s, 9H), 0.19 (s, 3H), 0.08 (s, 3H); $^{13}$C NMR (CDCl$_3$, 125 MHz) δ 164.6, 160.2, 151.6, 143.2, 128.8, 128.7, 126.1, 126.0, 121.3, 120.3, 114.8, 69.1, 55.8, 36.8, 36.3, 31.9, 29.6, 26.2, 26.2, 25.6, 18.7, −4.5, −4.7.

Step 2. The title compound was prepared from 2-(1-(tert-butyldimethylsilyloxy)-7-phenylheptyl)-5-(4-methoxyphenyl)oxazole (39 mg, 0.081 mmol) following General Procedure C. Flash chromatography (5-10% EtOAc/hexanes) yielded the title compound as a white solid (18 mg, 60%): $^1$H NMR (CDCl$_3$, 600 MHz) δ 7.70 (d, 2H, J=9.0 Hz), 7.38 (s, 1H), 7.27-7.25 (m, 2H), 7.17-7.16 (m, 3H), 6.96 (d, 2H, J=9.0 Hz), 3.85 (s, 3H), 3.06 (t, 2H, J=7.2 Hz), 2.60 (t, 2H, J=7.2 Hz), 1.79-1.75 (m, 2H), 1.65-1.61 (m, 2H), 1.44-1.37 (m, 4H); $^{13}$C NMR (CDCl$_3$, 150 MHz) δ 189.1, 161.8, 157.6, 155.3, 143.6, 129.3, 129.1, 127.8, 126.4, 123.2, 120.2, 115.4, 56.3, 39.7, 36.8, 32.2, 29.9, 29.9, 25.0; MALDI-FTMS m/z 364.1908 (M+H$^+$, C$_{23}$H$_{26}$NO$_3$, requires 364.1907).

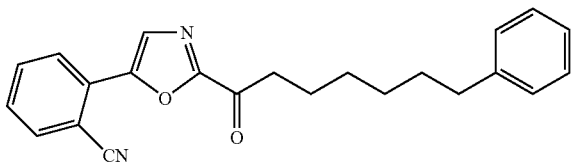

Example 16

2-(2-(7-Phenylheptanoyl)oxazol-5-yl)benzonitrile

Step 1; 2-(2-(1-(tert-Butyldimethylsilyloxy)-7-phenylheptyl)oxazol-5-yl)benzonitrile. The title compound was prepared from 2-(1-(tert-butyldimethylsilyloxy)-7-phenylheptyl)-5-(tributylstannyl)oxazole (60 mg, 0.091 mmol) and 2-bromobenzonitrile following General Procedure A. Flash chromatography (2-5% EtOAc/hexanes) yielded the title compound as a clear oil (35 mg, 81%): $^1$H NMR (CDCl$_3$, 600 MHz) δ 7.90 (s, 1H), 7.85 (d, 1H, J=7.8 Hz), 7.74 (d, 1H, J=7.8 Hz), 7.66 (t, 1H, J=7.8 Hz), 7.40 (t, 1H, J=7.8 Hz), 7.27-7.25 (m, 2H), 7.16-7.15 (m, 3H), 4.87 (t, 1H, J=6.0 Hz), 2.59 (t, 2H, J=7.8 Hz), 1.96-1.90 (m, 2H), 1.62-1.60 (m, 2H), 1.38-1.36 (m, 6H), 0.90 (s, 9H), 0.10 (s, 3H), 0.00 (s, 3H); $^{13}$C NMR (CDCl$_3$, 150 MHz) δ 166.7, 148.06, 143.6, 135.0, 134.1, 131.7, 129.2, 129.1, 129.0, 127.3, 126.9, 126.4, 124.2, 119.2, 108.3, 69.5, 37.3, 36.8, 32.3, 30.0, 26.6, 26.6, 26.0, 19.1, −4.1, −4.2.

Step 2. The title compound was prepared from 2-(2-(1-(tert-butyldimethylsilyloxy)-7-phenylheptyl)oxazol-5-yl)benzonitrile (33 mg, 0.070 mmol) following General Procedure C. Flash chromatography (5-20% EtOAc/hexanes) yielded the title compound as a white solid (16 mg, 64%): $^1$H NMR (CDCl$_3$, 600 MHz) δ 8.12 (s, 1H), 8.03 (d, 1H, J=8.4 Hz), 7.79 (d, 1H, J=7.8 Hz), 7.72 (t, 1H, J=7.8 Hz), 7.51 (t, 1H, J=7.8 Hz), 7.27-7.25 (m, 2H), 7.17-7.16 (m, 3H), 3.11 (t, 2H, J=7.2 Hz), 2.61 (t, 2H, J=7.2 Hz), 1.79-1.77 (m, 2H), 1.65-1.62 (m, 2H), 1.44-1.41 (m, 4H); $^{13}$C NMR (CDCl$_3$, 150 MHz) δ 189.3, 158.1, 150.7, 143.5, 135.1, 134.3, 130.5, 130.4, 129.3, 129.1, 128.8, 128.2, 126.5, 118.9, 109.4, 40.1, 36.7, 32.2, 29.8, 29.8, 24.7; MALDI-FTMS m/z 359.1750 (M+H$^+$, C$_{23}$H$_{23}$N$_2$O$_2$, requires 359.1754).

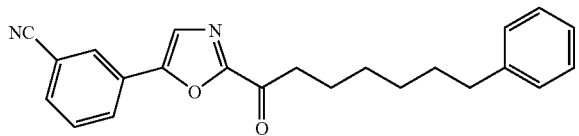

Example 17

3-(2-(7-Phenylheptanoyl)oxazol-5-yl)benzonitrile

Step 1; 3-(2-(1-(tert-Butyldimethylsilyloxy)-7-phenylheptyl)oxazol-5-yl)benzonitrile. The title compound was prepared from 2-(1-(tert-butyldimethylsilyloxy)-7-phenylheptyl)-5-(tributylstannyl)oxazole (60 mg, 0.091 mmol) and 3-bromobenzonitrile following General Procedure A. Flash chromatography (2-5% EtOAc/hexanes) yielded the title compound as a clear oil (31 mg, 72%): $^1$H NMR (CDCl$_3$, 600 MHz) δ 7.91 (s, 1H), 7.84 (d, 1H, J=7.8 Hz), 7.59 (d, 1H, J=7.8 Hz), 7.53 (t, 1H, J=7.8 Hz), 7.36 (s, 1H), 7.27-7.24 (m, 2H), 7.16-7.15 (m, 3H), 4.83 (t, 1H, J=6.0 Hz), 2.58 (t, 2H, J=7.8 Hz), 1.95-1.88 (m, 2H), 1.65-1.59 (m, 2H), 1.36-1.33 (m, 6H), 0.89 (s, 9H), 0.10 (s, 3H), −0.01 (s, 3H); $^{13}$C NMR (CDCl$_3$, 150 MHz) δ 166.8, 149.8, 143.6, 132.3, 130.7, 130.2, 129.2, 129.1, 128.9, 128.3, 126.5, 124.2, 119.1, 114.2, 69.5, 37.3, 36.8, 32.3, 30.0, 26.6, 26.6, 26.0, 19.1, −4.1, −4.2.

Step 2. The title compound was prepared from 3-(2-(1-(tert-butyldimethylsilyloxy)-7-phenylheptyl)oxazol-5-yl)benzonitrile (29 mg, 0.061 mmol) following General Procedure C. Flash chromatography (5-20% EtOAc/hexanes) yielded the title compound as a white solid (14 mg, 64%): $^1$H NMR (CDCl$_3$, 600 MHz) δ 8.05 (s, 1H), 8.00 (d, 1H, J=7.8 Hz), 7.68 (d, 1H, J=7.8 Hz), 7.59-7.58 (m, 2H), 7.27-7.25 (m, 2H), 7.17-7.16 (m, 3H), 3.08 (t, 2H, J=7.2 Hz), 2.60 (t, 2H, J=7.2 Hz), 1.78-1.76 (m, 2H), 1.64-1.62 (m, 2H), 1.43-1.39 (m, 4H); $^{13}$C NMR (CDCl$_3$, 150 MHz) δ 189.1, 158.4, 152.5, 143.5, 133.8, 133.8, 131.0, 130.0, 129.4, 129.3, 129.1, 128.9, 126.5, 125.9, 118.7, 114.6, 40.0, 36.7, 32.1, 29.9, 29.9, 24.8; MALDI-FTMS m/z 359.1767 (M+H$^+$, C$_{23}$H$_{23}$N$_2$O$_2$, requires 359.1754).

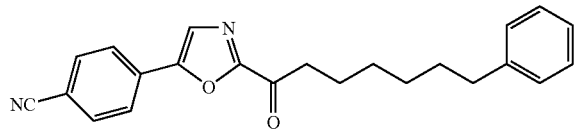

Example 18

4-(2-(7-Phenylheptanoyl)oxazol-5-yl)benzonitrile

Step 1; 4-(2-(1-(tert-Butyldimethylsilyloxy)-7-phenylheptyl)oxazol-5-yl)benzonitrile. The title compound was prepared from 2-(1-(tert-butyldimethylsilyloxy)-7-phenylheptyl)-5-(tributylstannyl)oxazole (53 mg, 0.080 mmol) and 4-bromobenzonitrile following General Procedure A. Flash chromatography (5-10% EtOAc/hexanes) yielded the title compound as a clear oil (30 mg, 79%): $^1$H NMR (CDCl$_3$, 500 MHz) δ 7.82-7.78 (m, 4H), 7.50 (s, 1H), 7.36-7.33 (m, 2H), 7.26-7.23 (m, 3H), 4.93 (t, 1H, J=5.5 Hz), 2.67 (t, 2H, J=7.5 Hz), 2.06-1.95 (m, 2H), 1.75-1.67 (m, 2H), 1.47-1.40 (m, 6H), 0.98 (s, 9H), 0.19 (s, 3H), 0.08 (s, 3H); $^{13}$C NMR (CDCl$_3$, 125 MHz) δ 166.7, 149.7, 143.2, 133.2, 132.4, 128.8, 128.7, 126.0, 124.8, 124.8, 119.0, 112.0, 69.1, 36.8, 36.3, 31.8, 29.6, 28.3, 26.1, 25.5, 18.6, −4.5, −4.7.

Step 2. The title compound was prepared from 4-(2-(1-(tert-butyldimethylsilyloxy)-7-phenylheptyl)oxazol-5-yl)benzonitrile (51 mg, 0.107 mmol) following General Procedure C. Flash chromatography (5-20% EtOAc/hexanes) yielded the title compound as a white solid (13 mg, 33%): $^1$H NMR (CDCl$_3$, 600 MHz) δ 7.87 (d, 2H, J=8.4 Hz), 7.75 (d, 2H, J=8.4 Hz), 7.63 (s, 1H), 7.27-7.25 (m, 2H), 7.17-7.16 (m, 3H), 3.08 (t, 2H, J=7.2 Hz), 2.60 (t, 2H, J=7.2 Hz), 1.79-1.75 (m, 2H), 1.65-1.61 (m, 2H), 1.44-1.37 (m, 4H); $^{13}$C NMR (CDCl$_3$, 150 MHz) δ 189.2, 158.6, 152.8, 143.5, 133.8, 131.5, 129.3, 129.1, 126.8, 126.5, 126.5, 40.0, 36.7, 32.1, 29.9, 29.9, 24.8; MALDI-FTMS m/z 359.1755 (M+H$^+$, C$_{23}$H$_{23}$N$_2$O$_2$, requires 359.1754).

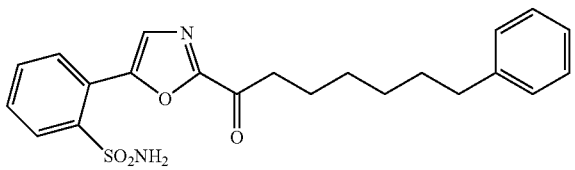

Example 19

2-(2-(7-Phenylheptanoyl)oxazol-5-yl)benzenesulfonamide

Step 1; 2-(2-(1-(tert-Butyldimethylsilyloxy)-7-phenylheptyl)oxazol-5-yl)benzenesulfonamide. The title compound was prepared from 2-(1-(tert-butyldimethylsilyloxy)-7-phenylheptyl)-5-(tributylstannyl)oxazole (71 mg, 0.107 mmol) and 2-iodobenzenesulfonamide following General Procedure A. Flash chromatography (2-10% EtOAc/hexanes) yielded the title compound as a clear oil (25 mg, 44%): $^1$H NMR (CDCl$_3$, 400 MHz) δ 8.18 (d, 1H, J=7.6 Hz), 7.62-7.59 (m, 2H), 7.54-7.51 (m, 1H), 7.42-7.39 (m, 1H), 7.36 (s, 1H), 7.24-7.22 (m, 2H), 7.16-7.12 (m, 3H), 5.29 (ex s, 2H), 4.88 (t, 1H, J=6.7 Hz), 2.56 (t, 2H, J=7.6 Hz), 1.86-1.84 (m, 2H), 1.62-1.59 (m, 2H), 1.31-1.29 (m, 6H). 0.86 (s, 9H), 0.09 (s, 3H), 0.00 (s, 3H); $^{13}$C NMR (CDCl$_3$, 100 MHz) δ 170.7, 153.6, 148.0, 144.9, 137.9, 135.7, 134.6, 134.3, 133.6, 133.4, 133.3, 131.0, 130.8, 42.3, 41.1, 36.3, 34.9, 34.3, 34.3, 31.0, 30.0, 23.5, 0.4, 0.0.

Step 2. The title compound was prepared from 2-(2-(1-(tert-butyldimethylsilyloxy)-7-phenylheptyl)oxazol-5-yl)benzenesulfonamide (23 mg, 0.043 mmol) following General Procedure C. Flash chromatography (10-30% EtOAc/hexanes) yielded the title compound as a white solid (12 mg, 67%): $^1$H NMR (CDCl$_3$, 400 MHz) δ 8.19-8.17 (m, 1H), 7.61-7.53 (m, 3H), 7.48 (s, 1H), 7.20-7.19 (m, 2H), 7.12-7.10 (m, 3H), 5.50 (ex s, 2H), 3.04 (t, 2H, J=7.2 Hz), 2.54 (t, 2H, J=7.2 Hz), 1.70-1.69 (m, 2H), 1.58-1.56 (m, 2H), 1.37-1.33 (m, 4H);

$^{13}$C NMR (CDCl$_3$, 100 MHz) δ 189.2, 157.8, 152.1, 143.1, 141.2, 133.1, 131.1, 131.1, 130.0, 128.8, 128.7, 128.3, 127.4, 126.0, 39.0, 36.3, 31.7, 29.4, 29.4, 24.1; MALDI-FTMS m/z 413.1537 (M+H$^+$, C$_{22}$H$_{25}$N$_2$O$_4$S, requires 413.1529).

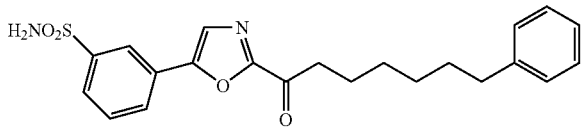

Example 20

3-(2-(7-Phenylheptanoyl)oxazol-5-yl)benzenesulfonamide

Step 1; 3-(2-(1-(tert-Butyldimethylsilyloxy)-7-phenylheptyl)oxazol-5-yl)benzenesulfonamide. The title compound was prepared from 2-(1-(tert-butyldimethylsilyloxy)-7-phenylheptyl)-5-(tributylstannyl)oxazole (75 mg, 0.113 mmol) and 3-bromobenzenesulfonamide following General Procedure A. Flash chromatography (10-30% EtOAc/hexanes) yielded the title compound as a white solid (55 mg, 91%): $^1$H NMR (CD$_3$OD, 500 MHz) δ 8.24 (m, 1H), 7.92 (d, 1H, J=8.0 Hz), 7.74 (d, 1H, J=8.0 Hz), 7.64 (t, 1H, J=7.6 Hz), 7.58 (s, 1H), 7.24-7.20 (m, 2H), 7.14-7.13 (m, 3H), 4.88 (ex s, 2H), 3.32-3.31 (m, 1H), 2.58 (t, 2H, J=7.6 Hz), 1.98-1.86 (m, 2H), 1.69-1.60 (m, 2H), 1.38-1.34 (m, 6H), 0.90 (s, 9H), 0.12 (s, 3H), 0.00 (s, 3H); $^{13}$C NMR (CDCl$_3$, 100 MHz) δ 165.9, 150.3, 142.7, 130.7, 128.9, 128.8, 128.6, 128.2, 128.2, 128.0, 125.4, 124.7, 122.3, 36.1, 35.6, 31.4, 28.9, 28.8, 28.0, 25.0, 24.9, 17.8, −6.0, −6.1.

Step 2. The title compound was prepared from 3-(2-(1-(tert-butyldimethylsilyloxy)-7-phenylheptyl)oxazol-5-yl)benzenesulfonamide (55 mg, 0.104 mmol) following General Procedure C. Flash chromatography (20-60% EtOAc/hexanes) yielded the title compound as a white solid (27 mg, 65%): $^1$H NMR (CD$_3$OD, 500 MHz) δ 8.41-8.40 (m, 1H), 8.10-8.09 (m, 1H), 8.03-8.01 (m, 1H), 7.90 (s, 1H), 7.74 (t, 1H, J=8.0 Hz), 7.31-7.28 (m, 2H), 7.23-7.17 (m, 3H), 3.17-3.14 (t, 2H, J=7.5 Hz) 2.69-2.66 (t, 2H, J=7.6 Hz), 1.85-1.79 (m, 2H), 1.74-1.68 (m, 2H), 1.54-1.44 (m, 4H); $^{13}$C NMR (CD$_3$OD, 125 MHz) δ 188.5, 157.9, 152.9, 145.4, 142.9, 130.2, 128.5, 128.4, 128.3, 128.1 127.2, 125.6, 125.2, 122.7, 38.8, 35.8, 31.5, 29.0, 29.0, 23.8; MALDI-FTMS m/z 413.1540 (M+H$^+$, C$_{22}$H$_{25}$N$_2$O$_4$S, requires 413.1529).

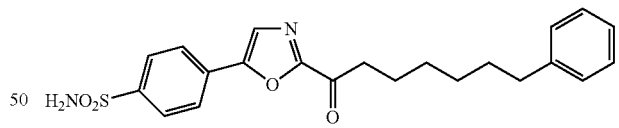

Example 21

4-(2-(7-Phenylheptanoyl)oxazol-5-yl)benzenesulfonamide

Step 1; 4-(2-(1-(tert-Butyldimethylsilyloxy)-7-phenylheptyl)oxazol-5-yl)benzenesulfonamide. The title compound was prepared from 2-(1-(tert-butyldimethylsilyloxy)-7-phenylheptyl)-5-(tributylstannyl)oxazole (63 mg, 0.095 mmol) and 4-bromobenzenesulfonamide following General Procedure A. Flash chromatography (2-20% EtOAc/hexanes) yielded the title compound as a white solid (41 mg, 82%): $^1$H NMR (CDCl$_3$, 500 MHz) δ 8.05 (d, 2H, J=8.5 Hz), 7.83 (d, 2H, J=8.5 Hz), 7.49 (s, 1H), 7.36-7.32 (m, 2H), 7.25-7.22 (m, 3H), 5.39 (s, 2H), 4.92 (t, 1H, J=6.0 Hz), 2.67 (t, 2H, J=7.5 Hz), 2.03-1.96 (m, 2H), 1.74-1.67 (m, 2H), 1.46-1.38 (m, 6H), 0.97 (s, 9H), 0.18 (s, 3H), 0.07 (s, 3H); $^{13}$C NMR (CDCl$_3$, 125 MHz) δ 166.6, 149.9, 141.7, 132.8, 129.6, 128.8, 128.7, 128.4, 127.6, 126.0, 124.9, 124.5, 69.1, 36.8, 36.3, 31.8, 29.6, 26.1, 26.1, 25.5, 18.6, −4.5, −4.6.

Step 2. The title compound was prepared from 4-(2-(1-(tert-butyldimethylsilyloxy)-7-phenylheptyl)oxazol-5-yl)benzenesulfonamide (39 mg, 0.074 mmol) following General Procedure C. Flash chromatography (40% EtOAc/hexanes) yielded the title compound as a white solid (17 mg, 54%): $^1$H NMR (CD$_3$OD, 500 MHz) δ 8.08-8.07 (m, 4H), 7.96 (s, 1H), 7.32-7.38 (m, 5H), 3.17 (t, 2H, J=7.0 Hz), 2.69 (t, 2H, J=7.5 Hz), 1.84-1.81 (m, 2H), 1.73-1.69 (m, 2H), 1.51-1.43 (m, 4H); $^{13}$C NMR (CD$_3$OD, 125 MHz) δ 188.6, 158.1, 152.9, 142.9, 132.4, 130.5, 130.4, 128.4, 128.3, 127.1, 125.9, 125.6, 38.8, 35.8, 31.5, 29.0, 29.0, 23.8; MALDI-FTMS m/z 413.1539 (M+H$^+$, C$_{24}$H$_{25}$NO$_4$, requires 413.1529).

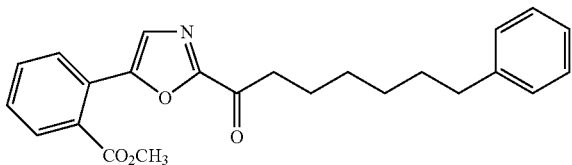

Example 22

Methyl 2-(2-(7-phenylheptanoyl)oxazol-5-yl)benzoate

Step 1; Methyl 2-(2-(1-(tert-butyldimethylsilyloxy)-7-phenylheptyl)oxazol-5-yl)benzoate. The title compound was prepared from 2-(1-(tert-butyldimethylsilyloxy)-7-phenylheptyl)-5-(tributylstannyl)oxazole (166 mg, 0.251 mmol) and methyl 2-iodobenzoate following General Procedure A. Flash chromatography (2-20% EtOAc/hexanes) yielded the title compound as a clear oil (125 mg, 99%): $^1$H NMR (CDCl$_3$, 400 MHz) δ 7.75 (d, 1H, J=7.6 Hz), 7.62 (d, 1H, J=8.0 Hz), 7.53 (t, 1H, J=7.6 Hz), 7.41 (t, 1H, J=7.6 Hz), 7.28-7.24 (m, 3H), 7.17-7.15 (m, 3H), 4.83 (t, 1H, J=6.8 Hz), 3.85 (s, 3H), 2.60 (t, 2H, J=7.4 Hz), 1.92-1.90 (m, 2H), 1.64-1.60 (m, 2H), 1.38-1.33 (m, 6H), 0.90 (s, 9H), 0.11 (s, 3H), 0.00 (s, 3H); $^{13}$C NMR (CDCl$_3$, 100 MHz) δ 173.5, 170.3, 154.6, 147.9, 136.5, 135.1, 135.0, 134.9, 133.7, 133.5, 133.4, 132.3, 130.7, 129.8, 73.8, 57.6, 41.6, 41.1, 36.6, 34.3, 34.3, 30.9, 30.1, 23.4, 0.2, 0.0.

Step 2. The title compound was prepared from methyl 2-(2-(1-(tert-butyldimethylsilyloxy)-7-phenylheptyl)oxazol-5-yl)benzoate (125 mg, 0.246 mmol) following General Procedure C. Flash chromatography (10-20% EtOAc/hexanes) yielded the title compound as a white solid (77 mg, 79%): $^1$H NMR (CDCl$_3$, 400 MHz) δ 7.81 (dd, 1H, J=9.2, 6.4 Hz), 7.66 (dd, 1H, J=9.2, 6.4 Hz), 7.57-7.44 (m, 3H), 7.26-7.22 (m, 2H), 7.15-7.13 (m, 3H), 3.85 (s, 3H), 3.05 (t, 2H, J=7.6 Hz), 2.58 (t, 2H, J=7.6 Hz), 1.76-1.71 (m, 2H), 1.63-1.59 (m, 2H), 1.40-1.37 (m, 4H); $^{13}$C NMR (CDCl$_3$, 100 MHz) δ 188.4, 167.9, 157.5, 152.7, 142.9, 131.8, 130.6, 130.4, 130.1, 129.7, 128.6, 128.4, 126.9, 126.4, 125.8, 52.8, 39.2, 36.1, 31.5, 29.2, 29.2, 24.1; MALDI-FTMS m/z 392.1854 (M+H$^+$, C$_{24}$H$_{26}$NO$_4$, requires 392.1856).

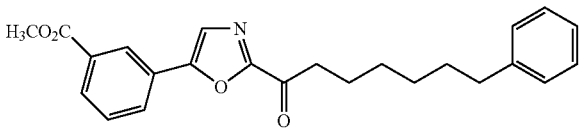

Example 23

Methyl 3-(2-(7-phenylheptanoyl)oxazol-5-yl)benzoate

Step 1; Methyl 3-(2-(1-(tert-butyldimethylsilyloxy)-7-phenylheptyl)oxazol-5-yl)benzoate. The title compound was prepared from 2-(1-(tert-butyldimethylsilyloxy)-7-phenylheptyl)-5-(tributylstannyl)oxazole (188 mg, 0.284 mmol) and methyl 3-bromobenzoate following General Procedure A. Flash chromatography (2-10% EtOAc/hexanes) yielded the title compound as a clear oil (110 mg, 76%): $^1$H NMR (CDCl$_3$, 500 MHz) δ 8.40 (m, 1H), 8.07 (d, 1H, J=8.0 Hz), 7.90 (d, 1H, J=8.0 Hz), 7.58 (t, 1H, J=7.6 Hz), 7.44 (s, 1H), 7.35-7.32 (m, 2H), 7.25-7.23 (m, 3H), 4.93 (t, 1H, J=6.0 Hz), 4.03 (s, 3H), 2.67 (t, 2H, J=7.4 Hz), 2.04-1.99 (m, 2H), 1.75-1.68 (m, 2H), 1.45-1.37 (m, 6H), 1.00 (s, 9H), 0.20 (s, 3H), 0.10 (s, 3H); $^{13}$C NMR (CDCl$_3$, 125 MHz) δ 166.9, 165.7, 150.6, 143.1, 131.4, 129.7, 129.5, 128.9, 128.8, 128.6, 128.6, 126.1, 125.8, 123.5, 69.1, 52.7, 36.8, 36.4, 31.8, 29.6, 29.6, 26.2, 25.6, 14.1, −4.5, −4.6.

Step 2. The title compound was prepared from methyl 3-(2-(1-(tert-butyldimethylsilyloxy)-7-phenylheptyl)oxazol-5-yl)benzoate (106 mg, 0.209 mmol) following General Procedure C. Flash chromatography (10-20% EtOAc/hexanes) yielded the title compound as a white solid (64 mg, 77%): $^1$H NMR (CDCl$_3$, 500 MHz) δ 8.48 (m, 1H), 8.15 (d, 1H, J=7.5 Hz), 8.03 (d, 1H, J=8.5 Hz), 7.66 (s, 1H), 7.62 (t, 1H, J=8.0 Hz), 7.34 (t, 2H, J=8.5 Hz), 7.26-7.24 (m, 3H), 4.04 (s, 3H), 3.17 (t, 2H, J=7.6 Hz), 2.69 (t, 2H, J=7.6 Hz), 1.87-1.83 (m, 2H), 1.75-1.69 (m, 2H), 1.54-1.46 (m, 4H); $^{13}$C NMR (CDCl$_3$, 125 MHz) δ 188.7, 166.6, 157.7, 153.5, 143.1, 131.6, 131.2, 129.8, 129.7, 128.8, 128.7, 127.5, 126.7, 126.0, 124.9, 52.9, 39.5, 36.3, 31.7, 29.4, 29.4, 24.4; MALDI-FTMS m/z 392.1860 (M+H$^+$, C$_{24}$H$_{26}$NO$_4$, requires 392.1856).

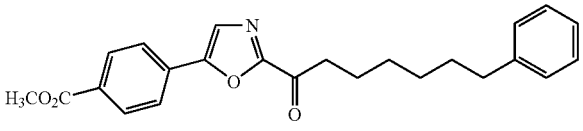

Example 24

Methyl 4-(2-(7-phenylheptanoyl)oxazol-5-yl)benzoate

Step 1; Methyl 4-(2-(1-(tert-butyldimethylsilyloxy)-7-phenylheptyl)oxazol-5-yl)benzoate. The title compound was prepared from 2-(1-(tert-butyldimethylsilyloxy)-7-phenylheptyl)-5-(tributylstannyl)oxazole (85 mg, 0.128 mmol) and methyl 4-bromobenzoate following General Procedure A. Flash chromatography (2-10% EtOAc/hexanes) yielded the title compound as a clear oil (44 mg, 68%): $^1$H NMR (CDCl$_3$, 500 MHz) δ 8.17 (d, 2H, J=8.5 Hz), 7.77 (d, 2H, J=8.5 Hz), 7.47 (s, 1H), 7.36-7.33 (m, 2H), 7.26-7.23 (m, 3H), 4.93 (t, 1H, J=6.0 Hz), 4.02 (s, 3H), 2.67 (t, 2H, J=7.5 Hz), 2.05-1.97 (m, 2H), 1.75-1.68 (m, 2H), 1.47-1.40 (m, 6H), 0.99 (s, 9H), 0.19 (s, 3H), 0.09 (s, 3H); $^{13}$C NMR (CDCl$_3$, 125 MHz) δ 166.9, 166.2, 150.6, 143.2, 132.5, 130.7, 130.0, 128.8, 128.6, 126.0, 124.3, 124.1, 69.1, 52.6, 36.8, 36.3, 31.8, 29.6, 26.2, 26.2, 25.5, 18.6, −4.5, −4.7.

Step 2. The title compound was prepared from methyl 4-(2-(1-(tert-butyldimethylsilyloxy)-7-phenylheptyl)oxazol-5-yl)benzoate (42 mg, 0.083 mmol) following General Procedure C. Flash chromatography (10% EtOAc/hexanes) yielded the title compound as a white solid (24 mg, 75%): $^1$H NMR (CDCl$_3$, 500 MHz) δ 8.20 (d, 2H, J=8.5 Hz), 7.92 (d, 2H, J=8.5 Hz), 7.69 (s, 1H), 7.36-7.33 (m, 2H), 7.26-7.25 (m, 3H), 3.17 (t, 2H, J=7.5 Hz), 2.69 (t, 2H, J=7.5 Hz), 1.89-1.83 (m, 2H), 1.75-1.69 (m, 2H), 1.54-1.46 (m, 4H); $^{13}$C NMR (CDCl$_3$, 125 MHz) δ 188.7, 166.6, 158.0, 153.4, 143.1, 131.5, 131.0, 130.8, 128.8, 128.7, 126.0, 125.7, 125.5, 52.8, 39.4, 36.3, 31.7, 29.4, 29.4, 24.4; MALDI-FTMS m/z 392.1855 (M+H$^+$, C$_{24}$H$_{26}$NO$_4$, requires 392.1856).

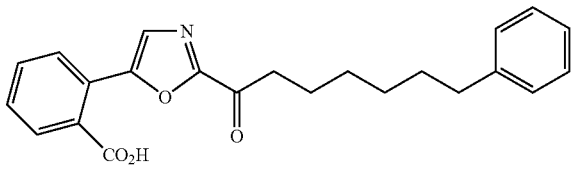

2-(2-(7-Phenylheptanoyl)oxazol-5-yl)benzoic acid

The title compound was prepared from methyl 2-(2-(7-phenylheptanoyl)oxazol-5-yl)benzoate (10 mg, 0.026 mmol) following General Procedure E. Preparative thin layer chromatography (EtOAc) yielded the title compound as a white solid (8 mg, 80%): $^1$H NMR (CD$_3$OD, 600 MHz) δ 7.62 (s, 1H), 7.22-7.19 (m, 2H), 7.14-7.09 (m, 3H), 3.04 (t, 2H, J=7.5 Hz), 2.58 (t, 2H, J=7.5 Hz), 1.71-1.68 (m, 2H), 1.62-1.59 (m, 2H), 1.41-1.32 (m, 4H); $^{13}$C NMR (CD$_3$OD, 150 MHz) δ 189.0, 159.4, 159.4, 143.3, 143.3, 134.6, 128.9, 128.7, 126.1, 39.6, 36.3, 32.0, 29.5, 29.4, 23.9; MALDI-FTMS m/z 378.1705 (M+H$^+$, C$_{23}$H$_{24}$NO$_4$, requires 378.1700).

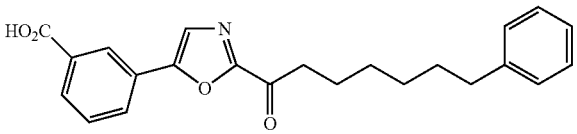

Example 25

3-(2-(7-Phenylheptanoyl)oxazol-5-yl)benzoic acid

The title compound was prepared from methyl 3-(2-(7-phenylheptanoyl)oxazol-5-yl)benzoate (29 mg, 0.074 mmol) following General Procedure E. Preparative thin layer chromatography (EtOAc) yielded the title compound as a white solid (22 mg, 79%): $^1$H NMR (THF-d$_8$, 500 MHz) δ 8.55 (s, 1H), 8.16 (d, 1H, J=7.5 Hz), 8.09 (d, 1H, J=8.0 Hz), 7.88 (s, 1H), 7.66 (t, 1H, J=8.0 Hz), 7.32-7.29 (m, 2H), 7.25-7.24 (m, 2H), 7.20-7.18 (m, 1H), 3.15 (t, 2H, J=7.0 Hz), 2.70 (t, 2H, J=7.5 Hz), 1.84-1.81 (m, 2H), 1.77-1.71 (m, 2H), 1.54-1.49 (m, 4H); $^{13}$C NMR (THF-d$_8$, 125 MHz) δ 187.2, 166.9, 158.0, 153.4, 142.9, 133.1, 130.9, 129.4, 128.9, 128.5, 128.4, 127.8, 126.4, 125.7, 124.8, 38.9, 36.1, 31.8, 29.4, 29.4, 24.2; MALDI-FTMS m/z 378.1699 (M+H$^+$, C$_{23}$H$_{24}$NO$_4$, requires 378.1700).

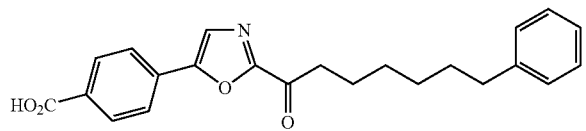

Example 26

4-(2-(7-Phenylheptanoyl)oxazol-5-yl)benzoic acid

The title compound was prepared from methyl 4-(2-(7-phenylheptanoyl)oxazol-5-yl)benzoate (10 mg, 0.026 mmol) following General Procedure E. Preparative thin layer chromatography (EtOAc) yielded the title compound as a white solid (8 mg, 83%): $^1$H NMR (THF-d$_8$, 500 MHz) δ 8.21 (d, 2H, J=8.5 Hz), 8.00 (d, 2H, J=8.5 Hz), 7.90 (s, 1H), 7.32-7.18 (m, 5H), 3.15 (t, 2H, J=7.5 Hz), 2.70 (t, 2H, J=7.5 Hz), 1.80-1.71 (m, 2H), 1.52-1.50 (m, 2H), 1.44-1.38 (m, 4H); $^{13}$C NMR (THF-d$_8$, 500 MHz) δ 187.3, 165.4, 158.2, 153.2, 142.9, 132.2, 131.1, 130.7, 128.5, 128.4, 126.9, 125.7, 125.1, 38.9, 36.1, 31.6, 31.6, 29.4, 24.1; MALDI-FTMS m/z 378.1697 (M+H$^+$, C$_{23}$H$_{24}$NO$_4$, requires 378.1700).

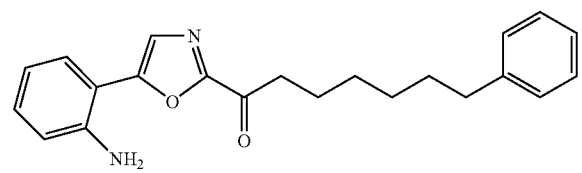

Example 27

1-(5-(2-Aminophenyl)oxazol-2-yl)-7-phenylheptan-1-one

Step 1; 2-(2-(1-(tert-Butyldimethylsilyloxy)-7-phenylheptyl)oxazol-5-yl)aniline. The title compound was prepared from 2-(1-(tert-butyldimethylsilyloxy)-7-phenylheptyl)-5-(tributylstannyl)oxazole (188 mg, 0.284 mmol) and 2-iodoaniline following General Procedure A. Flash chromatography (5-20% EtOAc/hexanes) yielded the title compound as a clear oil (122 mg, 90%): $^1$H NMR (CDCl$_3$, 400 MHz) δ 7.48 (dd, 1H, J=6.4, 9.3 Hz), 7.29-7.25 (m, 2H), 7.21 (s, 1H), 7.18-7.13 (m, 4H), 6.84-6.80 (m, 1H), 6.77-6.75 (m, 1H), 4.85 (t, 1H, J=6.0 Hz), 3.81 (br s, 2H), 2.60 (t, 2H, J=7.5 Hz), 1.97-1.89 (m, 2H), 1.68-1.59 (m, 2H), 1.40-1.29 (m, 6H), 0.91 (s, 9H), 0.11 (s, 3H), 0.00 (s, 3H); $^{13}$C NMR (CDCl$_3$, 100 MHz) δ 169.1, 155.2, 148.5, 147.9, 134.8, 133.5, 133.4, 132.5, 130.7, 127.8, 123.8, 121.9, 118.4, 73.8, 41.6, 41.1, 36.5, 34.3, 34.3, 30.9, 30.3, 23.3, 0.2, 0.0.

Step 2. The title compound was prepared from 2-(2-(1-(tert-butyldimethylsilyloxy)-7-phenylheptyl)oxazol-5-yl)aniline (74 mg, 0.159 mmol) following General Procedure D. Flash chromatography (10-20% EtOAc/hexanes) yielded the title compound as a yellow oil (3 mg, 5%): $^1$H NMR (CDCl$_3$, 500 MHz) δ 7.65 (dd, 1H, J=6.2, 9.0 Hz), 7.57 (s, 1H), 7.37-7.31 (m, 6H), 7.25 (m, 2H), 6.99-6.95 (m, 2H), 3.14 (t, 2H, J=7.5 Hz), 2.69 (t, 2H, J=7.5 Hz), 1.84-1.81 (m, 2H), 1.74-1.69 (m, 2H), 1.51-1.46 (m, 4H); $^{13}$C NMR (CDCl$_3$, 125 MHz) δ 188.5, 161.9, 156.9, 145.9, 143.1, 135.8, 131.6, 128.8, 128.7, 128.5, 126.0, 125.0, 120.1, 118.6, 39.3, 36.3, 31.7, 30.1, 29.4, 24.4; MALDI-FTMS m/z 349.1916 (M+H$^+$, C$_{22}$H$_{25}$N$_2$O$_2$, requires 349.1910).

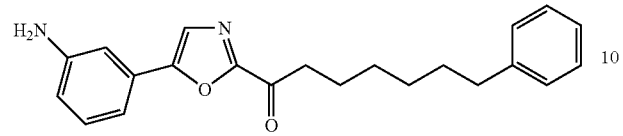

Example 28

1-(5-(3-Aminophenyl)oxazol-2-yl)-7-phenylheptan-1-one

The title compound was prepared from 1-(5-(3-nitrophenyl)oxazol-2-yl)-7-phenylheptan-1-one (22 mg, 0.159 mmol) following General Procedure F. Flash chromatography (10-30% EtOAc/hexanes) yielded the title compound as a yellow oil (10 mg, 40%): $^1$H NMR (CDCl$_3$, 500 MHz) δ 7.52 (s, 1H), 7.37-7.31 (m, 3H), 7.26-7.20 (m, 5H), 6.82 (d, 1H, J=6.5 Hz), 3.56 (br s, 2H), 3.15 (t, 2H, J=7.5 Hz), 2.69 (t, 2H, J=7.5 Hz), 1.88-1.82 (m, 2H), 1.75-1.69 (m, 2H), 1.55-1.46 (m, 4H); $^{13}$C NMR (CDCl$_3$, 125 MHz) δ 188.8, 157.4, 154.8, 147.1, 143.1, 130.5, 128.8, 128.7, 128.0, 126.0, 124.1, 117.2, 116.2, 111.9, 39.4, 36.3, 31.7, 29.5, 29.5, 24.5; MALDI-FTMS m/z 349.1915 (M+H$^+$, C$_{22}$H$_{25}$N$_2$O$_2$, requires 349.1910).

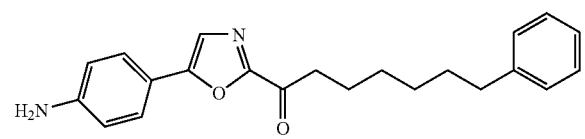

Example 29

1-(5-(4-Aminophenyl)oxazol-2-yl)-7-phenylheptan-1-one

The title compound was prepared from 1-(5-(4-nitrophenyl)oxazol-2-yl)-7-phenylheptan-1-one (9 mg, 0.024 mmol) following General Procedure F. Preparative thin layer chromatography (40% EtOAc/hexanes) yielded the title compound as a yellow oil (3 mg, 36%): $^1$H NMR (CD$_3$OD, 500 MHz) δ 8.07 (d, 2H, J=8.5 Hz), 7.90 (s, 1H), 7.56 (d, 2H, J=8.4 Hz), 7.32-7.29 (m, 2H), 7.25-7.20 (m, 3H), 3.16 (t, 2H, J=7.5 Hz), 2.69 (t, 2H, J=7.5 Hz), 1.84-1.81 (m, 2H), 1.75-1.70 (m, 2H), 1.53-1.47 (m, 4H); $^{13}$C NMR (CD$_3$OD, 125 MHz) δ 188.6, 157.8, 153.0, 142.9, 128.4, 128.3, 127.0, 126.1, 125.6, 124.9, 123.5, 118.8, 38.8, 35.8, 31.6, 29.0, 29.0, 23.9; MALDI-FTMS m/z 349.1898 (M+H$^+$, C$_{22}$H$_{25}$N$_2$O$_2$, requires 349.1910).

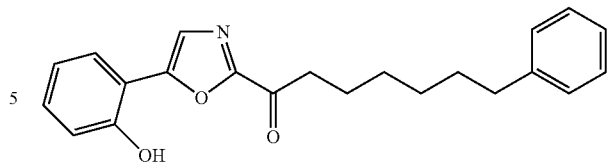

Example 30

1-(5-(2-Hydroxyphenyl)oxazol-2-yl)-7-phenylheptan-1-one

Step 1; 2-(2-(1-(tert-Butyldimethylsilyloxy)-7-phenylheptyl)oxazol-5-yl)phenol. The title compound was prepared from 2-(1-(tert-butyldimethylsilyloxy)-7-phenylheptyl)-5-(tributylstannyl)oxazole (88 mg, 0.134 mmol) and 2-iodophenol following General Procedure A. Flash chromatography (10-30% EtOAc/hexanes) yielded the title compound as a clear oil (21 mg, 34%): $^1$H NMR (CDCl$_3$, 500 MHz) δ 7.80-7.76 (m, 1H), 7.62 (s, 1H), 7.56 (br s, 1H), 7.36-7.20 (m, 6H), 7.09-7.04 (m, 2H), 4.94 (t, 1H, J=6.0 Hz), 2.62 (t, 2H, J=7.5 Hz), 2.05-1.93 (m, 2H), 1.68-1.65 (m, 2H), 1.47-1.32 (m, 6H), 0.97 (s, 9H), 0.17 (s, 3H), 0.07 (s, 3H); $^{13}$C NMR (CDCl$_3$, 125 MHz) δ 166.3, 154.3, 148.8, 143.2, 130.0, 128.8, 128.6, 126.5, 126.0, 124.9, 119.2, 116.8, 115.6, 70.1, 37.0, 35.3, 31.8, 29.6, 26.2, 26.2, 25.5, 18.6, −4.4, −4.6.

Step 2. The title compound was prepared from 2-(2-(1-(tert-butyldimethylsilyloxy)-7-phenylheptyl)oxazol-5-yl)phenol (44 mg, 0.094 mmol) following General Procedure D. Preparative thin layer chromatography (30% EtOAc) yielded the title compound as a white solid (3.4 mg, 12%): $^1$H NMR (CDCl$_3$, 500 MHz) δ 7.94-7.93 (m, 1H), 7.82 (br s, 1H), 7.38-7.34 (m, 4H), 7.26-7.25 (m, 3H), 7.12 (t, 1H, J=15.0 Hz), 7.00 (d, 1H, J=8.0 Hz), 3.18 (t, 2H, J=7.5 Hz), 2.69 (t, 2H, J=7.5 Hz), 1.89-1.83 (m, 2H), 1.75-1.69 (m, 2H), 1.54-1.46 (m, 4H); $^{13}$C NMR (CDCl$_3$, 125 MHz) δ 188.8, 153.4, 151.7, 143.1, 131.3, 128.8, 128.7, 127.7, 127.5, 126.0, 121.7, 116.9, 114.5, 39.4, 36.3, 31.7, 29.5, 29.4, 24.5; MALDI-FTMS m/z 350.1751 (M+H$^+$, C$_{22}$H$_{24}$NO$_3$, requires 350.1751).

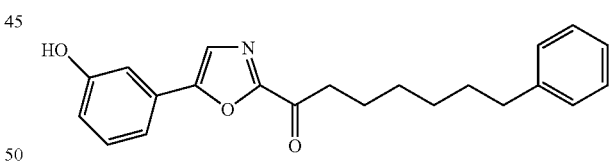

Example 31

1-(5-(3-Hydroxyphenyl)oxazol-2-yl)-7-phenylheptan-1-one

Step 1; 3-(2-(1-(tert-Butyldimethylsilyloxy)-7-phenylheptyl)oxazol-5-yl)phenol. The title compound was prepared from 2-(1-(tert-butyldimethylsilyloxy)-7-phenylheptyl)-5-(tributylstannyl)oxazole (99 mg, 0.149 mmol) and 3-iodophenol following General Procedure A. Flash chromatography (10-30% EtOAc/hexanes) yielded the title compound as a clear oil (29 mg, 41%): $^1$H NMR (CDCl$_3$, 500 MHz) δ 7.79-7.77 (m, 1H), 7.62 (s, 1H), 7.56 (br s, 1H), 7.39-7.35 (m, 2H), 7.29-7.24 (m, 4 H), 7.09-7.04 (m, 2H), 4.95 (t, 1H, J=6.0 Hz), 2.65 (t, 2H, J=7.5 Hz), 2.05-1.95 (m, 2H), 1.67-1.64 (m, 2H), 1.47-1.34 (m, 6H), 0.97 (s, 9H), 0.17 (s, 3H), 0.07 (s, 3H); $^{13}$C NMR (CDCl$_3$, 125 MHz) δ 164.3, 153.1, 148.8, 143.2, 129.7, 128.8, 128.6, 126.5, 126.0, 124.8, 121.0, 116.8, 115.6, 69.0, 37.0, 36.3, 31.8, 30.1, 26.2, 26.2, 25.5, 18.6, −4.5, −4.7.

Step 2. The title compound was prepared from 3-(2-(1-(tert-butyldimethylsilyloxy)-7-phenylheptyl)oxazol-5-yl) phenol (29 mg, 0.062 mmol) following General Procedure D. Preparative thin layer chromatography (30% EtOAc) yielded the title compound as a white solid (5.2 mg, 27%): $^1$H NMR (CD$_3$OD, 500 MHz) δ 7.74 (s, 1H), 7.38-7.37 (m, 2H), 7.32-7.29 (m, 3H), 7.24-7.23 (m, 2H), 7.21-7.20 (m, 1H), 6.95-6.94 (m, 1H), 3.14 (t, 2H, J=7.0 Hz), 2.69 (t, 2H, J=7.5 Hz), 1.85-1.79 (m, 2H), 1.75-1.69 (m, 2H), 1.54-1.42 (m, 4H); $^{13}$C NMR (CD$_3$OD, 125 MHz) δ 188.5, 158.4, 157.4, 154.7, 142.9, 130.5, 128.4, 128.2, 128.2, 125.6, 123.9, 117.2, 116.5, 111.7, 38.7, 35.8, 31.5, 29.0, 29.0, 23.9; MALDI-FTMS m/z 350.1752 (M+H$^+$, C$_{22}$H$_{24}$NO$_3$, requires 350.1751).

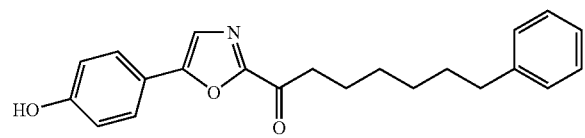

Example 32

1-(5-(4-Hydroxyphenyl)oxazol-2-yl)-7-phenylheptan-1-one

Step 1; 4-(2-(1-(tert-Butyldimethylsilyloxy)-7-phenylheptyl)oxazol-5-yl)phenyl acetate. The title compound was prepared from 2-(1-(tert-butyldimethylsilyloxy)-7-phenylheptyl)-5-(tributylstannyl)oxazole (74 mg, 0.112 mmol) and 4-iodophenyl acetate following General Procedure A. Flash chromatography (5-20% EtOAc/hexanes) yielded the title compound as a clear oil (31 mg, 54%): $^1$H NMR (CDCl$_3$, 600 MHz) δ 7.65 (d, 2H, J=7.8 Hz), 7.27-7.24 (m, 3H), 7.16-7.14 (m, 5H), 4.82 (t, 1H, J=6.0 Hz), 2.58 (t, 2H, J=7.5 Hz), 2.32 (s, 3H), 1.97-1.87 (m, 2H), 1.65-1.60 (m, 2H), 1.45-1.34 (m, 6H), 0.89 (s, 9H), 0.09 (s, 3H), −0.02 (s, 3H); $^{13}$C NMR (CDCl$_3$, 150 MHz) δ 170.2, 165.8, 151.4, 151.3, 143.7, 129.2, 129.1, 126.7, 126.4, 126.2, 123.1, 122.4, 69.5, 37.3, 36.8, 32.3, 30.0, 26.6, 26.6, 26.0, 22.1, 19.1, −4.1, −4.2.

Step 2. The title compound was prepared from 4-(2-(1-(tert-butyldimethylsilyloxy)-7-phenylheptyl)oxazol-5-yl) phenyl acetate (30 mg, 0.059 mmol) following General Procedure D except the reaction with Bu$_4$NF stirred for 5 h. Preparative thin layer chromatography (40% EtOAc) yielded the title compound as a white solid (2.4 mg, 10%): $^1$H NMR (CDCl$_3$, 600 MHz) δ 7.66 (d, 2H, J=8.4 Hz), 7.37 (s, 1H), 7.27-7.25 (m, 2H), 7.17-7.16 (m, 3H), 6.91 (d, 2H, J=8.4 Hz), 3.06 (t, 2H, J=7.5 Hz), 2.60 (t, 2H, J=7.5 Hz), 1.79-1.75 (m, 2H), 1.65-1.61 (m, 2H), 1.43-1.38 (m, 4H); $^{13}$C NMR (CD$_3$OD, 125 MHz) δ 188.7, 161.1, 159.2, 157.7, 143.1, 128.8, 128.7, 127.6, 126.0, 122.7, 120.0, 116.6, 39.3, 36.3, 31.7, 29.5, 29.4, 24.5; MALDI-FTMS m/z 350.1748 (M+H$^+$, C$_{22}$H$_{24}$NO$_3$, requires 350.1751).

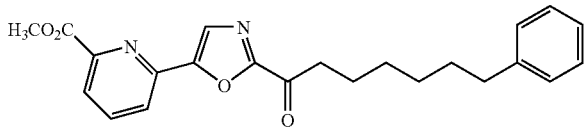

Example 33

Methyl 6-(2-(7-phenylheptanoyl)oxazol-5-yl)picolinate

Step 1; Methyl 6-(2-(1-(tert-butyldimethylsilyloxy)-7-phenylheptyl)oxazol-5-yl)picolinate. The title compound was prepared from 2-(1-(tert-butyldimethylsilyloxy)-7-phenylheptyl)-5-(tributylstannyl)oxazole (94 mg, 0.142 mmol) and methyl 6-chloropicolinate following General Procedure A. Flash chromatography (5-10% EtOAc/hexanes) yielded the title compound as a clear oil (72 mg, 100%): $^1$H NMR (CDCl$_3$, 500 MHz) δ 8.12-8.10 (m, 1H), 7.99 (t, 1H, J=7.8 Hz), 7.90-7.89 (m, 1H), 7.86 (s, 1H), 7.35-7.32 (m, 2H), 7.25-7.22 (m, 3H), 4.94 (t, 1H, J=7.0 Hz), 4.10 (s, 3H), 2.67 (t, 2H, J=7.5 Hz), 2.04-1.96 (m, 2H), 1.74-1.67 (m, 2H), 1.55-1.39 (m, 6H), 0.97 (s, 9H), 0.17 (s, 3H), 0.07 (s, 1H); $^{13}$C NMR (CDCl$_3$, 125 MHz) δ 166.5, 165.8, 150.3, 148.7, 148.2, 143.3, 138.4, 128.8, 128.6, 126.8, 126.0, 124.3, 122.5, 69.2, 53.4, 36.8, 36.3, 31.8, 29.6, 26.1, 26.1, 25.5, 14.0, −4.5, −4.7.

Step 2. The title compound was prepared from methyl 6-(2-(1-(tert-butyldimethylsilyloxy)-7-phenylheptyl)oxazol-5-yl)picolinate (70 mg, 0.138 mmol) following General Procedure C. Flash chromatography (10-30% EtOAc) yielded the title compound as a white solid (19 mg, 35%): $^1$H NMR (CDCl$_3$, 500 MHz) δ 8.19 (d, 1H, J=7.0 Hz), 8.12-8.09 (m, 2H), 8.06-8.03 (m, 1H), 7.36-7.33 (m, 2H), 7.26-7.24 (m, 3H), 4.11 (s, 3H), 3.19 (t, 2H, J=7.0 Hz), 2.69 (t, 2H, J=7.5 Hz), 1.89-1.83 (m, 2H), 1.75-1.69 (m, 2H), 1.55-1.47 (m, 4H); $^{13}$C NMR (CDCl$_3$, 125 MHz) δ 188.9, 165.5, 158.0, 152.7, 149.0, 147.0, 143.1, 138.7, 128.8, 128.7, 128.4, 126.0, 125.6, 123.7, 53.5, 39.6, 36.3, 31.7, 29.4, 29.4, 24.3; MALDI-FTMS m/z 393.1796 (M+H$^+$, C$_{23}$H$_{25}$N$_2$O$_4$, requires 393.1809).

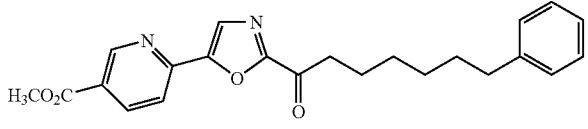

Example 34

Methyl 6-(2-(7-phenylheptanoyl)oxazol-5-yl)nicotinate

Step 1; Methyl 6-(2-(1-(tert-butyldimethylsilyloxy)-7-phenylheptyl)oxazol-5-yl)nicotinate. The title compound was prepared from 2-(1-(tert-butyldimethylsilyloxy)-7-phenylheptyl)-5-(tributylstannyl)oxazole (83 mg, 0.125 mmol) and methyl 6-chloronicotinate following General Procedure A. Flash chromatography (5-10% EtOAc/hexanes) yielded the title compound as a clear oil (46 mg, 72%): $^1$H NMR (CDCl$_3$, 500 MHz) δ 9.28 (d, 1H, J=2.0 Hz), 8.43 (dd, 1H, J=10.0, 6.0 Hz), 7.84 (s, 1H), 7.78 (d, 1H, J=8.5 Hz), 7.35-7.32 (m, 2H), 7.25-7.22 (m, 3H), 4.95 (t, 1H, J=7.0 Hz), 4.04

(s, 3H), 2.67 (t, 2H, J=7.5 Hz), 2.05-1.98 (m, 2H), 1.74-1.67 (m, 2H), 1.48-1.40 (m, 6H), 0.98 (s, 9H), 0.18 (s, 3H), 0.08 (s, 3H); $^{13}$C NMR (CDCl$_3$, 125 MHz) δ 167.1, 165.8, 151.6, 151.0, 150.5, 143.2, 138.5, 128.8, 128.6, 127.9, 126.0, 125.0, 118.7, 69.2, 52.9, 36.9, 36.3, 31.8, 29.6, 26.1, 26.1, 25.5, 18.6, −4.5, −4.7.

Step 2. The title compound was prepared from methyl 6-(2-(1-(tert-butyldimethylsilyloxy)-7-phenylheptyl)oxazol-5-yl)nicotinate (44 mg, 0.086 mmol) following General Procedure C. Flash chromatography (10-20% EtOAc) yielded the title compound as a white solid (19 mg, 56%): $^1$H NMR (CDCl$_3$, 500 MHz) δ 9.32 (d, 1H, J=2.0 Hz), 8.48 (dd, 1H, J=8.5, 2.0 Hz), 8.06 (s, 1H), 8.00 (d, 1H, J=8.5 Hz), 7.36-7.33 (m, 2H), 7.26-7.24 (m, 3H), 4.07 (s, 3H), 3.19 (t, 2H, J=7.0 Hz), 2.69 (t, 2H, J=7.5 Hz), 1.89-1.84 (m, 2H), 1.75-1.69 (m, 2H), 1.54-1.47 (m, 4H); $^{13}$C NMR (CDCl$_3$, 125 MHz) δ 188.9, 165.5, 158.2, 152.8, 151.7, 149.8, 143.1, 138.7, 129.1, 128.8, 128.7, 126.3, 126.0, 120.1, 53.0, 39.6, 36.3, 31.7, 29.4, 29.4, 24.3; MALDI-FTMS m/z 393.1811 (M+H$^+$, C$_{23}$H$_{25}$N$_2$O$_4$, requires 393.1809).

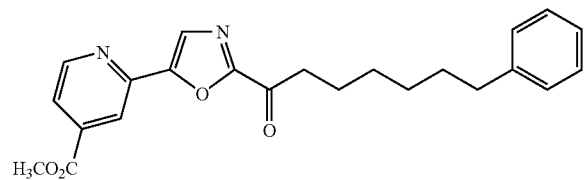

Example 35

Methyl 2-(2-(7-phenylheptanoyl)oxazol-5-yl)isonicotinate

Step 1; Methyl 2-(2-(1-(tert-butyldimethylsilyloxy)-7-phenylheptyl)oxazol-5-yl)isonicotinate. The title compound was prepared from 2-(1-(tert-butyldimethylsilyloxy)-7-phenylheptyl)-5-(tributylstannyl)oxazole (130 mg, 0.196 mmol) and methyl 2-chloroisonicotinate following General Procedure A. Flash chromatography (10% EtOAc/hexanes) yielded the title compound as a thick oil (72 mg, 71%): $^1$H NMR (CDCl$_3$, 400 MHz) δ 8.77 (d, 1H, J=5.0 Hz), 8.20 (s, 1H), 7.77 (dd, 1H, J=5.0, 1.5 Hz), 7.70 (s, 1H), 7.28-7.24 (m, 2H), 7.18-7.15 (m, 3H), 4.88 (dd, 1H, J=7.0, 5.9 Hz), 4.00 (s, 3H), 2.60 (t, 2H, J=7.8 Hz), 1.95 (m, 2H), 1.61 (m, 2H), 1.36 (m, 4H), 0.92 (s, 9H), 0.11 (s, 3H), 0.02 (s, 3H); $^{13}$C NMR (CDCl$_3$, 100 MHz) δ 166.2, 165.2, 150.7, 150.1, 148.4, 142.7, 138.3, 128.3, 128.2, 126.0, 125.5, 121.8, 118.3, 68.7, 52.8, 36.4, 35.9, 31.4, 29.1, 25.7, 25.7, 25.1, 18.2, −5.0, −5.1.

Step 2. The title compound was prepared from methyl 2-(2-(1-(tert-butyldimethylsilyloxy)-7-phenylheptyl)oxazol-5-yl)isonicotinate (36 mg, 0.071 mmol) following General Procedure C. Flash chromatography (30% EtOAc/hexanes) yielded the title compound as a white solid (15 mg, 56%): $^1$H NMR (CDCl$_3$, 400 MHz) δ 8.82 (dd, 1H, J=5.0, 0.9 Hz), 8.39 (d, 1H, J=0.9 Hz), 7.93 (s, 1H), 7.87 (dd, 1H, J=5.0, 1.4 Hz), 7.28-7.24 (m, 2H), 7.18-7.15 (m, 3H), 4.02 (s, 3H), 3.13 (t, 2H, J=7.5 Hz), 2.60 (t, 2H, J=7.8 Hz), 1.80 (quint, 2H, J=7.3 Hz), 1.65 (quint, 2H, J=7.4 Hz), 1.48-1.40 (m, 4H); $^{13}$C NMR (CDCl$_3$, 100 MHz) δ 188.5, 164.9, 157.6, 152.6, 151.0, 147.3, 142.7, 138.7, 128.4, 128.2, 127.6, 125.6, 123.2, 119.5, 53.0, 39.2, 35.8, 31.3, 29.0, 29.0, 23.9; MALDI-FTMS m/z 393.1811 (M+H$^+$, C$_{23}$H$_{25}$N$_2$O$_4$, requires 393.1809).

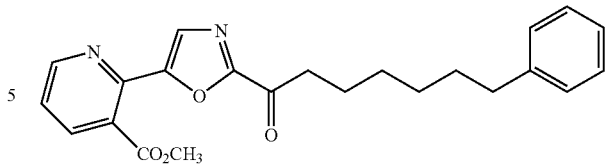

Example 36

Methyl 2-(2-(7-phenylheptanoyl)oxazol-5-yl)nicotinate

Step 1; Methyl 2-(2-(1-(tert-butyldimethylsilyloxy)-7-phenylheptyl)oxazol-5-yl)nicotinate. The title compound was prepared from 2-(1-(tert-butyldimethylsilyloxy)-7-phenylheptyl)-5-(tributylstannyl)oxazole (83 mg, 0.125 mmol) and methyl 2-chloronicotinate following General Procedure A. Flash chromatography (2-10% EtOAc/hexanes) yielded the title compound as a white solid (60 mg, 94%): $^1$H NMR (CDCl$_3$, 500 MHz) δ 8.80 (dd, 1H, J=6.4, 3.0 Hz), 8.02 (dd, 1H, J=10.0, 6.0 Hz), 7.72 (s, 1H), 7.39-7.32 (m, 3H), 7.25-7.23 (m, 3H), 4.91 (t, 1H, J=7.0 Hz), 4.01 (s, 3H), 2.66 (t, 2H, J=7.5 Hz), 2.03-1.91 (m, 2H), 1.74-1.68 (m, 2H), 1.46-1.35 (m, 6H), 0.96 (s, 9H), 0.17 (s, 3H), 0.05 (s, 3H); $^{13}$C NMR (CDCl$_3$, 125 MHz) δ 168.0, 166.5, 151.5, 149.9, 145.2, 143.2, 137.5, 128.8, 128.6, 128.0, 126.4, 126.0, 122.7, 69.1, 53.3, 37.0, 36.3, 31.8, 29.6, 26.2, 26.2, 25.5, 18.6, −4.5, −4.8.

Step 2. The title compound was prepared from methyl 2-(2-(1-(tert-butyldimethylsilyloxy)-7-phenylheptyl)oxazol-5-yl)nicotinate (30 mg, 0.059 mmol) following General Procedure C. Flash chromatography (10-30% EtOAc) yielded the title compound as a white solid (17 mg, 73%): $^1$H NMR (CDCl$_3$, 500 MHz) δ 8.85-8.84 (m, 1H), 8.10 (dd, 1H, J=8.0, 1.5 Hz), 7.94 (s, 1H), 7.49-7.47 (m, 1H), 7.36-7.33 (m, 2H), 7.26-7.25 (m, 3H), 4.07 (s, 3H), 3.17 (t, 2H, J=7.0 Hz), 2.69 (t, 2H, J=7.5 Hz), 1.88-1.82 (m, 2H), 1.75-1.69 (m, 2H), 1.53-1.47 (m, 4H); $^{13}$C NMR (CDCl$_3$, 125 MHz) δ 188.5, 167.6, 152.3, 151.8, 144.3, 143.1, 137.7, 129.5, 128.8, 128.7, 127.5, 126.0, 123.9, 53.7, 39.5, 36.3, 31.7, 29.4, 29.4, 24.2; MALDI-FTMS m/z 393.1799 (M+H$^+$, C$_{23}$H$_{25}$N$_2$O$_4$, requires 393.1809).

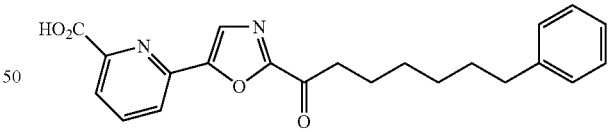

Example 37

6-(2-(7-Phenylheptanoyl)oxazol-5-yl)picolinic acid

The title compound was prepared from methyl 6-(2-(7-phenylheptanoyl)oxazol-5-yl)picolinate (9 mg, 0.059 mmol) following General Procedure E. Preparative thin layer chromatography (2% AcOH/EtOAc) yielded the title compound as a white solid (5 mg, 57%): $^1$H NMR (THF-d$_8$, 500 MHz) δ 8.11-8.04 (m, 4H), 7.22-7.08 (m, 5H), 3.08 (t, 2H, J=7.5 Hz), 2.61 (t, 2H, J=7.5 Hz), 1.76-1.68 (m, 2H), 1.68-1.62 (m, 2H), 1.45-1.41 (m, 4H); $^{13}$C NMR (THF-d$_8$, 125 MHz) δ 185.6, 163.1, 156.4, 151.4, 147.6, 144.7, 141.0, 137.1, 126.7, 126.5, 126.1, 123.9, 122.8, 121.1, 37.1, 34.3, 30.0, 27.6, 27.5, 22.2; MALDI-FTMS m/z 379.1645 (M+H$^+$, C$_{22}$H$_{23}$N$_2$O$_4$, requires 379.1652).

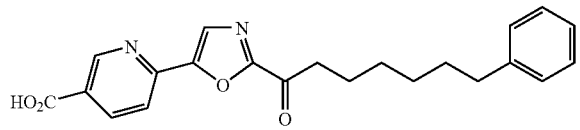

Example 38

6-(2-(7-Phenylheptanoyl)oxazol-5-yl)nicotinic acid

The title compound was prepared from methyl 6-(2-(7-phenylheptanoyl)oxazol-5-yl)nicotinate (10 mg, 0.025 mmol) following General Procedure E. Preparative thin layer chromatography (2% AcOH/EtOAc) yielded the title compound as a white solid (4 mg, 40%): $^1$H NMR (THF-d$_8$, 500 MHz) δ 9.18 (s, 1H), 8.41 (d, 1H, J=8.0 Hz), 7.97-7.94 (m, 2H), 7.22-7.09 (m, 5H), 3.08 (t, 2H, J=7.5 Hz), 2.61 (t, 2H, J=7.5 Hz), 1.74-1.69 (m, 2H), 1.67-1.61 (m, 2H), 1.47-1.40 (m, 4H); $^{13}$C NMR (THF-d$_8$, 125 MHz) δ 185.6, 163.6, 156.7, 151.1, 149.8, 147.9, 141.0, 136.7, 126.7, 126.5, 125.0, 123.9, 117.7, 37.2, 34.3, 29.9, 27.6, 27.5, 22.2; MALDI-FTMS m/z 379.1645 (M+H$^+$, C$_{22}$H$_{23}$N$_2$O$_4$, requires 379.1652).

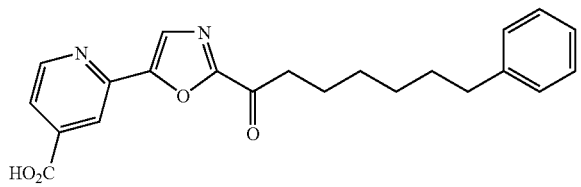

Example 39

2-(2-(7-Phenylheptanoyl)oxazol-5-yl)isonicotinic acid

The title compound was prepared from methyl 2-(2-(7-phenylheptanoyl)oxazol-5-yl)isonicotinate (12 mg, 0.025 mmol) following General Procedure E. Preparative thin layer chromatography (2% AcOH/EtOAc) yielded the title compound as a white solid (2 mg, 17%): $^1$H NMR (CDCl$_3$, 600 MHz) 8.85 (d, 1H, J=4.2 Hz), 8.42 (s, 1H), 7.93-7.90 (m, 2H), 7.26-7.30 (m, 2H), 7.17-7.16 (m, 3H), 3.12 (t, 2H, J=7.5 Hz), 2.61 (t, 2H, J=7.6 Hz), 1.79 (quint, 2H, J=7.4 Hz), 1.65 (quint, 2H, J=7.5 Hz), 1.44-1.40 (m, 4H); MALDI-FTMS m/z 377.1523 (M−H$^-$, C$_{22}$H$_{21}$N$_2$O$_4$, requires 377.1507).

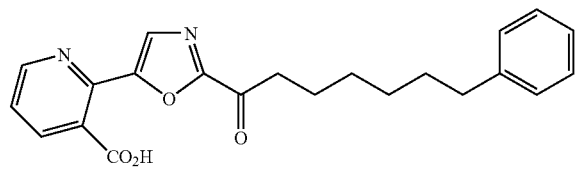

Example 40

2-(2-(7-Phenylheptanoyl)oxazol-5-yl)nicotinic acid

The title compound was prepared from methyl 2-(2-(7-phenylheptanoyl)oxazol-5-yl)nicotinate (8 mg, 0.020 mmol) following General Procedure E. Preparative thin layer chromatography (2% AcOH/EtOAc) yielded the title compound as a white solid (3 mg, 38%): $^1$H NMR (THF-d$_8$, 600 MHz) δ 8.71 (d, 1H, J=4.8 Hz), 8.09 (d, 1H, J=7.8 Hz), 7.79 (s, 1H), 7.45-7.44 (m, 2H), 7.22-7.19 (m, 2H), 7.16-7.14 (m, 2H), 7.11-7.08 (m, 1H), 3.05 (t, 2H, J=7.8 Hz), 2.60 (t, 2H, J=7.2 Hz), 1.73-1.69 (m, 2H), 1.66-1.61 (m, 2H), 1.43-1.39 (m, 4H); $^{13}$C NMR (THF-d$_8$, 150 MHz) δ 185.5, 165.6, 156.4, 150.9, 149.5, 142.7, 141.1, 135.7, 127.0, 126.7, 126.5, 125.9, 123.9, 121.9, 37.1, 24.3, 30.0, 27.6, 27.5, 22.2; MALDI-FTMS m/z 379.1646 (M+H$^+$, C$_{22}$H$_{23}$N$_2$O$_4$, requires 379.1652).

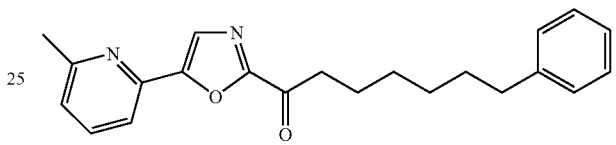

Example 41

1-(5-(6-Methylpyridin-2-yl)oxazol-2-yl)-7-phenyl-heptan-1-one

Step 1; 2-(1-(tert-Butyldimethylsilyloxy)-7-phenylheptyl)-5-(6-methylpyridin-2-yl)oxazole. The title compound was prepared from 2-(1-(tert-butyldimethylsilyloxy)-7-phenylheptyl)-5-(tributylstannyl)oxazole (70 mg, 0.106 mmol) and 2-bromo-6-methylpyridine following General Procedure A. Flash chromatography (10% EtOAc/hexanes) yielded the title compound as a white solid (26 mg, 57%): $^1$H NMR (CDCl$_3$, 400 MHz) δ 7.64 (s, 1H), 7.64 (t, 1H, J=7.6 Hz), 7.47 (d, 1H, J=7.6 Hz), 7.30-7.26 (m, 2H), 7.19-7.16 (m, 3H), 7.08 (d, 1H, J=7.6 Hz), 4.85 (dd, 1H, J=7.3, 5.8 Hz), 2.60 (t, 2H, J=7.6 Hz), 2.59 (s, 3H), 1.93 (m, 2H), 1.65 (m, 2H), 1.36 (m, 4H), 0.90 (s, 9H), 0.10 (s, 3H), 0.00 (s, 3H); $^{13}$C NMR (CDCl$_3$, 100 MHz) δ 165.4, 158.8, 150.9, 146.8, 142.8, 137.0, 128.4, 128.2, 125.5, 124.8, 122.5, 116.1, 68.7, 36.4, 35.9, 31.4, 29.1, 25.7, 25.7, 25.1, 24.5, 13.6, −5.0, −5.2.

Step 2. The title compound was prepared from 2-(1-(tert-butyldimethylsilyloxy)-7-phenylheptyl)-5-(6-methylpyridin-2-yl)oxazole (20 mg, 0.043 mmol) following General Procedure C. Flash chromatography (30% EtOAc/hexanes) yielded the title compound as a white solid (12 mg, 80%): $^1$H NMR (CDCl$_3$, 400 MHz) 7.87 (s, 1H), 7.69 (m, 2H), 7.30-7.26 (m, 2H), 7.19-7.16 (m, 4H), 3.11 (t, 2H, J=7.5 Hz), 2.62 (t, 2H, J=7.8 Hz), 2.61 (s, 3H), 1.78 (quint, 2H, J=7.4 Hz), 1.64 (quint, 2H, J=7.4 Hz), 1.51-1.34 (m, 4H); $^{13}$C NMR (CDCl$_3$, 100 MHz) δ 188.5, 159.2, 157.2, 153.6, 145.6, 142.7, 137.1, 128.4, 128.2, 126.6, 125.6, 123.9, 117.5, 39.0, 35.8, 31.3, 29.0, 29.0, 24.5, 23.9; MALDI-FTMS m/z 349.1917 (M+H$^+$, C$_{21}$H$_{23}$N$_2$O$_2$, requires 349.191).

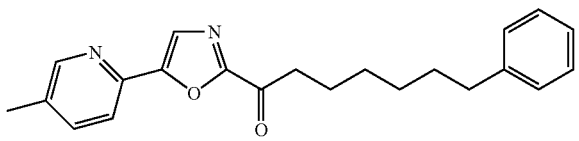

Example 42

1-(5-(5-Methylpyridin-2-yl)oxazol-2-yl)-7-phenyl-heptan-1-one

Step 1: 2-(1-(tert-Butyldimethylsilyloxy)-7-phenylheptyl)-5-(5-methylpyridin-2-yl)oxazole. The title compound was prepared from 2-(1-(tert-butyldimethylsilyloxy)-7-phenylheptyl)-5-(tributylstannyl)oxazole (100 mg, 0.106 mmol) and 2-bromo-5-methylpyridine following General Procedure A. Flash chromatography (10% EtOAc/hexanes) yielded the title compound as a thick oil (42 mg, 61%): $^1$H NMR (CDCl$_3$, 400 MHz) δ 7.64 (s, 1H), 7.64 (t, 1H, J=7.6 Hz), 7.47 (d, 1H, J=7.6 Hz), 7.30-7.26 (m, 2H), 7.19-7.16 (m, 3H), 7.08 (d, 1H, J=7.6 Hz), 4.85 (dd, 1H, J=7.3, 5.8 Hz), 2.60 (t, 2H, J=7.6 Hz), 2.59 (s, 3H), 1.93 (m, 2H), 1.65 (m, 2H), 1.36 (m, 4H), 0.90 (s, 9H), 0.10 (s, 3H), 0.00 (s, 3H); $^{13}$C NMR (CDCl$_3$, 100 MHz) δ 165.4, 158.8, 150.9, 146.8, 142.8, 137.0, 128.4, 128.2, 125.5, 124.8, 122.5, 116.1, 68.7, 36.4, 35.9, 31.4, 29.1, 25.7, 25.7, 25.1, 24.5, 13.6, −5.0, −5.2.

Step 2. The title compound was prepared from 2-(1-(tert-butyldimethylsilyloxy)-7-phenylheptyl)-5-(5-methylpyridin-2-yl)oxazole (20 mg, 0.043 mmol) following General Procedure C. Flash chromatography (30% EtOAc/hexanes) yielded the title compound as a white solid (8 mg, 89%): $^1$H NMR (CDCl$_3$, 400 MHz) 8.5 (s, 1H), 7.83 (s, 1H), 7.78 (d, 1H, J=7.9 Hz), 7.63 (dd, 1H, J=7.9, 2.0 Hz), 7.30-7.26 (m, 2H), 7.19-7.17 (m, 3H), 3.11 (t, 2H, J=7.5 Hz), 2.62 (t, 2H, J=7.6 Hz), 2.41 (s, 3H), 1.78 (m, 2H), 1.65 (m, 2H), 1.47 (m, 4H); $^{13}$C NMR (CDCl$_3$, 100 MHz) δ 188.6, 157.1, 153.5, 150.6, 143.7, 142.7, 137.5, 134.3, 128.4, 128.2, 126.2, 125.6, 120.0, 39.0, 35.9, 31.3, 29.0, 29.0, 24.0, 18.6; MALDI-FTMS m/z 349.1903 (M+H$^+$, C$_{21}$H$_{23}$N$_2$O$_2$, requires 349.191).

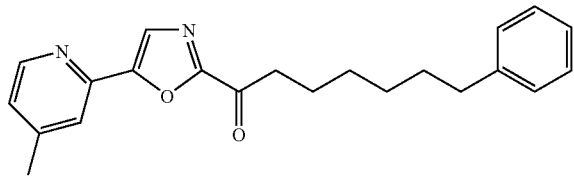

Example 43

1-(5-(4-Methylpyridin-2-yl)oxazol-2-yl)-7-phenyl-heptan-1-one

Step 1; 2-(1-(tert-Butyldimethylsilyloxy)-7-phenylheptyl)-5-(4-methylpyridin-2-yl)oxazole. The title compound was prepared from 2-(1-(tert-butyldimethylsilyloxy)-7-phenylheptyl)-5-(tributylstannyl)oxazole (130 mg, 0.196 mmol) and 2-bromo-4-methylpyridine following General Procedure A. Flash chromatography (10% EtOAc/hexanes) yielded the title compound as a thick oil (41 mg, 59%): $^1$H NMR (CDCl$_3$, 400 MHz) δ 8.48 (d, 1H, J=5 Hz), 7.63 (s, 1H), 7.50 (d, 1H, J=0.6 Hz), 7.29-7.25 (m, 2H), 7.18-7.15 (m, 3H), 7.05 (ddd, 1H, J=5.0, 1.5, 0.6 Hz), 4.86 (dd, 1H, J=7.3, 5.8 Hz), 2.59 (t, 2H, J=7.8 Hz), 2.41 (s, 3H), 1.93 (m, 2H), 1.61 (m, 2H), 1.36 (m, 4H), 0.91 (s, 9H), 0.11 (s, 3H), 0.01 (s, 3H); $^{13}$C NMR (CDCl$_3$, 100 MHz) δ 165.5, 150.7, 149.6, 148.1, 147.2, 142.7, 128.2, 125.5, 125.0, 123.8, 119.9, 68.7, 36.4, 35.9, 31.4, 29.1, 25.7, 25.7, 25.1, 21.1, 18.2, −5.0, −5.2.

Step 2. The title compound was prepared from 2-(1-(tert-butyldimethylsilyloxy)-7-phenylheptyl)-5-(4-methylpyridin-2-yl)oxazole (27 mg, 0.058 mmol) following General Procedure C. Flash chromatography (30% EtOAc/hexanes) yielded the title compound as a white solid (16 mg, 84%): $^1$H NMR (CDCl$_3$, 400 MHz) 8.52 (d, 1H, J=5.0 Hz), 7.87 (s, 1H), 7.72 (d, 1H, J=0.9 Hz), 7.30-7.26 (m, 2H), 7.19-7.16 (m, 4H), 7.14 (dd, 1H, J=5.0, 0.6 Hz), 3.11 (t, 2H, J=7.5 Hz), 2.62 (t, 2H, J=7.6 Hz), 2.44 (s, 3H), 1.79 (quint, 2H, J=7.4 Hz), 1.65 (quint, 2H, J=7.5 Hz), 1.51-1.34 (m, 4H); $^{13}$C NMR (CDCl$_3$, 100 MHz) δ 188.6, 157.2, 153.4, 149.8, 148.6, 146.0, 142.7, 128.4, 128.2, 126.7, 125.6, 125.1, 121.3, 39.0, 35.8, 31.3, 29.0, 29.0, 23.9, 21.1; MALDI-FTMS m/z 349.1904 (M+H$^+$, C$_{21}$H$_{23}$N$_2$O$_2$, requires 349.191).

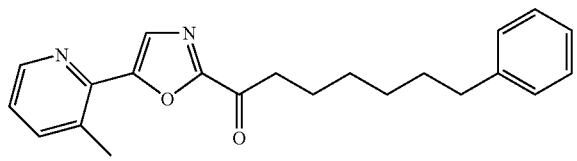

Example 44

1-(5-(3-Methylpyridin-2-yl)oxazol-2-yl)-7-phenyl-heptan-1-one

Step 1; 2-(1-(tert-Butyldimethylsilyloxy)-7-phenylheptyl)-5-(3-methylpyridin-2-yl)oxazole. The title compound was prepared from 2-(1-(tert-butyldimethylsilyloxy)-7-phenylheptyl)-5-(tributylstannyl)oxazole (130 mg, 0.196 mmol) and 2-bromo-3-methylpyridine following General Procedure A. Flash chromatography (10% EtOAc/hexanes) yielded the title compound as a thick oil (28 mg, 40%): $^1$H NMR (CDCl$_3$, 400 MHz) δ 8.52 (dd, 1H, J=4.7, 1.5 Hz), 7.57 (ddd, 1H, J=7.6, 1.4, 0.6 Hz), 7.55 (s, 1H), 7.29-7.24 (m, 2H), 7.18-7.15 (m, 4H), 4.89 (dd, 1H, J=7.6, 5.9 Hz), 2.59 (t, 2H, J=7.8 Hz), 2.55 (s, 3H), 1.93 (m, 2H), 1.61 (m, 2H), 1.36 (m, 4H), 0.89 (s, 9H), 0.10 (s, 3H), −0.02 (s, 3H); $^{13}$C NMR (CDCl$_3$, 100 MHz) δ 165.6, 150.9, 147.1, 146.0, 142.8, 139.3, 130.3, 128.3, 128.2, 127.1, 125.5, 122.6, 68.6, 36.5, 35.9, 31.4, 29.1, 25.7, 25.7, 25.1, 20.4, 18.2, −5.0, −5.2.

Step 2. The title compound was prepared from 2-(1-(tert-butyldimethylsilyloxy)-7-phenylheptyl)-5-(3-methylpyridin-2-yl)oxazole (25 mg, 0.097 mmol) following General Procedure C. Flash chromatography (30% EtOAc/hexanes) yielded the title compound as a white solid (13 mg, 70%): $^1$H NMR (CDCl$_3$, 500 MHz) δ 8.55 (dd, 1H, J=4.4, 1.1 Hz), 7.82 (s, 1H), 7.62 (dd, 1H, J=7.7, 1.1 Hz), 7.29-7.23 (m, 3H), 7.19-7.16 (m, 3H), 3.12 (t, 2H, J=7.5 Hz), 2.64 (s, 3H), 2.62 (t, 2H, J=7.9 Hz), 1.79 (quint, 2H, J=7.6 Hz), 1.65 (quint, 2H, J=7.5 Hz), 1.51-1.34 (m, 4H); $^{13}$C NMR (CDCl$_3$, 125 MHz) δ 188.3, 157.4, 153.9, 147.4, 144.9, 142.7, 139.6, 131.7, 128.7, 128.4, 128.2, 125.6, 123.8, 39.1, 35.8, 31.2, 29.0, 29.0, 23.9, 20.1; MALDI-FTMS m/z 349.1913 (M+H$^+$, C$_{21}$H$_{23}$N$_2$O$_2$, requires 349.191).

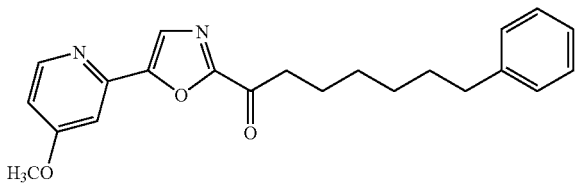

Example 45

1-(5-(4-Methoxypyridin-2-yl)oxazol-2-yl)-7-phenyl-heptan-1-one

Step 1; 2-(1-(tert-Butyldimethylsilyloxy)-7-phenylheptyl)-5-(4-methoxypyridin-2-yl)oxazole. The title compound was prepared from 2-(1-(tert-butyldimethylsilyloxy)-7-phenylheptyl)-5-(tributylstannyl)oxazole (144 mg, 0.302 mmol) and 2-chloro-4-methoxypyridine following General Procedure A. Flash chromatography (10% EtOAc/hexanes) yielded the title compound as a thick oil (88 mg, 61%): $^1$H NMR (CDCl$_3$, 400 MHz) δ 8.43 (d, 1H, J=5.6 Hz), 7.63 (s, 1H), 7.28-7.24 (m, 2H), 7.18-7.15 (m, 3H), 6.75 (dd, 1H, J=5.8, 2.6 Hz), 4.85 (dd, 1H, J=7.3, 5.8 Hz), 3.9 (s, 3H), 2.59 (t, 2H, J=7.6 Hz), 1.93 (m, 2H), 1.61 (m, 2H), 1.36 (m, 4H), 0.90 (s, 9H), 0.10 (s, 3H), 0.01 (s, 3H); $^{13}$C NMR (CDCl$_3$, 100 MHz) δ 166.3, 165.5, 151.1, 150.6, 148.9, 142.7, 128.3, 128.2, 125.5, 125.3, 109.0, 105.1, 68.7, 55.3, 36.4, 35.9, 31.4, 29.1, 25.7, 25.7, 25.1, 18.2, −5.0, −5.1.

Step 2. The title compound was prepared from 2-(1-(tert-butyldimethylsilyloxy)-7-phenylheptyl)-5-(4-methoxypyridin-2-yl)oxazole (70 mg, 0.146 mmol) following General Procedure C. Flash chromatography (30% EtOAc/hexanes) yielded the title compound as a white solid (51 mg, 96%): $^1$H NMR (CDCl$_3$, 400 MHz) δ 8.49 (d, 1H, J=5.3 Hz), 7.88 (s, 1H), 7.39 (d, 1H, J=2.3 Hz), 7.29-7.26 (m, 2H), 7.19-7.16 (m, 3H), 6.84 (dd, 1H, J=5.9, 2.6 Hz), 3.94 (s, 3H), 3.12 (t, 2H, J=7.5 Hz), 2.62 (t, 2H, J=7.8 Hz), 1.79 (quint, 2H, J=7.3 Hz), 1.65 (quint, 2H, J=7.9 Hz), 1.47-1.39 (m, 4H); $^{13}$C NMR (CDCl$_3$, 100 MHz) δ 188.6, 175.3, 166.6, 157.2, 153.1, 151.3, 147.6, 142.7, 128.4, 128.2, 127.1, 125.6, 110.5, 106.4, 55.6, 39.1, 35.9, 31.3, 29.0, 23.9, 20.6; MALDI-FTMS m/z 365.1863 (M+H$^+$, C$_{22}$H$_{25}$N$_2$O$_3$, requires 365.186).

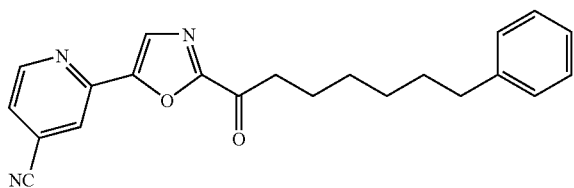

Example 46

2-(2-(7-Phenylheptanoyl)oxazol-5-yl)isonicotinonitrile

Step 1; 2-(2-(1-(tert-Butyldimethylsilyloxy)-7-phenylheptyl)oxazol-5-yl)isonicotinonitrile. The title compound was prepared from 2-(1-(tert-butyldimethylsilyloxy)-7-phenylheptyl)-5-(tributylstannyl)oxazole (110 mg, 0.166 mmol) and 2-chloro-4-cyanopyridine following General Procedure A. Flash chromatography (10% EtOAc/hexanes) yielded the title compound as a thick oil (72 mg, 75%): $^1$H NMR (CDCl$_3$, 400 MHz) δ 8.79 (dd, 1H, J=5.0, 0.9 Hz), 7.84 (s, 1H), 7.74 (s, 1H), 7.43 (dd, 1H, J=5.0, 1.4 Hz), 7.28-7.24 (m, 2H), 7.18-7.15 (m, 3H), 4.88 (dd, 1H, J=7.3, 6.6 Hz), 2.60 (t, 2H, J=7.8 Hz), 1.93 (m, 2H), 1.61 (m, 2H), 1.36 (m, 4H), 0.91 (s, 9H), 0.12 (s, 3H), 0.01 (s, 3H); $^{13}$C NMR (CDCl$_3$, 100 MHz) δ 166.7, 150.8, 149.0, 148.6, 142.7, 128.3, 128.2, 127.1, 125.5, 123.7, 121.4, 120.2, 116.1, 68.6, 36.4, 35.8, 31.3, 29.0, 25.6, 25.6, 25.0, 18.1, −5.0, −5.2.

Step 2. The title compound was prepared from 2-(2-(1-(tert-butyldimethylsilyloxy)-7-phenylheptyl)oxazol-5-yl)isonicotinonitrile (46 mg, 0.097 mmol) following General Procedure C. Flash chromatography (30% EtOAc/hexanes) yielded the title compound as a white solid (24 mg, 69%): $^1$H NMR (CDCl$_3$, 400 MHz) δ 8.84 (d, 1H, J=5.0 Hz), 8.07 (s, 1H), 7.96 (s, 1H), 7.53 (d, 1H, J=5.0, 1.5 Hz), 7.29-7.26 (m, 2H), 7.19-7.16 (m, 3H), 6.84 (dd, 1H, J=5.9, 2.6 Hz), 3.12 (t, 2H, J=7.5 Hz), 2.62 (t, 2H, J=7.6 Hz), 1.80 (quint, 2H, J=7.2 Hz), 1.65 (quint, 2H, J=7.3 Hz), 1.42 (m, 4H); $^{13}$C NMR (CDCl$_3$, 100 MHz) δ 188.3, 157.8, 151.3, 151.1, 147.6, 142.6, 128.5, 128.4, 128.2, 125.6, 125.2, 121.8, 121.5, 115.7, 39.2, 35.8, 31.2, 28.9, 23.8; MALDI-FTMS m/z 360.1717 (M+H$^+$, C$_{22}$H$_{22}$N$_3$O$_2$, requires 360.1706).

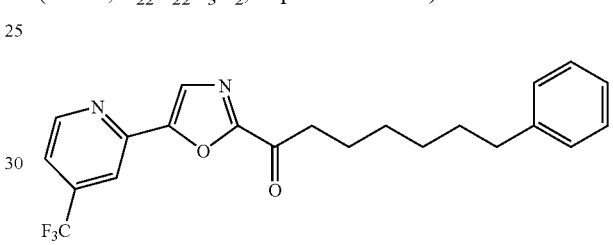

Example 47

7-Phenyl-1-(5-(4-(trifluoromethyl)pyridin-2-yl)oxazol-2-yl)heptan-1-one

Step 1; 2-(1-(tert-Butyldimethylsilyloxy)-7-phenylheptyl)-5-(4-(trifluoromethyl)pyridin-2-yl)oxazole. The title compound was prepared from 2-(1-(tert-butyldimethylsilyloxy)-7-phenylheptyl)-5-(tributylstannyl)oxazole (130 mg, 0.196 mmol) and 2-chloro-4-(trifluoromethyl)pyridine following General Procedure A. Flash chromatography (10% EtOAc/hexanes) yielded the title compound as a thick oil (80 mg, 77%): $^1$H NMR (CDCl$_3$, 400 MHz) δ 8.79 (d, 1H, J=5.0 Hz), 7.84 (s, 1H), 7.73 (s, 1H), 7.43 (dd, 1H, J=5.0, 0.9 Hz), 7.28-7.24 (m, 2H), 7.18-7.15 (m, 3H), 4.88 (dd, 1H, J=7.3, 5.9 Hz), 2.60 (t, 2H, J=7.8 Hz), 1.93 (m, 2H), 1.61 (m, 2H), 1.36 (m, 4H), 0.91 (s, 9H), 0.11 (s, 3H), 0.01 (s, 3H); $^{13}$C NMR (CDCl$_3$, 100 MHz) δ 166.5, 150.9, 149.6, 148.6, 142.8, 139.3 (q, J=33.9 Hz), 128.4, 128.2, 126.6, 125.6, 118.1 (q, J=3.5 Hz), 114.6 (q, J=3.0 Hz), 68.7, 36.4, 35.9, 31.4, 29.1, 25.7, 25.7, 18.2, −5.0, −5.1.

Step 2. The title compound was prepared from 2-(1-(tert-butyldimethylsilyloxy)-7-phenylheptyl)-5-(4-(trifluoromethyl)pyridin-2-yl)oxazole (51 mg, 0.098 mmol) following General Procedure C. Flash chromatography (30% EtOAc/hexanes) yielded the title compound as a white solid (32 mg, 80%): $^1$H NMR (CDCl$_3$, 400 MHz) δ 8.85 (d, 1H, J=5.0 Hz), 8.06 (s, 1H), 7.96 (s, 1H), 7.54 (d, 1H, J=5.0 Hz), 7.29-7.26 (m, 2H), 7.19-7.16 (m, 3H), 3.13 (t, 2H, J=7.5 Hz), 2.62 (t, 2H, J=7.8 Hz), 1.80 (quint, 2H, J=7.4 Hz), 1.65 (quint, 2H, J=7.8 Hz), 1.47-1.40 (m, 4H); $^{13}$C NMR (CDCl$_3$, 100 MHz) δ 188.5, 157.7, 152.0, 151.1, 147.5, 142.6, 139.6 (q, J=34.9

Hz), 128.4, 128.2, 128.0, 125.6, 123.7, 121.0, 119.4 (q, J=3.0 Hz), 115.9 (q, J=4.6 Hz), 39.2, 35.8, 31.2, 29.0, 29.0, 23.9; MALDI-FTMS m/z 403.1628 (M+H$^+$, $C_{22}H_{22}F_3N_2O_2$, requires 403.1628).

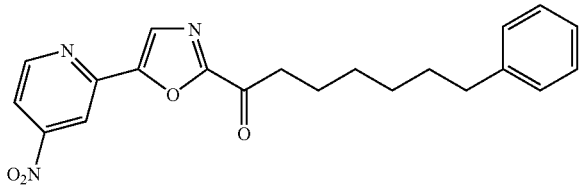

Example 48

1-(5-(4-Nitropyridin-2-yl)oxazol-2-yl)-7-phenylheptan-1-one

Step 1; 2-(1-(tert-Butyldimethylsilyloxy)-7-phenylheptyl)-5-(4-nitropyridin-2-yl)oxazole. The title compound was prepared from 2-(1-(tert-butyldimethylsilyloxy)-7-phenylheptyl)-5-(tributylstannyl)oxazole (190 mg, 0.287 mmol) and 2-chloro-4-nitropyridine following General Procedure A. Flash chromatography (10% EtOAc/hexanes) yielded the title compound as a thick oil (98 mg, 66%): $^1$H NMR (CDCl$_3$, 400 MHz) δ 8.91 (dd, 1H, J=5.3, 0.6 Hz), 8.33 (d, 1H, J=2.1), 7.93 (dd, 1H, J=5.3, 2.1 Hz), 7.78 (s, 1H), 7.28-7.24 (m, 2H), 7.18-7.15 (m, 3H), 4.90 (dd, 1H, J=7.3, 5.8 Hz), 2.60 (t, 2H, J=7.8 Hz), 1.96 (m, 2H), 1.62 (m, 2H), 1.36 (m, 4H), 0.92 (s, 9H), 0.12 (s, 3H), 0.03 (s, 3H); $^{13}$C NMR (CDCl$_3$, 100 MHz) δ 166.9, 154.6, 152.2, 150.1, 149.1, 142.7, 128.3, 128.2, 127.5, 125.5, 114.8, 111.4, 68.7, 36.4, 35.9, 31.3, 29.1, 25.7, 25.7, 25.0, 18.2, −5.0, −5.1.

Step 2. The title compound was prepared from 2-(1-(tert-butyldimethylsilyloxy)-7-phenylheptyl)-5-(4-nitropyridin-2-yl)oxazole (88 mg, 0.178 mmol) following General Procedure C. Flash chromatography (30% EtOAc/hexanes) yielded the title compound as a white solid (40 mg, 63%): $^1$H NMR (CDCl$_3$, 400 MHz) δ 8.96 (dd, 1H, J=5.8, 0.6 Hz), 8.53 (d, 1H, J=2.0 Hz), 8.03 (dd, 1H, J=5.3, 2.1 Hz), 8.00 (s, 1H), 7.28-7.24 (m, 2H), 7.18-7.15 (m, 3H), 3.14 (t, 2H, J=7.5 Hz), 2.62 (t, 2H, J=7.8 Hz), 1.81 (quint, 2H, J=7.3 Hz), 1.65 (quint, 2H, J=7.4 Hz), 1.48-1.40 (m, 4H); $^{13}$C NMR (CDCl$_3$, 100 MHz) δ 188.3, 157.8, 154.6, 152.4, 151.3, 149.0, 128.7, 128.3, 128.2, 125.6, 116.1, 112.7, 39.2, 35.8, 31.2, 28.9, 28.9, 23.8; MALDI-FTMS m/z 380.1609 (M+H$^+$, $C_{21}H_{22}N_3O_4$, requires 380.1605).

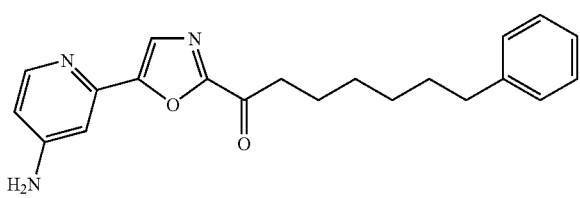

Example 49

1-(5-(4-Aminopyridin-2-yl)oxazol-2-yl)-7-phenylheptan-1-one

The title compound was prepared from 1-(5-(4-nitropyridin-2-yl)oxazol-2-yl)-7-phenylheptan-1-one (8 mg, 0.021 mmol) following General Procedure F. Flash chromatography (50% EtOAc/hexanes) yielded the title compound as a white solid (6 mg, 80%): $^1$H NMR (CDCl$_3$/CD$_3$OD, 400 MHz) δ 8.26 (d, 1H, J=5.6 Hz), 7.82 (s, 1H), 7.35 (d, 1H, J=2.1 Hz), 7.28-7.24 (m, 2H), 7.18-7.15 (m, 3H), 6.78 (dd, 1H, J=5.9, 2.4 Hz), 3.07 (t, 2H, J=7.3 Hz), 2.58 (t, 2H, J=7.8 Hz), 1.74 (quint, 2H, J=7.3 Hz), 1.60 (quint, 2H, J=7.3 Hz), 1.48-1.40 (m, 4H); $^{13}$C NMR (CDCl$_3$/CD$_3$OD, 100 MHz) δ 189.0, 158.0, 157.0, 153.3, 149.8, 128.3, 128.1, 126.7, 125.5, 107.6, 104.3, 38.9, 35.7, 31.2, 28.9, 28.9, 23.8; MALDI-FTMS m/z 350.1862 (M+H$^+$, $C_{21}H_{22}N_3O_4$, requires 350.1863).

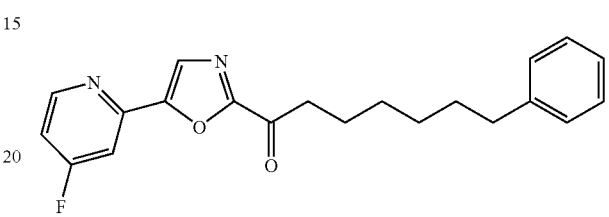

Example 50

1-(5-(4-Nitropyridin-2-yl)oxazol-2-yl)-7-phenylheptan-1-one

Step 1: 2-(1-(tert-Butyldimethylsilyloxy)-7-phenylheptyl)-5-(4-fluoropyridin-2-yl)oxazole. The title compound was prepared from 2-(1-(tert-butyldimethylsilyloxy)-7-phenylheptyl)-5-(tributylstannyl)oxazole (130 mg, 0.196 mmol) and 2-chloro-4-fluoropyridine following General Procedure A. Flash chromatography (10% EtOAc/hexanes) yielded the title compound as a thick oil (48 mg, 51%): $^1$H NMR (CDCl$_3$, 400 MHz) δ 8.59 (dd, 1H, J=8.5, 5.6 Hz), 7.69 (s, 1H), 7.38 (dd, 1H, J=9.4, 2.3 Hz), 7.28-7.24 (m, 2H), 7.18-7.15 (m, 3H), 6.96 (ddd, 1H, J=8.2, 5.6, 2.4 Hz), 4.87 (dd, 1H, J=7.0, 6.2 Hz), 2.60 (t, 2H, J=7.6 Hz), 1.96 (m, 2H), 1.62 (m, 2H), 1.36 (m, 4H), 0.91 (s, 9H), 0.11 (s, 3H), 0.01 (s, 3H); $^{13}$C NMR (CDCl$_3$, 100 MHz) δ 170.4, 167.8, 166.1, 152.4 (d, J=7.6 Hz), 150.2, (d, J=7.6 Hz), 149.8 (d, J=4.6 Hz), 142.7, 128.3, 128.2, 126.2, 125.5, 110.5 (d, J=15.2 Hz), 106.9 (d, J=18.2 Hz), 68.7, 36.4, 35.9, 31.4, 29.1, 25.7, 25.7, 25.1, 18.2, −5.0, −5.2.

Step 2. The title compound was prepared from 2-(1-(tert-butyldimethylsilyloxy)-7-phenylheptyl)-5-(4-fluoropyridin-2-yl)oxazole (44 mg, 0.094 mmol) following General Procedure C. Flash chromatography (30% EtOAc/hexanes) yielded the title compound as a white solid (23 mg, 70%): $^1$H NMR (CDCl$_3$, 400 MHz) δ 8.63 (dd, 1H, J=7.9, 5.6 Hz), 7.90 (d, 1H, J=0.9 Hz), 7.60 (dd, 1H, J=9.4, 2.4 Hz), 7.28-7.24 (m, 2H), 7.18-7.15 (m, 3H), 6.96 (dddd, 1H, J=7.4, 5.6, 2.4, 0.6 Hz), 3.11 (t, 2H, J=7.3 Hz), 2.62 (t, 2H, J=7.6 Hz), 1.79 (quint, 2H, J=7.3 Hz), 1.67 (quint, 2H, J=7.3 Hz), 1.48-1.40 (m, 4H); $^{13}$C NMR (CDCl$_3$, 100 MHz) δ 188.4, 170.4, 167.8, 157.5, 152.6 (d, J=6.1 Hz), 152.2, (d, J=4.6 Hz), 149.0 (d, J=7.6 Hz), 142.6, 128.4, 128.2, 127.7, 125.6, 111.8 (d, J=16.7 Hz), 108.4 (d, J=19.7 Hz), 39.1, 35.8, 31.2, 28.9, 28.9, 23.8; MALDI-FTMS m/z 353.1681 (M+H$^+$, $C_{21}H_{22}FN_2O_2$, requires 353.1665).

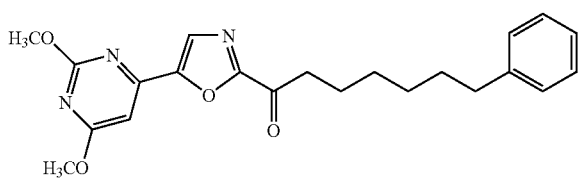

Example 51

1-(5-(2,6-Dimethoxypyrimidin-4-yl)oxazol-2-yl)-7-phenylheptan-1-one

Step 1; 2-(1-(tert-Butyldimethylsilyloxy)-7-phenylheptyl)-5-(2,6-dimethoxypyrimidin-4-yl)oxazole. The title compound was prepared from 2-(1-(tert-butyldimethylsilyloxy)-7-phenylheptyl)-5-(tributylstannyl)oxazole (200 mg, 0.302 mmol) and 6-chloro-2,4-dimethoxypyrimidine following General Procedure A. Flash chromatography (10% EtOAc/hexanes) yielded the title compound as a thick oil (138 mg, 90%): $^1$H NMR (CDCl$_3$, 400 MHz) δ 7.73 (s, 1H), 7.28-7.24 (m, 2H), 7.18-7.15 (m, 3H), 6.67 (s, 1H), 4.85 (dd, 1H, J=7.3, 5.9 Hz), 4.03 (s, 3H), 4.00 (s, 3H), 2.59 (t, 2H, J=7.6 Hz), 1.96 (m, 2H), 1.62 (m, 2H), 1.36 (m, 4H), 0.90 (s, 9H), 0.10 (s, 3H), 0.00 (s, 3H); $^{13}$C NMR (CDCl$_3$, 100 MHz) δ 172.3, 166.6, 165.4, 155.2, 149.0, 142.6, 128.3, 128.1, 128.0, 125.5, 95.8, 68.6, 54.8, 53.9, 36.2, 35.8, 31.3, 29.0, 25.6, 25.6, 24.9, 18.1, −5.1, −5.2.

Step 2. The title compound was prepared from 2-(1-(tert-butyldimethylsilyloxy)-7-phenylheptyl)-5-(2,6-dimethoxypyrimidin-4-yl)oxazole (130 mg, 0.254 mmol) following General Procedure C. Flash chromatography (30% EtOAc/hexanes) yielded the title compound as a white solid (88 mg, 88%): $^1$H NMR (CDCl$_3$, 400 MHz) δ 7.94 (s, 1H), 7.28-7.24 (m, 2H), 7.18-7.15 (m, 3H), 6.88 (s, 1H), 4.07 (s, 3H), 4.04 (s, 3H), 3.11 (t, 2H, J=7.3 Hz), 2.63 (t, 2H, J=7.7 Hz), 1.80 (quint, 2H, J=7.7 Hz), 1.66 (quint, 2H, J=7.5 Hz), 1.48-1.40 (m, 4H); $^{13}$C NMR (CDCl$_3$, 100 MHz) δ 188.3, 172.5, 165.5, 157.7, 154.1, 142.5, 129.1, 128.3, 128.3, 128.1, 125.5, 97.4, 54.9, 54.2, 39.1, 35.7, 31.1, 28.9, 28.9, 23.7; MALDI-FTMS m/z 396.1913 (M+H$^+$, C$_{22}$H$_{26}$N$_3$O$_4$, requires 396.1918).

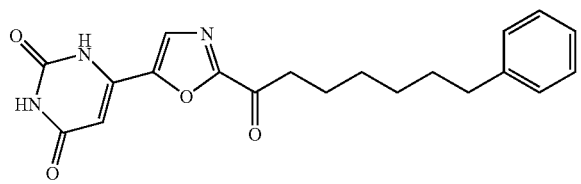

Example 52

6-(2-(7-Phenylheptanoyl)oxazol-5-yl)pyrimidine-2,4(1H,3H)-dione

The title compound was prepared from 1-(5-(2,6-dimethoxypyrimidin-4-yl)oxazol-2-yl)-7-phenylheptan-1-one (20 mg, 0.051 mmol) following General Procedure H. Flash chromatography (EtOAc) yielded the title compound as a white solid (16 mg, 90%): $^1$H NMR (CDCl$_3$/CD$_3$OD, 500 MHz) δ 7.92 (s, 1H), 7.28-7.24 (m, 2H), 7.18-7.15 (m, 3H), 6.19 (s, 1H), 3.06 (t, 2H, J=7.4 Hz), 2.58 (t, 2H, J=7.7 Hz), 1.73 (quintet, 2H, J=7.3 Hz), 1.61 (quintet, 2H, J=7.4 Hz), 1.38-1.36 (m, 4H); $^{13}$C NMR (CDCl$_3$, 125 MHz) δ 188.3, 163.8, 158.0, 151.7, 144.9, 142.5, 139.1, 129.8, 128.3, 128.1, 125.5, 98.8, 39.2, 35.7, 31.1, 28.81, 28.78, 23.5; MALDI-FTMS m/z 368.1595 (M+H$^+$, C$_{20}$H$_{22}$N$_3$O$_4$, requires 368.1605).

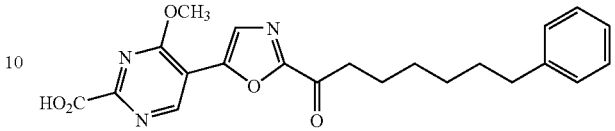

Example 53

1-(5-(2,4-Dimethoxypyrimidin-5-yl)oxazol-2-yl)-7-phenylheptan-1-one

Step 1; 2-(1-(tert-butyldimethylsilyloxy)-7-phenylheptyl)-5-(2,4-dimethoxypyrimidin-5-yl)oxazole. The title compound was prepared from 2-(1-(tert-butyldimethylsilyloxy)-7-phenylheptyl)-5-(tributylstannyl)oxazole (130 mg, 0.196 mmol) and 5-iodo-2,6-dimethoxypyrimidine following General Procedure A. Flash chromatography (10% EtOAc/hexanes) yielded the title compound as a thick oil (85 mg, 83%): $^1$H NMR (CDCl$_3$, 400 MHz) δ 8.67 (s, 1H), 7.34 (s, 1H), 7.28-7.24 (m, 2H), 7.18-7.14 (m, 3H), 4.85 (dd, 1H, J=7.4, 5.9 Hz), 4.13 (s, 3H), 4.05 (s, 3H), 2.59 (t, 2H, J=7.8 Hz), 1.93 (m, 2H), 1.60 (m, 2H), 1.41 (m, 4H), 0.89 (s, 9H), 0.09 (s, 3H), 0.01 (s, 3H); $^{13}$C NMR (CDCl$_3$, 100 MHz) δ 166.4, 164.3, 154.1, 143.9, 142.7, 128.3, 128.1, 125.5, 125.2, 104.9, 68.5, 55.0, 54.4, 36.3, 35.8, 31.3, 29.1, 25.6, 25.6, 25.0, 18.1, −5.0, −5.2.

Step 2. The title compound was prepared from 2-(1-(tert-butyldimethylsilyloxy)-7-phenylheptyl)-5-(2,4-dimethoxypyrimidin-5-yl)oxazole (85 mg, 0.166 mmol) following General Procedure C. Flash chromatography (30% EtOAc/hexanes) yielded the title compound as a white solid (43 mg, 66%): $^1$H NMR (CDCl$_3$, 400 MHz) δ 8.82 (s, 1H), 7.57 (s, 1H), 7.28-7.24 (m, 2H), 7.14-7.18 (m, 3H), 4.17 (s, 3H), 4.07 (s, 3H), 3.08 (t, J=7.5 Hz), 2.61 (t, 2H, J=7.6 Hz), 1.77 (quint, 2H, J=7.3 Hz), 1.64 (quint, 2H, J=7.4 Hz), 1.45-1.38 (m, 4H); $^{13}$C NMR (CDCl$_3$, 100 MHz) δ 188.2, 166.9, 165.1, 156.4, 156.0, 147.4, 142.6, 128.3, 128.2, 126.9, 125.5, 103.6, 55.3, 54.6, 38.9, 35.8, 31.2, 28.9, 28.9, 23.9; MALDI-FTMS m/z 396.1920 (M+H$^+$, C$_{22}$H$_{26}$N$_3$O$_4$, requires 396.1918).

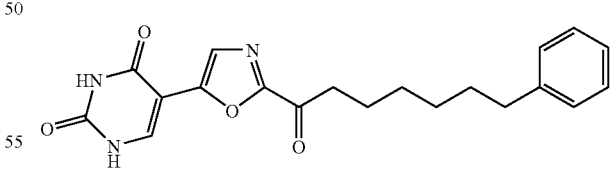

Example 54

5-(2-(7-Phenylheptanoyl)oxazol-5-yl)pyrimidine-2,4(1H,3H)-dione

The title compound was prepared from 1-(5-(2,4-dimethoxypyrimidin-5-yl)oxazol-2-yl)-7-phenylheptan-1-one (15 mg, 0.038 mmol) following General Procedure H. Flash chromatography (EtOAc) yielded the title compound as a white solid (10 mg, 71%): $^1$H NMR (CDCl$_3$, 400 MHz) δ 7.90 (s, 1H), 7.71 (s, 1H), 7.28-7.24 (m, 2H), 7.18-7.14 (m, 3H), 2.99 (t, J=7.5 Hz), 2.52 (t, 2H, J=7.8 Hz), 1.67 (quint, 2H, J=7.3 Hz), 1.55 (quint, 2H, J=7.4 Hz), 1.33-1.31 (m, 4H); $^{13}$C NMR (CDCl$_3$, 100 MHz) δ 188.8, 160.9, 155.4, 150.6, 147.4, 142.5, 139.0, 128.2, 128.0, 126.0, 125.4, 102.6, 38.6, 35.6, 31.1, 28.8, 28.8, 23.8; MALDI-FTMS m/z 368.1613 (M+H$^+$, C$_{20}$H$_{21}$N$_3$O$_4$, requires 368.1610).

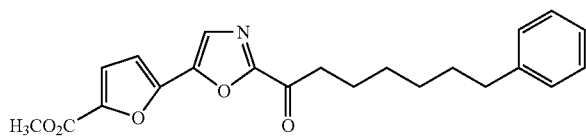

Example 55

Methyl 5-(2-(7-phenylheptanoyl)oxazol-5-yl)furan-2-carboxylate

Step 1; Methyl 5-(2-(1-(tert-butyldimethylsilyloxy)-7-phenylheptyl)oxazol-5-yl)furan-2-carboxylate. The title compound was prepared from 2-(1-(tert-butyldimethylsilyloxy)-7-phenylheptyl)-5-(tributylstannyl)oxazole (82 mg, 0.125 mmol) and methyl 5-bromofuran-2-carboxylate following General Procedure A. Flash chromatography (2-10% EtOAc/hexanes) yielded the title compound as a clear oil (62 mg, 99%): $^1$H NMR (CDCl$_3$, 400 MHz) δ 7.42 (s, 1H), 7.29-7.25 (m, 3H), 7.19-7.16 (m, 3H), 6.70 (d, 1H, J=3.6 Hz), 4.83 (t, 1H, J=6.0 Hz), 3.92 (s, 3H), 2.60 (t, 2H, J=7.6 Hz), 1.96-1.85 (m, 2H), 1.71-1.57 (m, 2H), 1.40-1.33 (m, 6H), 0.90 (s, 9H), 0.10 (s, 3H), 0.00 (s, 3H); $^{13}$C NMR (CDCl$_3$, 100 MHz) δ 163.8, 151.9, 149.1, 147.8, 147.5, 133.4, 133.2, 130.6, 129.3, 124.6, 113.6, 113.5, 73.6, 57.1, 41.3, 40.9, 36.4, 34.1, 30.7, 30.7, 30.1, 23.2, 0.0, −0.1.

Step 2. The title compound was prepared from methyl 5-(2-(1-(tert-butyldimethylsilyloxy)-7-phenylheptyl)oxazol-5-yl)furan-2-carboxylate (60 mg, 0.121 mmol) following General Procedure C. Flash chromatography (10-20% EtOAc/hexanes) yielded the title compound as a white solid (29 mg, 63%): $^1$H NMR (CDCl$_3$, 500 MHz) δ 7.72 (s, 1H), 7.36-7.33 (m, 4H), 7.25-7.23 (m, 2H), 7.04-7.03 (d, J=3.5 Hz, 1H), 4.02 (s, 3H), 3.16 (t, 2H, J=7.5 Hz), 2.69 (t, 2H, J=7.5 Hz), 1.88-1.82 (m, 2H), 1.75-1.69 (m, 2H), 1.54-1.44 (m, 4H); $^{13}$C NMR (CDCl$_3$, 125 MHz) δ 188.5, 162.3, 159.0, 145.9, 145.8, 143.1, 128.8, 128.7, 128.7, 126.1, 126.0, 119.9, 111.7, 52.7, 39.6, 36.3, 31.7, 29.4, 29.4, 24.3; MALDI-FTMS m/z 382.1640 (M+H$^+$, C$_{22}$H$_{24}$NO$_5$, requires 382.1649).

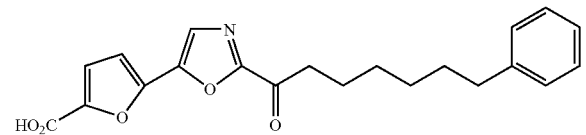

Example 56

5-(2-(7-Phenylheptanoyl)oxazol-5-yl)furan-2-carboxylic acid

The title compound was prepared from methyl 5-(2-(7-phenylheptanoyl)oxazol-5-yl)furan-2-carboxylate (7 mg, 0.018 mmol) following General Procedure E. Preparative thin layer chromatography (10% MeOH/CH$_2$Cl$_2$) yielded the title compound as a white solid (6 mg, 85%): $^1$H NMR (THF-d$_8$, 500 MHz) δ 7.68 (s, 1H), 7.27 (d, 1H, J=3.5 Hz), 7.22-7.07 (m, 5H), 7.04 (d, 1H, J=4.0 Hz), 3.05 (t, 2H, J=7.0 Hz), 2.60 (t, 2H, J=7.5 Hz), 1.73-1.71 (m, 2H), 1.65-1.61 (m, 2H), 1.42-1.40 (m, 4H); $^{13}$C NMR NMR (THF-d$_8$, 125 MHz) δ 187.6, 164.6, 158.3, 146.2, 145.8, 143.5, 129.1, 128.9, 128.9, 126.3, 126.0, 119.7, 111.7, 39.6, 36.7, 32.4, 30.0, 30.0, 24.6; MALDI-FTMS m/z 368.1501 (M+H$^+$, C$_{21}$H$_{22}$NO$_5$, requires 368.1492).

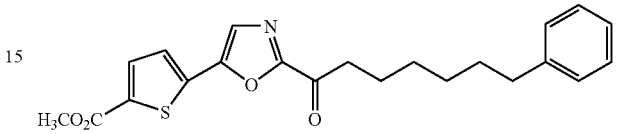

Example 57

Methyl 5-(2-(7-phenylheptanoyl)oxazol-5-yl)thiophene-2-carboxylate

Step 1; Methyl 5-(2-(1-(tert-butyldimethylsilyloxy)-7-phenylheptyl)oxazol-5-yl)thiophene-2-carboxylate. The title compound was prepared from 2-(1-(tert-butyldimethylsilyloxy)-7-phenylheptyl)-5-(tributylstannyl)oxazole (89 mg, 0.134 mmol) and methyl 5-bromothiophene-2-carboxylate following General Procedure A. Flash chromatography (2-10% EtOAc/hexanes) yielded the title compound as a clear oil (65 mg, 94%): $^1$H NMR (CDCl$_3$, 400 MHz) δ 7.72 (d, 1H, J=3.6 Hz), 7.26-7.23 (m, 4H), 7.17-7.14 (m, 3H), 4.80 (t, 1H, J=6.0 Hz), 3.89 (s, 3H), 2.58 (t, 2H, J=7.6 Hz), 1.95-1.87 (m, 2H), 1.68-1.56 (m, 2H), 1.38-1.27 (m, 6H), 0.88 (s, 9H), 0.09 (s, 3H), 0.00 (s, 3H); $^{13}$C NMR (CDCl$_3$, 100 MHz) δ 167.4, 150.8, 147.9, 141.3, 139.2, 137.7, 133.5, 133.3, 130.7, 129.2, 129.2, 128.5, 73.7, 57.5, 41.4, 41.0, 36.5, 34.2, 30.8, 30.9, 30.2, 23.3, 0.2, 0.0.

Step 2. The title compound was prepared from methyl 5-(2-(1-(tert-butyldimethylsilyloxy)-7-phenylheptyl)oxazol-5-yl)thiophene-2-carboxylate (63 mg, 0.123 mmol) following General Procedure C. Flash chromatography (5-20% EtOAc/hexanes) yielded the title compound as a white solid (25 mg, 50%): $^1$H NMR (CDCl$_3$, 500 MHz) δ 7.85 (d, 1H, J=4.0 Hz), 7.54-7.53 (m, 2H), 7.36-7.33 (m, 2H), 7.26-7.24 (m, 3H), 4.00 (s, 3H), 3.15 (t, 2H, J=7.5 Hz), 2.69 (t, 2H, J=7.5 Hz), 1.86-1.82 (m, 2H), 1.75-1.69 (m, 2H), 1.54-1.44 (m, 4H); $^{13}$C NMR (CDCl$_3$, 125 MHz) δ 188.4, 162.4, 157.4, 148.9, 143.1, 135.3, 134.7, 134.5, 128.8, 128.7, 127.0, 126.0, 125.4, 53.0, 39.5, 36.3, 31.7, 29.4, 29.4, 24.4; MALDI-FTMS m/z 398.1407 (M+H$^+$, C$_{22}$H$_{24}$NO$_4$S, requires 398.1420).

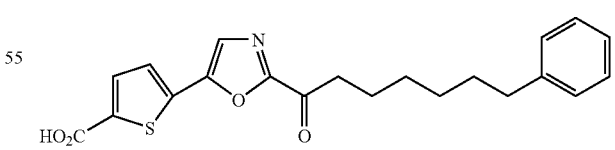

Example 58

5-(2-(7-Phenylheptanoyl)oxazol-5-yl)thiophene-2-carboxylic acid

The title compound was prepared from methyl 5-(2-(7-phenylheptanoyl)oxazol-5-yl)thiophene-2-carboxylate (7 mg, 0.018 mmol) following General Procedure E. Preparative thin layer chromatography (10% MeOH/CH$_2$Cl$_2$) yielded the title compound as a white solid (3 mg, 41%): $^1$H NMR (THF-d$_8$, 500 MHz) δ 7.73 (d, 1H, J=3.5 Hz), 7.72 (s, 1H), 7.55 (d, 1H, J=4.0 Hz), 7.22-7.08 (m, 5H), 3.03 (t, 2H, J=7.0 Hz), 2.60 (t, 2H, J=7.5 Hz), 1.73-1.71 (m, 2H), 1.65-1.61 (m, 2H), 1.42-1.40 (m, 4H); $^{13}$C NMR NMR (THF-d$_8$, 125 MHz) δ 185.1, 164.0, 155.8, 147.0, 141.0, 134.8, 132.7, 132.1, 126.7, 126.5, 124.9, 123.9, 123.3, 37.0, 34.3, 30.0, 27.6, 27.5, 22.2; MALDI-FTMS m/z 384.1272 (M+H$^+$, C$_{21}$H$_{22}$NO$_4$S, requires 384.1264).

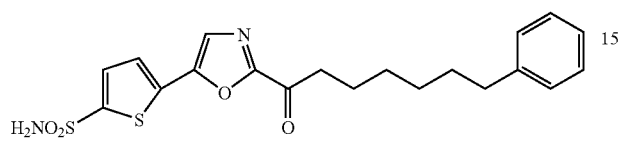

Example 59

5-(2-(7-Phenylheptanoyl)oxazol-5-yl)thiophene-2-sulfonamide

Step 1: 5-(2-(1-(tert-Butyldimethylsilyloxy)-7-phenylheptyl)oxazol-5-yl)thiophene-2-sulfonamide. The title compound was prepared from 2-(1-(tert-butyldimethylsilyloxy)-7-phenylheptyl)-5-(tributylstannyl)oxazole (54 mg, 0.081 mmol) and 5-bromothiophene-2-sulfonamide following General Procedure A. Flash chromatography (10-20% EtOAc/hexanes) yielded the title compound as a white solid (33 mg, 75%): $^1$H NMR (CDCl$_3$, 500 MHz) δ 7.68 (d, 1H, J=4.0 Hz), 7.36-7.33 (m, 3H), 7.29 (d, 1H, J=3.5 Hz), 7.26-7.23 (m, 3H), 5.29 (s, 2H), 4.89 (t, 1H, J=6.0 Hz), 2.67 (t, 2H, J=7.5 Hz), 2.02-1.95 (m, 2H), 1.74-1.59 (m, 2H), 1.40-1.38 (m, 6H), 0.97 (s, 9H), 0.17 (s, 3H), 0.08 (s, 3H); $^{13}$C NMR (CDCl$_3$, 125 MHz) δ 166.2, 145.2, 143.2, 142.5, 136.4, 132.7, 128.8, 128.7, 126.0, 124.2, 123.8, 68.9, 36.7, 36.3, 31.8, 29.6, 26.1, 26.1, 25.5, 18.6, −4.5, −4.7.

Step 2. The title compound was prepared from 5-(2-(1-(tert-butyldimethylsilyloxy)-7-phenylheptyl)oxazol-5-yl)thiophene-2-sulfonamide (30 mg, 0.056 mmol) following General Procedure C. Flash chromatography (30-60% EtOAc/hexanes) yielded the title compound as a white solid (11 mg, 46%): $^1$H NMR (CDCl$_3$, 500 MHz) δ 7.71 (d, 1H, J=3.5 Hz), 7.55 (s, 1H), 7.50 (d, 1H, J=3.5 Hz), 7.90 (s, 1H), 7.37-7.34 (m, 2H), 7.26-7.24 (m, 3H), 5.36 (s, 2H), 3.15 (t, 2H, J=7.0 Hz), 2.69 (t, 2H, J=7.5 Hz), 1.87-1.82 (m, 2H), 1.75-1.69 (m, 2H), 1.54-1.46 (m, 4H); $^{13}$C NMR (CDCl$_3$, 500 MHz) δ 188.5, 144.9, 143.1, 143.5, 133.3, 132.6, 128.8, 128.7, 126.4, 126.1, 125.7, 125.6, 39.6, 36.3, 31.7, 29.4, 29.4, 24.3; MALDI-FTMS m/z 419.1093 (M+H$^+$, C$_{20}$H$_{22}$N$_2$O$_4$S$_2$, requires 419.1094).

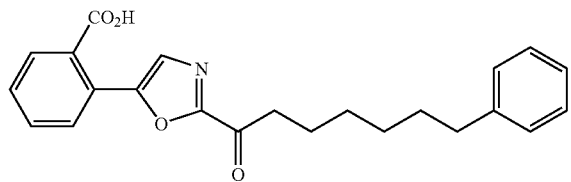

Example 60

2-(2-(7-Phenylheptanoyl)oxazol-5-yl)benzoic acid

The following compounds in Examples 61 and 62 may be prepared using methods analogous to those described in the preceding examples.

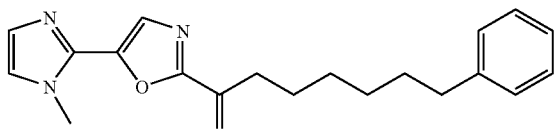

Example 61

1-[5-(1-Methyl-1H-imidazol-2-yl)-oxazol-2-yl]-7-phenyl-heptan-1-one

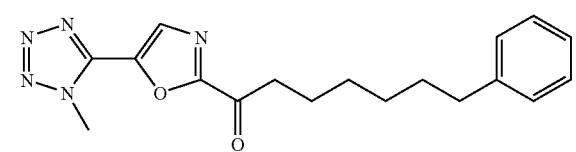

Example 62

1-[5-(1-Methyl-1H-tetrazol-5-yl)-oxazol-2-yl]-7-phenyl-heptan-1-one

The title compounds per se of Comparative Examples 1 and 2 are known and are provided for comparative purposes. Compounds in Comparative Examples 1 and 2 were prepared according to the general procedures described above or according to the procedures described in WO 04/033652.

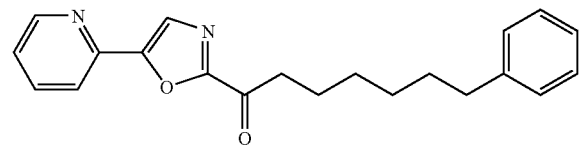

Comparative Example 1

7-Phenyl-1-(5-pyridin-2-yl-oxazol-2-yl)-heptan-1-one

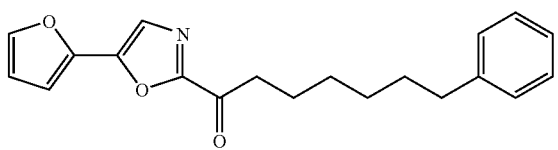

Comparative Example 2

1-(5-Furan-2-yl-oxazol-2-yl)-7-phenyl-heptan-1-one

Biological Testing:
Assay Method 1A

All enzyme assays were performed at 20-23° C. using a solubilized liver plasma membrane extract containing FAAH in a reaction buffer of 125 mM Tris, 1 mM EDTA, 0.2% glycerol, 0.02% Triton X-100, 0.4 mM HEPES, pH 9.0 buffer (Patricelli, M. P. et al. *Bioorg. Med. Chem. Lett.* 1998, 8, 613-618; Patterson, J. E., et al. J. Am Chem. Soc. 1996, 118, 5938-5945). The initial rates of hydrolysis were monitored by following the breakdown of $^{14}C$-oleamide to oleic acid as described previously (Cravatt, B. F. et al. *Science* 1995, 268, 1506-1509; Patricelli, M. P. et al. 1998). The inhibition was reversible, non time-dependent. Linear least squares fits were used for all reaction progress curves and $R^2$ values were consistently >0.97. $IC_{50}$ values were determined from the inhibition observed at 3-5 different test compound concentrations (from three or more trials at each concentration) using the formula $IC_{50}=[I]/[K_0/K_i)-1]$, where $K_0$ is the control reaction rate without inhibitor and $K_i$ is the rate with test compound at concentration [I] (Conde-Frieboes, K., et al. *J. Am. Chem. Soc.* 1996, 118, 5519-5525). $K_i$ values were determined by the Dixon Method (x-intercepts of weighted linear fits of [I] versus 1/rate plots at constant substrate concentration, which were converted to $K_i$ values using the formula $K_i=-x_{int}/[1+[S]/K_m]$). Results for compounds tested in this assay are presented in presented in Table 1.

TABLE I

| Ex. | Assay 1A $K_i$ (nM) | Ex. | Assay 1A $K_i$ (nM) |
|---|---|---|---|
| 1 | 125 | 38 | 7 |
| 2 | 28 | 39 | 50 |
| 10 | 110 | 40 | >50 |
| 11 | 60 | 41 | 3 |
| 13 | 400 | 42 | 3 |
| 14 | 40 | 43 | 1 |
| 19 | 1500 | 44 | 15 |
| 20 | 2 | 45 | 2 |
| 21 | 10 | 46 | 2 |
| 22 | 60 | 47 | 4 |
| 23 | 12 | 48 | 3 |
| 24 | 40 | 49 | 25 |
| 25 | 5 | 50 | 2 |
| 26 | 60 | 51 | 5 |
| 27 | 750 | 52 | 19 |
| 28 | 19 | 53 | 26 |
| 30 | 170 | 55 | 6 |
| 31 | 50 | 56 | 15 |
| 33 | 8 | 57 | 7 |
| 34 | 4 | 58 | 11 |
| 35 | 1 | 59 | 3 |
| 36 | >50 | 60 | 6000 |
| 37 | 20 | | |

Assay Method 1B
A. Transfection of Cells with Human FAAH

A 10-cm tissue culture dish with a confluent monolayer of SK—N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% $CO_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 μL complete media and transferred to an electroporation cuvette with a 0.4 cm gap between the electrodes. Supercoiled human FAAH cDNA (1 μg) was added to the cells and mixed. The voltage for the electroporation was set at 0.25 kV, and the capacitance was set at 960 μF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 μg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK—N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 μL of the cell homogenate, 10 μL of the test compound, and 40 μL of anandamide [1-$^3H$-ethanolamine] ($^3H$-AEA, Perkin-Elmer, 10.3 $C_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 μL of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount. Results for compounds tested in this assay are presented in Table 2.

Assay Method 2
A. Transfection of Cells with Rat FAAH

A 10-cm tissue culture dish with a confluent monolayer of SK—N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% $CO_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 μL complete media and transferred to an electroporation cuvette with a 0.4 cm gap between the electrodes. Supercoiled rat FAAH cDNA (1 μg) was added to the cells and mixed. The voltage for the electroporation was set at 0.25 kV, and the capacitance was set at 960 μF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish.

The cells were allowed to recover for 24 h before adding the selection media (complete media with 600 μg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK—N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 μL of the cell homogenate, 10 μL of the test compound, and 40 μL of anandamide [1-$^3$H-ethanolamine] ($^3$H-AEA, Perkin-Elmer, 10.3 C$_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 μL of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount. Results for compounds tested in this assay are presented in Table 2.

TABLE 2

| Ex. | Assay 1B IC$_{50}$ (nM) | Assay 2 IC$_{50}$ (nM) | Ex. | Assay 1B IC$_{50}$ (nM) | Assay 2 IC$_{50}$ (nM) |
|---|---|---|---|---|---|
| 1 | 340 | 500 | 24 | 24 | 1000 |
| 2 | 50 | 500 | 25 | 4 | 11 |
| 3 | 110 | 500 | 26 | 6 | 160 |
| 4 | 10000 | 10000 | 27 | 1000 | 4000 |
| 5 | 40 | 500 | 28 | 17 | 290 |
| 6 | 260 | 1700 | 29 | 280 | 980 |
| 7 | 160 | 1800 | 30 | 115 | 3500 |
| 8 | 12 | 34 | 31 | 55 | 570 |
| 9 | 10 | 60 | 32 | 450 | 1800 |
| 10 | 1600 | 9000 | 33 | 6 | 70 |
| 11 | 220 | 6300 | 34 | 11 | 9 |
| 12 | 100 | 1000 | 36 | 180 | 150 |
| 13 | 1900 | 10000 | 37 | 0.4 | 11 |
| 14 | 100 | 4500 | 38 | 0.2 | 2 |
| 15 | 770 | 4000 | 52 | 0.1 | 1.5 |
| 16 | 110 | 2000 | 54 | 8000 | 47 |
| 17 | 9 | 520 | 55 | 11 | 20 |
| 18 | 290 | 220 | 56 | 0.8 | 2 |
| 19 | 2000 | 10000 | 57 | 6 | 75 |
| 20 | 4 | 27 | 58 | 1 | 9 |
| 21 | 8 | 53 | 59 | 2 | 8 |
| 22 | 260 | 2200 | 60 | 440 | 3000 |
| 23 | 15 | 100 | | | |

Physical Chemical Properties

Solubility determinations were made by mixing the test compound in water at 5 mg/mL, 1 mg/mL, and 0.1 mg/mL concentrations. The pH of the resulting solutions was 7-8.5. Results for compounds tested are presented in Table 3.

TABLE 3

| Ex. | Solubility |
|---|---|
| Comp. Ex. 1 | <0.1 mg/mL |
| Comp. Ex. 2 | <0.1 mg/mL |
| 37 | >5.0 mg/mL |
| 38 | >5.0 mg/mL |
| 56 | >5.0 mg/mL |

Pharmacokinetic Testing

For each test compound, two male Sprague Dawley Rats (Charles River Laboratories; approx. 300 g body weight) were used. Animals were individually housed, provided food and water ad libitum, and were maintained on a 12 h light and dark cycle. Animals received from the vendor were surgically cannulated by the vendor with right jugular vein and left carotid artery catheters. Animals were acclimatized for at least 5 days after receipt from the vendor prior to investigations.

Animals received a bolus intravenous dose of the test compound at a dose of 1 mg/mL in a volume of 2 mL/kg via the right jugular vein catheter. The intravenous dosing solution was prepared in 55% pharmasolve, 20% cremophor, and 75% physiological saline, or 100% saline adjusted to pH 8.0.

Following intravenous administration, blood was collected (sampled 0.35 mL per time point from the left carotid artery catheter) at 0.083, 0.25, 0.5, 1, 2, 4, and 6 h post-dose. Blood was collected into tubes containing EDTA and stored at 4° C. for not more than 2 h. The samples were centrifuged at 10,000 rpm in a micro-centrifuge for 5 min to obtain a plasma fraction. The plasma was stored at between −20 and −80° C. until processed for analysis. These samples were analyzed by LC-MS/MS to determine the plasma level of the compound.

Plasma level vs. time plots were created and WinNonlin (Pharsight Corp.) was used to analyze the data. A non-compartmental pharmacokinetic model was used to determine the pharmacokinetic parameters, including clearance, volume of distribution ($V_d$), and half-life ($t_{1/2}$). Data for compounds tested in this assay are presented in Table 4.

TABLE 4

| Ex. | Clearance (L/hr/kg) | $V_d$ (L/kg) | $t_{1/2}$ (hr) |
|---|---|---|---|
| Comp. Ex. 1 | 5.9 | 27.3 | 3.23 |
| Comp. Ex. 2 | 3.8 | 22.9 | 3.49 |
| 37 | 0.46 | 0.86 | 1.24 |
| 38 | 6.7 | 1.4 | 0.15 |

While the invention has been illustrated by reference to exemplary and preferred embodiments, it will be understood that the invention is intended not to be limited to the foregoing detailed description, but to be defined by the appended claims as properly construed under principles of patent law.

What is claimed is:

1. A compound of Formula (I):

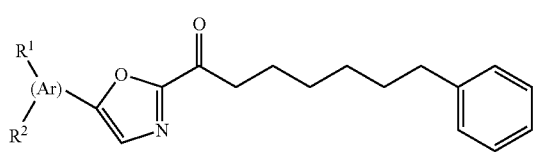

wherein:
Ar is a 5- or 6-membered aryl or heteroaryl ring having a carbon as its point of attachment to the oxazole;
$R^1$ is independently —$C_{3-6}$cycloalkyl, —$CF_3$, —CN, —C(O)$C_{1-4}$alkyl optionally substituted with one, two, or three fluoro substituents, —$CO_2C_{1-4}$alkyl, —$CO_2H$, —C(O)N($R^a$)$R^b$, —OH, —O$C_{1-6}$alkyl, halo, —$NO_2$, —$NR^aR^b$, —N($R^a$)CO$R^b$, —N($R^a$)SO$_2R^b$, SO$_2$N($R^a$)$R^b$, or S(O)$_{0-2}R^a$; where $R^a$ and $R^b$ are each independently —H, —$C_{1-6}$alkyl, or —$C_{3-6}$cycloalkyl; and
$R^2$ is independently —H, —$C_{1-6}$alkyl, —$C_{3-6}$cycloalkyl, —$CF_3$, —CN, —C(O)$C_{1-4}$alkyl optionally substituted with one, two, or three fluoro substituents, —$CO_2C_{1-4}$alkyl, —$CO_2H$, —C(O)N($R^c$)$R^d$, —OH, —O$C_{1-6}$alkyl, halo, —$NO_2$, —$NR^cR^d$, —N($R^c$)CO$R^d$, —N($R^c$)SO$_2R^d$, —SO$_2$N($R^c$)$R^d$, or —S(O)$_{0-2}R^c$;
where $R^c$ and $R^d$ are each independently —H, —$C_{1-6}$alkyl, or —$C_{3-6}$cycloalkyl; or a pharmaceutically acceptable salt of said compound.

2. A compound as defined in claim 1, wherein Ar is selected from the group consisting of phenyl, pyridyl, pyridazinyl, pyrimidinyl, pyrimidine-dione, pyrazinyl, thiophenyl, furanyl, imidazolyl, oxazolyl, and tetrazolyl.

3. A compound as defined in claim 1, wherein Ar is selected from the group consisting of 3-($R^1$)-phenyl, 3-($R^1$)-2-pyridyl, 4-($R^1$)-2-pyridyl, 5-($R^1$)-2-pyridyl, 6-(R1)-2-pyridyl, 5-($R^1$)-2-furanyl, 5-($R^1$)-2-thiophenyl, 1-($R^1$)-1H-2-imidazolyl, and 1-($R^1$)-1H-5-tetrazolyl.

4. A compound as defined in claim 1, wherein $R^1$ is selected from the group consisting of —$CF_3$, —CN, —C(O)$CF_3$, —$CO_2CH_3$, —$CO_2H$, —C(O)$NH_2$, —OH, —$OCH_3$, fluoro, —$NO_2$, —$NH_2$, and —$SO_2NH_2$.

5. A compound as defined in claim 1, wherein $R^2$ is —H.

6. A compound as defined in claim 2, wherein $R^1$ is selected from the group consisting of —$CF_3$, —CN, —C(O)$CF_3$, —$CO_2CH_3$, —$CO_2H$, —C(O)$NH_2$, —OH, —$OCH_3$, fluoro, —$NO_2$, —$NH_2$, and —$SO_2NH_2$.

7. A compound as defined in claim 2, wherein $R^2$ is —H.

8. A compound as defined in claim 3, wherein $R^1$ is selected from the group consisting of —$CF_3$, —CN, —C(O)$CF_3$, —$CO_2CH_3$, —$CO_2H$, —C(O)$NH_2$, —OH, —$OCH_3$, fluoro, —$NO_2$, —$NH_2$, and —$SO_2NH_2$.

9. A compound as defined in claim 3, wherein $R^2$ is —H.

10. A compound as defined in claim 8, wherein $R^2$ is —H.

11. A compound selected from the group consisting of:
1-(5-(2-Nitrophenyl)oxazol-2-yl)-7-phenylheptan-1-one;
1-(5-(3-Nitrophenyl)oxazol-2-yl)-7-phenylheptan-1-one;
1-(5-(4-Nitrophenyl)oxazol-2-yl)-7-phenylheptan-1-one;
7-Phenyl-1-(5-(2-(2,2,2-trifluoroacetyl)phenyl)oxazol-2-yl)heptan-1-one;
7-Phenyl-1-(5-(3-(2,2,2-trifluoroacetyl)phenyl)oxazol-2-yl)heptan-1-one;
7-Phenyl-1-(5-(4-(2,2,2-trifluoroacetyl)phenyl)oxazol-2-yl)heptan-1-one;
2-(2-(7-Phenylheptanoyl)oxazol-5-yl)benzamide;
3-(2-(7-Phenylheptanoyl)oxazol-5-yl)benzamide;
4-(2-(7-Phenylheptanoyl)oxazol-5-yl)benzamide;
1-(5-(2-Fluorophenyl)oxazol-2-yl)-7-phenylheptan-1-one;
1-(5-(3-Fluorophenyl)oxazol-2-yl)-7-phenylheptan-1-one;
1-(5-(4-Fluorophenyl)oxazol-2-yl)-7-phenylheptan-1-one;
1-(5-(2-Methoxyphenyl)oxazol-2-yl)-7-phenylheptan-1-one;
1-(5-(3-Methoxyphenyl)oxazol-2-yl)-7-phenylheptan-1-one;
1-(5-(4-Methoxyphenyl)oxazol-2-yl)-7-phenylheptan-1-one;
2-(2-(7-Phenylheptanoyl)oxazol-5-yl)benzonitrile;
3-(2-(7-Phenylheptanoyl)oxazol-5-yl)benzonitrile;
4-(2-(7-Phenylheptanoyl)oxazol-5-yl)benzonitrile;
2-(2-(7-Phenylheptanoyl)oxazol-5-yl)benzenesulfonamide;
3-(2-(7-Phenylheptanoyl)oxazol-5-yl)benzenesulfonamide;
4-(2-(7-Phenylheptanoyl)oxazol-5-yl)benzenesulfonamide;
Methyl 2-(2-(7-phenylheptanoyl)oxazol-5-yl)benzoate;
Methyl 3-(2-(7-phenylheptanoyl)oxazol-5-yl)benzoate;
Methyl 4-(2-(7-phenylheptanoyl)oxazol-5-yl)benzoate;
3-(2-(7-Phenylheptanoyl)oxazol-5-yl)benzoic acid;
4-(2-(7-Phenylheptanoyl)oxazol-5-yl)benzoic acid;
1-(5-(2-Aminophenyl)oxazol-2-yl)-7-phenylheptan-1-one;
1-(5-(3-Aminophenyl)oxazol-2-yl)-7-phenylheptan-1-one;
1-(5-(4-Aminophenyl)oxazol-2-yl)-7-phenylheptan-1-one;
1-(5-(2-Hydroxyphenyl)oxazol-2-yl)-7-phenylheptan-1-one;
1-(5-(3-Hydroxyphenyl)oxazol-2-yl)-7-phenylheptan-1-one;
1-(5-(4-Hydroxyphenyl)oxazol-2-yl)-7-phenylheptan-1-one;
Methyl 6-(2-(7-phenylheptanoyl)oxazol-5-yl)picolinate;
Methyl 6-(2-(7-phenylheptanoyl)oxazol-5-yl)nicotinate;
Methyl 2-(2-(7-phenylheptanoyl)oxazol-5-yl)isonicotinate;
Methyl 2-(2-(7-phenylheptanoyl)oxazol-5-yl)nicotinate;
6-(2-(7-Phenylheptanoyl)oxazol-5-yl)picolinic acid;
6-(2-(7-Phenylheptanoyl)oxazol-5-yl)nicotinic acid;
2-(2-(7-Phenylheptanoyl)oxazol-5-yl)isonicotinic acid;
2-(2-(7-Phenylheptanoyl)oxazol-5-yl)nicotinic acid;
1-(5-(4-Methoxypyridin-2-yl)oxazol-2-yl)-7-phenylheptan-1-one;
2-(2-(7-Phenylheptanoyl)oxazol-5-yl)isonicotinonitrile;
7-Phenyl-1-(5-(4-(trifluoromethyl)pyridin-2-yl)oxazol-2-yl)heptan-1-one;
1-(5-(4-Nitropyridin-2-yl)oxazol-2-yl)-7-phenylheptan-1-one;
1-(5-(4-Aminopyridin-2-yl)oxazol-2-yl)-7-phenylheptan-1-one;
1-(5-(4-Nitropyridin-2-yl)oxazol-2-yl)-7-phenylheptan-1-one;
1-(5-(2,6-Dimethoxypyrimid in-4-yl)oxazol-2-yl)-7-phenylheptan-1-one;
6-(2-(7-Phenylheptanoyl)oxazol-5-yl)pyrimidine-2,4(1H,3H)-dione;
1-(5-(2,4-Dimethoxypyrimidin-5-yl)oxazol-2-yl)-7-phenylheptan-1-one;
5-(2-(7-Phenylheptanoyl)oxazol-5-yl)pyrimidine-2,4(1H,3H)-dione;
Methyl 5-(2-(7-phenylheptanoyl)oxazol-5-yl)furan-2-carboxylate;
5-(2-(7-Phenylheptanoyl)oxazol-5-yl)furan-2-carboxylic acid;
Methyl 5-(2-(7-phenylheptanoyl)oxazol-5-yl)thiophene-2-carboxylate;

5-(2-(7-Phenylheptanoyl)oxazol-5-yl)thiophene-2-carboxylic acid;

5-(2-(7-Phenylheptanoyl)oxazol-5-yl)thiophene-2-sulfonamide; and 2-(2-(7-Phenylheptanoyl)oxazol-5-yl)benzoic acid;

or a pharmaceutically acceptable salt of said compound.

12. A method of treating a subject suffering from or diagnosed with a disease, disorder, or medical condition for which inhibition of FAAH activity is medically indicated, wherein the disease, disorder, or medical condition is selected from the group consisting of: pain and sleep disorders, comprising administering to the subject an effective amount of a compound of Formula (I) of claim 1, or a pharmaceutically acceptable salt of said compound.

13. A pharmaceutical composition comprising:
(a) an effective amount of an agent selected from compounds of Formula (I) of claim 1, and pharmaceutically acceptable salts thereof; and
(b) a pharmaceutically acceptable excipient.

14. A pharmaceutical composition according to claim 13, further comprising: an analgesic selected from the group consisting of opioids and non-steroidal anti-inflammatory drugs.

15. A pharmaceutical composition according to claim 13, further comprising: an analgesic selected from the group consisting of aspirin, acetaminophen, ibuprofen, naproxen, COX-2 inhibitors, gabapentin, pregabalin, and tramadol.

* * * * *

UNITED STATES PATENT AND TRADEMARK OFFICE
CERTIFICATE OF CORRECTION

PATENT NO.       : 7,915,270 B2
APPLICATION NO.  : 11/708788
DATED            : March 29, 2011
INVENTOR(S)      : Dale L. Boger It is certified that error appears in the above-identified patent and that said Letters Patent is hereby corrected as shown below:

On the title page, item (56), under "Other Publications", in column 1, line 7, delete "1992-1996, 1996*" and insert -- 1992-1996* --, therefor.

In column 1, line 47, delete "Fonesca," and insert -- Fonseca, --, therefor.

In column 5, line 16, delete "1)," and Insert -- /), --, therefor.

In column 7, line 49, delete "Propertions," and insert -- Properties, --, therefor.

In column 8, line 62, delete "norvalin," and insert -- norvaline, --, therefor.

In column 17, line 4, delete "pyrimdine" and insert -- pyrimidine --, therefor.

In column 17, line 4, delete "NaI" and insert -- NaI --, therefor.

In column 17, line 46, delete "1 H," and insert -- 1H, --, therefor.

In column 30, line 44, delete "m/z413.1540" and insert -- m/z 413.1540 --, therefor.

In column 31, line 19, delete "m/z413.1539" and insert -- m/z 413.1539 --, therefor.

In column 34, line 58, after "34.3," insert -- 34.3, --.

In column 43, line 15, delete "1:" and insert -- 1; --, therefor.

In column 48, line 33, delete "1:" and insert -- 1; --, therefor.

Signed and Sealed this
Seventh Day of June, 2011

David J. Kappos
*Director of the United States Patent and Trademark Office*

CERTIFICATE OF CORRECTION (continued)

In column 50, lines 6-15, delete " 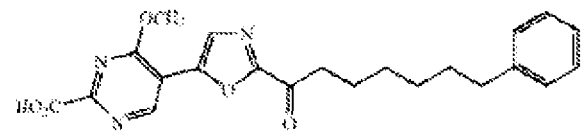 " and insert -- 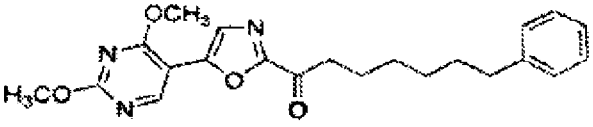 --, therefor.

In column 53, line 27, delete "1:" and insert -- 1; --, therefor.

In column 53, line 56, delete "m/z419.1093" and insert -- m/z 419.1093 --, therefor.

In column 55, line 16, delete "et al." and insert -- et al., --, therefor.

In column 59, line 26, In Claim 3, delete "(R1)" and insert -- ($R^1$) --, therefor.

In column 59, line 49, in Claim 11, delete "7-Phenyl-1 -" and insert -- 7-Phenyl-1- --, therefor.

In column 59, line 51, in Claim 11, delete "7-Phenyl-1 -" and insert -- 7-Phenyl-1- --, therefor.

In column 59, line 53, in Claim 11, delete "7-Phenyl-1 -" and insert -- 7-Phenyl-1- --, therefor.